US010825567B1

(12) United States Patent
Wala et al.

(10) Patent No.: US 10,825,567 B1
(45) Date of Patent: Nov. 3, 2020

(54) APPARATUS AND METHOD FOR INFORMED PERSONAL WELL-BEING DECISION MAKING

(71) Applicant: American Institute of Nutrition and Management Inc., Shoreview, MN (US)

(72) Inventors: Fazal Wala, Shoreview, MN (US); Alexander B. Lemaire, Minneapolis, MN (US); Charles A. Lemaire, Apple Valley, MN (US)

(73) Assignee: Food2Life, LLC, Shoreview, MN (US)

( * ) Notice: Subject to any disclaimer, the term of this patent is extended or adjusted under 35 U.S.C. 154(b) by 451 days.

(21) Appl. No.: 15/243,945

(22) Filed: Aug. 22, 2016

Related U.S. Application Data

(60) Provisional application No. 62/208,574, filed on Aug. 22, 2015, provisional application No. 62/208,570, filed on Aug. 21, 2015.

(51) Int. Cl.
*G16H 50/20* (2018.01)
*G06N 20/00* (2019.01)
(Continued)

(52) U.S. Cl.
CPC ......... *G16H 50/20* (2018.01); *G06Q 30/0627* (2013.01); *G16H 10/60* (2018.01)

(58) Field of Classification Search
CPC .... G16H 50/20; G16H 10/60; G06Q 30/0627; G06Q 50/22; G06Q 50/24; G06F 19/30; G06F 19/32; G06F 19/34
See application file for complete search history.

(56) References Cited

U.S. PATENT DOCUMENTS 5,478,989 A    12/1995  Shepley
5,668,718 A     9/1997  Liu et al.
(Continued)

FOREIGN PATENT DOCUMENTS

WO    WO_2008074340       6/2008
WO    WO_2013173383 A1   11/2013

OTHER PUBLICATIONS

Colman, et al., "Caloric restriction reduces age-related and all-cause mortality in rhesus monkeys", "Nature Communications", Apr. 1, 2014, vol. 5: 3557.
(Continued)

*Primary Examiner* — Elaine Gort
*Assistant Examiner* — Amanda R. Covington
(74) *Attorney, Agent, or Firm* — Charles A. Lemaire; Jonathan M. Rixen; Lemaire Patent Law Firm, P.L.L.C.

(57) ABSTRACT

An apparatus and method for informed personal-well-being decision making that provides a user with alerts and information, focused on health and wellness, on items they choose for possible consumption. Some embodiments include optical, sonic, smell and other sensors, communications with databases that identify ingredients and effects on health and well-being, as well as user inputs. From user input, GPS, local conditions and alerts, some embodiments determine information specific to the user and their environment. By using established, and creating new, databases, some embodiments compile, compare, transmit and store data on various consumables. Some embodiments provide access to information on the companies, manufacturers, and various other components in an item's trip from dirt to table. Some embodiments establish methods and procedures to ascertain both the point-of-origin and where the consumable has traveled. Some embodiments provide a score for the
(Continued)

specified consumable to show the quality of health provided by the consumable.

20 Claims, 26 Drawing Sheets

(51) Int. Cl.
*G16H 10/60* (2018.01)
*G16H 20/00* (2018.01)
*G16H 40/67* (2018.01)
*G16H 10/20* (2018.01)
*A61B 5/145* (2006.01)
*G06F 19/00* (2018.01)
*G06Q 30/06* (2012.01)

(56) References Cited

U.S. PATENT DOCUMENTS

| | | | |
|---|---|---|---|
| 5,836,312 A * | 11/1998 | Moore | A47G 19/2227 |
| | | | 128/897 |
| 5,841,115 A | 11/1998 | Shepley | |
| 6,024,281 A | 2/2000 | Shepley | |
| 6,076,043 A | 6/2000 | Liu | |
| 6,095,949 A | 8/2000 | Arai | |
| 6,115,692 A | 9/2000 | Liu et al. | |
| 6,232,602 B1 * | 5/2001 | Kerr | G06T 1/20 |
| | | | 250/330 |
| 6,858,182 B1 * | 2/2005 | Ito | G01N 33/497 |
| | | | 340/870.28 |
| 7,496,228 B2 | 2/2009 | Landwehr et al. | |
| 8,055,599 B1 * | 11/2011 | Werth | G06K 9/68 |
| | | | 706/45 |
| 8,166,026 B1 | 4/2012 | Sadler | |
| 8,478,447 B2 | 7/2013 | Fadell et al. | |
| 8,594,850 B1 | 11/2013 | Gourley et al. | |
| 8,690,578 B1 | 4/2014 | Nusbaum et al. | |
| 8,788,448 B2 | 7/2014 | Fadell et al. | |
| 8,855,406 B2 | 10/2014 | Lim et al. | |
| 8,897,539 B2 | 11/2014 | Stone et al. | |
| 8,953,024 B2 | 2/2015 | Wang et al. | |
| 9,065,254 B2 | 6/2015 | Geske et al. | |
| 9,212,996 B2 | 12/2015 | Watson et al. | |
| 9,250,746 B2 | 2/2016 | Wala | |
| 9,291,504 B2 | 3/2016 | Goldring et al. | |
| 10,046,229 B2 * | 8/2018 | Tran | H04W 4/027 |
| 2001/0056359 A1 * | 12/2001 | Abreu | G06K 7/10861 |
| | | | 705/3 |
| 2003/0204359 A1 * | 10/2003 | Blakley | G01D 9/005 |
| | | | 702/130 |
| 2005/0025357 A1 * | 2/2005 | Landwehr | A01M 1/026 |
| | | | 382/170 |
| 2005/0033554 A1 * | 2/2005 | Mork | G06Q 50/22 |
| | | | 702/177 |
| 2005/0131723 A1 * | 6/2005 | Sholl | G06Q 10/06 |
| | | | 705/1.1 |
| 2007/0069004 A1 * | 3/2007 | Adler | G06Q 30/02 |
| | | | 235/375 |
| 2007/0148699 A1 * | 6/2007 | Friesen | G01N 33/5088 |
| | | | 435/7.1 |
| 2008/0172244 A1 | 7/2008 | Coupal et al. | |
| 2008/0201094 A1 * | 8/2008 | Vogt | G06Q 10/00 |
| | | | 702/82 |
| 2012/0005105 A1 * | 1/2012 | Beier | G06Q 10/06 |
| | | | 705/303 |
| 2012/0063638 A1 * | 3/2012 | Lim | G06T 7/285 |
| | | | 382/103 |
| 2012/0329735 A1 * | 12/2012 | Sato | A23L 2/60 |
| | | | 514/23 |
| 2013/0083990 A1 * | 4/2013 | Stone | G06K 9/00208 |
| | | | 382/141 |
| 2013/0215233 A1 * | 8/2013 | Wang | G06T 17/00 |
| | | | 348/47 |
| 2013/0273595 A1 * | 10/2013 | Lee | G01N 30/06 |
| | | | 435/34 |
| 2014/0214618 A1 | 7/2014 | Pedley et al. | |
| 2014/0347491 A1 * | 11/2014 | Connor | A61B 5/1114 |
| | | | 348/158 |
| 2015/0039421 A1 * | 2/2015 | Ford | G06Q 30/0251 |
| | | | 705/14.49 |
| 2016/0112684 A1 * | 4/2016 | Connor | G01N 33/02 |
| | | | 348/158 |

OTHER PUBLICATIONS

Ramsey, et al., "Dietary restriction and aging in rhesus monkeys: the University of Wisconsin study", "Exp Gerontol.", Dec. 2000, pp. 1131-1149, vol. 35, No. 9-10.

* cited by examiner

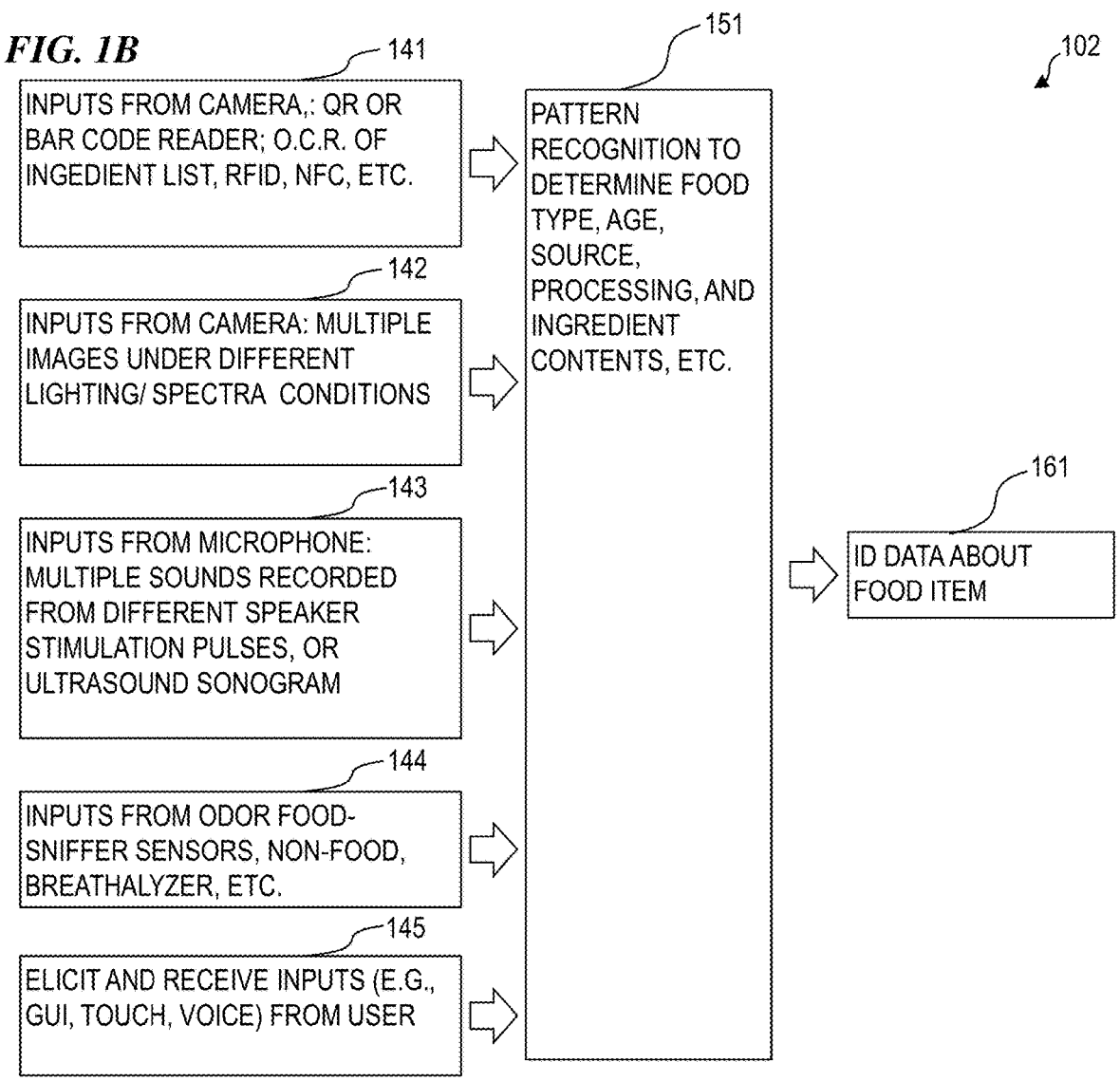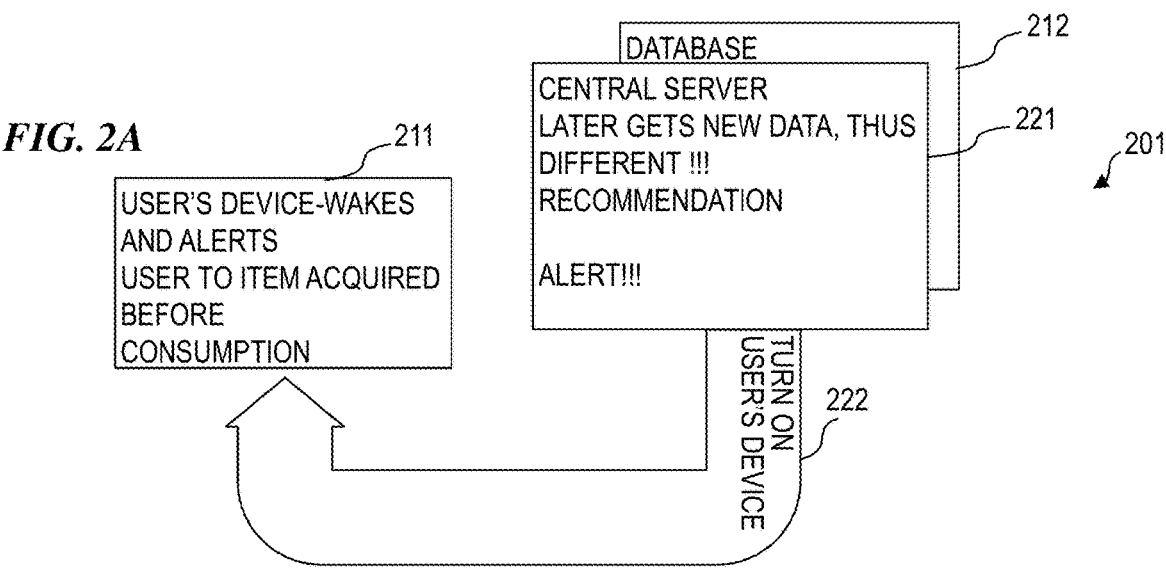

BI-LENSES, MULTIPLE DIFFERENT-COLOR FLASH LEDS
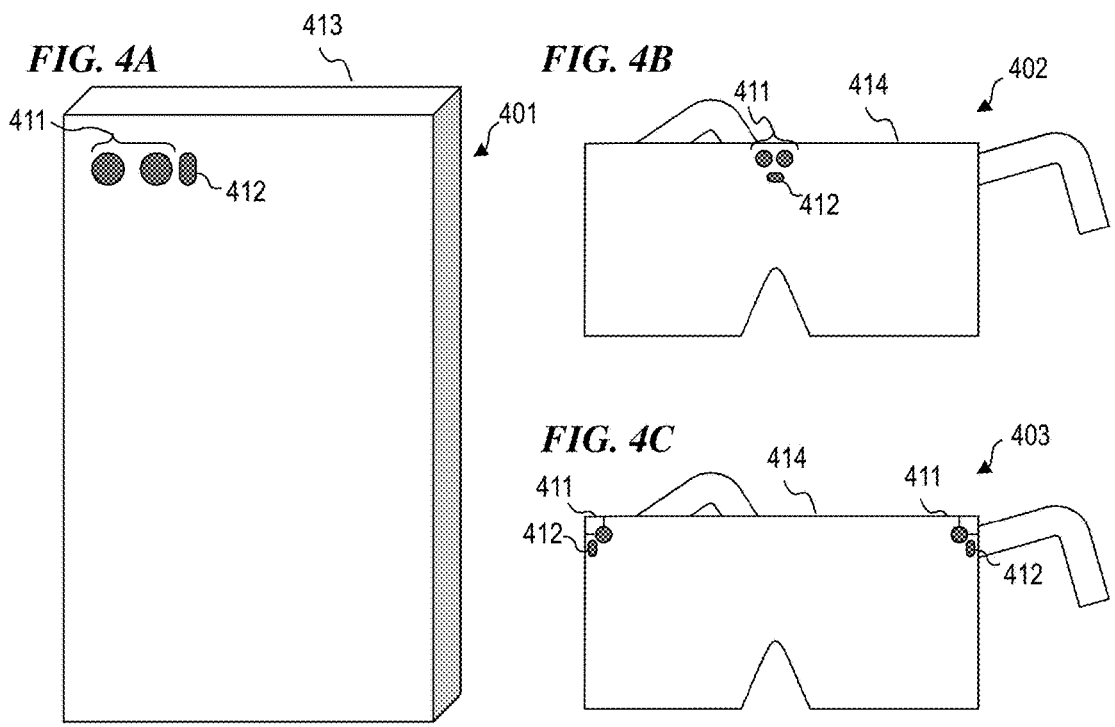
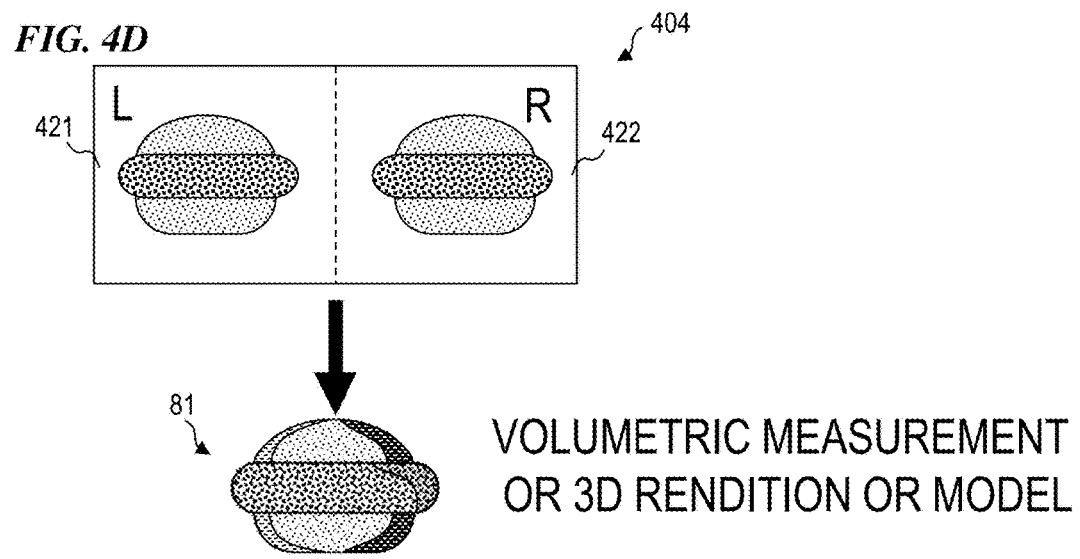
VOLUMETRIC MEASUREMENT OR 3D RENDITION OR MODEL

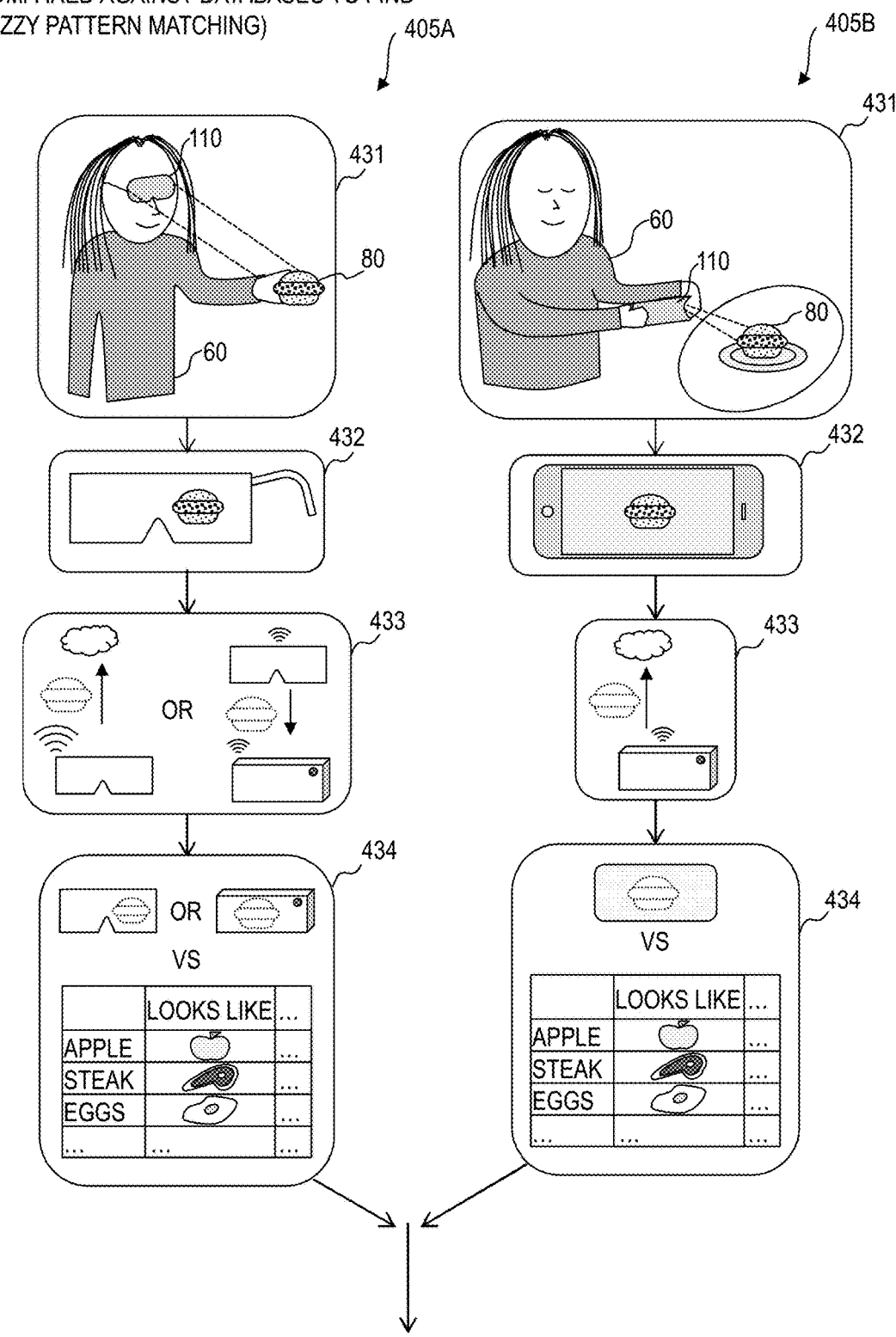
FIG. 4E1
IMAGES COMPARED AGAINST DATABASES TO FIND MATCH (FUZZY PATTERN MATCHING)

*FIG. 4E2*
IMAGES COMPARED AGAINST DATABASES TO FIND MATCH (FUZZY PATTERN MATCHING)
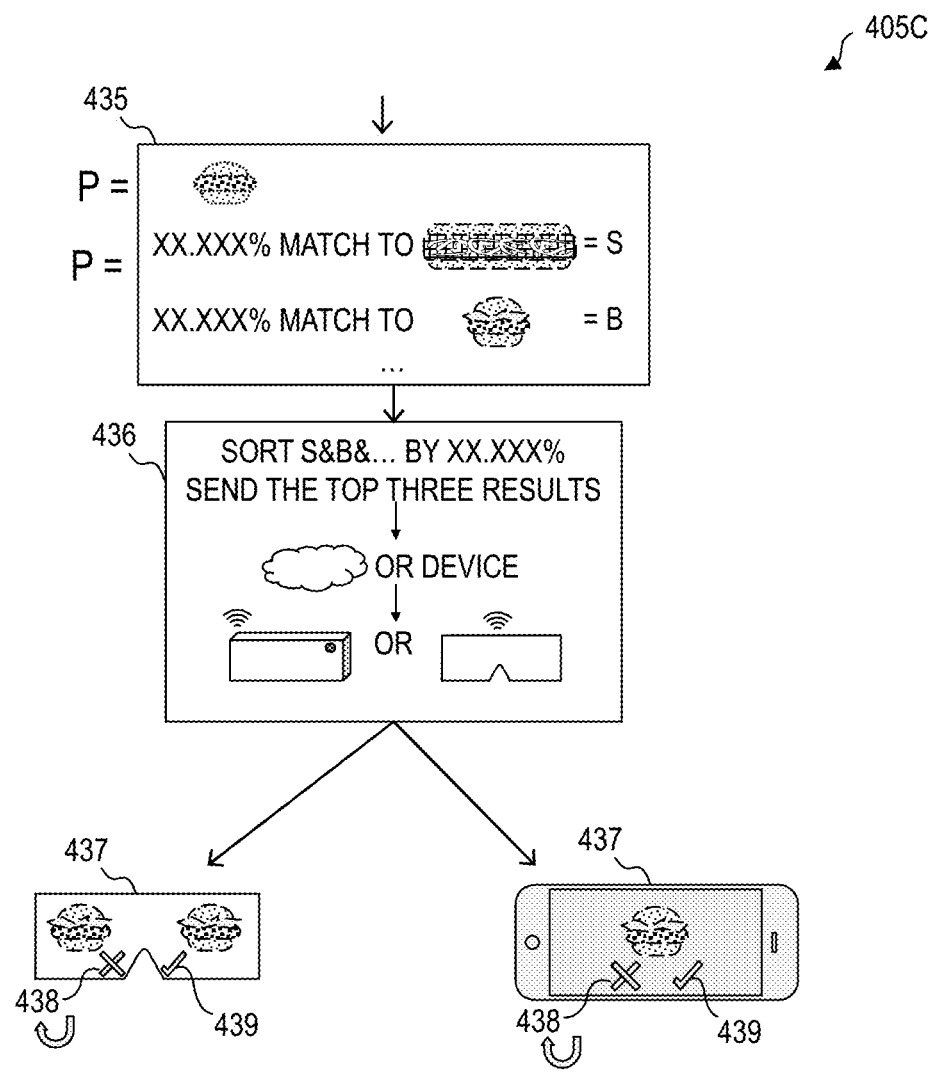

IMAGE REPRESENTATION OF RAMAN SCATTERING OR FLUORESCENCE OF THE FOOD ITEM

CODES/READING ENCODED LABELS, AND/OR OCR OF ALPHABETIC LABELS, WIRELESS, RFID TAGS, NFC

Scan Me

QR CODES

LOGOS

INGREDIENT LISTS

FAR-IR/THERMAL SENSOR PERIPHERAL
(BOLOMETRIC SENSOR)

FLIR OR SEEK-TYPE
BOLOMETRIC SENSOR
(PLUG-ON OR BUILT IN)

SCENT SENSOR AS PLUG-IN PERIPHERAL OR BUILT-IN MULTIFUNCTION SENSOR

OBJECT ISOLATION WITHIN IMAGE

| LP1 | LP2 | LP3 | LP4 | LP5 |
|-----|-----|-----|-----|-----|
|     |     |     |     |     |
|     |     |     |     |     |
|     |     |     |     |     |
|     |     |     |     |     |
|     |     |     |     |     |
|     |     |     |     |     |
|     |     |     |     |     |
|     |     |     |     |     |
|     |     |     |     |     |

FEATURE NUMBER:

1) IDENT ALLERGENS FROM IMAGE OR RAMAN, AMOUNT BY VOL
2) IDENT, COMPUTE, ALLERGENS, FOOD INFO FROM USER, ISOLATE ITEM FROM BG, OCR
3) MEASURE OR ESTIM. VOLUME
4) COMPARE AGAINST DB
5) PROXIMATE BY INGREDIENT
6) INGREDIENTS, NONFOOD, MEDICINES, HORMONES
7) IDENT BY CROWD
8) RFID
9) CALCULATE CALORIES FROM VOL
10) CALORIES FROM GUESSED VOL
11) IDENT UNWANTED, DELETERIOUS EFFECTS
12) IDENT SUBSTITUTES
13) SHOW DIFF IDENTICAL ITEM
14) IDENT NON-BIO ALLERGENS
15) IDENT CHEMICALS
16) IDENT ECO IMPACT
17) IDENT FIRMS
18) ENDANGERED SPECIES
19) REGIONAL HUMAN ISSUES
20) REGIONAL HUMAN ISSUES
21) GMO
22) IMPACT BASELINE HEALTH
23) MULTI SPECTRUM
24) SONOGRAPHY
25) SPECTROSCOPY
26) MULTI IMAGE DIFFERENTIAL
27) OCEAN/ECO EFFECT
28) FRESHNESS
29) IDENT ADDITIVES
30) DELICIOUSNESS
31) CW/MW
32) FIRE OF LIFE
33) IS FOOD REALLY THE FOOD
34) AGE OF FOOD
35) AGE OF PICKING
36) TOTAL TRAVEL FROM ORIGIN
37) LEVEL OF PROCESSING (LP)
38) LOCAL VS NATIONAL GROWN

FEATURE NUMBER:

39) HEAVY METALS
40) INDUSTRIAL CALORIES, ART SWEET, TYPES
41) SODIUM
42) METALS
43) TOXIC METALS/ ORGANIC-TOXINS
44) NEONICOTINOIDS
45) CHILD LABOR
46) BONDED LABOR
47) DIFF ITEMS' OPINION
48) DELICIOUSNESS, FLAVORINGS
49) MSG/HORMONES
50) USER LOCATION
51) PACKAGING
52) FILLERS
53) TBA
54) USER INFO
55) DB OF GROUPS
56) BEST-BY-DATE DATA
57) INTERNET OF THINGS
58) IDENT FLAV BY FDA
59) IDENT FLAV BY INGRED
60) MED INTERACTIONS
61) DETECT CHANGES IN USER'S MENTAL/ PHYSICAL WELLBEING
62) BALANCE OF CALORIES, CLOCK AND ACTIVITIES
63) IDENTIFIED ENVIRON. PRESSURES
64) IDENT CENTRALIZED DB
65) IDENT BY ON-DEVICE DB
66) EXTERN DB/INTERN DB/ CROWD-SOURCED DB
67) DB OF POLICIES
68) DB OF GREENHOUSE
69) SPREAD COMPUTING
70) EFFECT ON CHILDREN
71) EFFECT ON ADULTS
72) EFFECT OVER TIME

FEATURE NUMBER:

73) CHART/GRAPH EFFECTS
74) GRAPH INSULIN
75) SUGGEST MEAL TIMES
76) CHART CUMULATIVE EFFECTS
77) TRANSFATS
78) ALTERNATIVE SUGGESTIONS
79) APP SELF UPDATES
80) IDENT WASTE OF FOOD
81) BREASTFEED
82) LP WELLNESS AND HEALTH INDEX (SEE 37)
83) ILLICIT INGREDIENTS
84) HISTORY OF CONTAMINATES
85) REMOTE UPDATE
86) CHECK ALERTS
87) FAT EFFECT
88) ALL FEATURES, BUT FOR PETS AND LIVESTOCK
89) COMPANY/CEO INTERACT
90) INTERNATIONAL LAW
91) HOSTILE ORGANIZATIONS
92) GLOBAL ECOLOGY
93) EFFECT ON USER'S AGING
94) WHAT TO BUY, WHEN TO BUY
95) GLOBAL ECON EFFECTS
96) INDEX ON RIGHTS
97) WASTEFUL PACKAGING
98) TABLE OF INFORMATION
99) COMBINATIONS:

A) VOLUME: 3,9,10
   B) BIO-ALLERGEN: 1,2
   C) NONBIOALERGEN:14
   D) SPECTRO: 23,25,26
   E) SONO: 24,
   F) LOCATION:50, 63

APPARATUS AND METHOD FOR INFORMED PERSONAL WELL-BEING DECISION MAKING

CROSS-REFERENCE TO RELATED APPLICATIONS

This application claims priority benefit, under 35 U.S.C. § 119(e), of U.S. Provisional Patent Application No. 62/208,570, filed Aug. 21, 2015 by Fazal Wala et al., titled "APPARATUS AND METHOD FOR INFORMED PERSONAL WELL-BEING DECISION MAKING," and U.S. Provisional Patent Application No. 62/208,574, filed Aug. 21, 2015 by Fazal Wala et al., titled "METHOD AND APPARATUS FOR INFORMED PERSONAL WELL-BEING DECISION MAKING," each of which is incorporated herein by reference in its entirety.

FIELD OF THE INVENTION

This invention relates to the field of human (and/or animal) health and well-being and more particularly to a system that includes a personal computing device (PCD), along with an associated remote server system, and the associated method used to evaluate a consumable (items and ingredients consumed for food, used as cosmetics (skin, eye and body care) or the like), wherein the system provides information, signals and/or alerts to facilitate the users to lead healthier lives; the system elicits and receives information within the user's PCD and/or from the associated remote server system regarding source, use, ingredients, attributes and resulting health effects of consuming such food and cosmetic items on the particular user or a population of users in an identified group of users; in some embodiments, the apparatus predicts and displays information regarding, for example, food age, allergen type and its presence, age-spot-causing food components, country source, and certain targeted biochemical contents, and the like, customized for the particular user, as well as outputting identified alternative consumables that are predicted to provide better cost-benefit results, improved metabolic health outcomes; some embodiments further determine a MIL (Movement in Life) score related to the user's rate of calorie expenditure based on their amounts and intensity of physical movement and rest; some embodiments further determine a FIT (Food Information Technology) and FAT (Food-to-Aging Trajectory) score for food consumables that helps categorize foods to be consumed based on the food's health or non-health attributes as determined using expert-provided peer-reviewed and evidence-based data, and based on the user's MIL score.

BACKGROUND OF THE INVENTION

There is evidence-based recognition in the scientific, health and research communities that the quality and quantity of food, food supplements, water and other items consumed for health, family enjoyment, life sustenance, and for growth and health purposes have a major impact on health, happiness and aging outcomes (positive, negative, and neutral). Food impacts many life-and-health quality-outcome attributes and the lifespan of an individual human (or animal), including their offspring's health at birth, their speed-of-onset of puberty, their life quality during adulthood, their general healthful aging and their health-related diseases. Examples of health-related diseases and food-triggered ailments include certain deficiencies, such as rickets due to Vitamin-D deficiency or foods that, on regular and repeated consumption, incite early onset diabetes, early onset age spots (skin discolorations), atherosclerosis (narrowing of arteries), urinary calculi (kidney stones), goiter, higher body-mass index (BMI), gastrointestinal, skin, and/or mental health.

In most life forms (animals, human, etc.), it is generally accepted that richer diets (foods having higher-than-adequate calories, or furnish excessive glycemic calories per meal as a percentage of daily or weekly needs) consumed on a daily or regular basis accelerate the person's speed of aging and maturation (wherein maturation is defined as the point or age at which the animal's or human's form reaches a plateau in growth or maximum size), and the "growth point of inflection" (i.e., the point or age at which growth rate (e.g., per day) is maximum after which there is gradual decay in growth rate).

U.S. Pat. No. 8,166,026 to Sadler issued on Apr. 24, 2012 with the title "User-centric, user-weighted method and apparatus for improving relevance and analysis of information sharing and searching," and is incorporated herein by reference. In this patent, Sadler describes a system and method that enables the user to search and identify meaningful and relevant information, based upon the weighted, custom parameters provided by the user and parameters or rules defined by the community of users as a group, with the option of utilizing user profile information to tune or detune searching, comparing or contrasting, and predicting.

U.S. Pat. No. 7,496,228 to Landwehr, et al. issued on Feb. 24, 2009 with the title "Method and system for detecting and classifying objects in images, such as insects and other arthropods," and is incorporated herein by reference. U.S. Pat. No. 7,496,228, which is referenced by Landwehr et al., is also incorporated herein by reference. In U.S. Pat. No. 7,496,228, Landwehr et al. describe a color-based imaging system and method for the detection and classification of insects and other arthropods are described, including devices for counting arthropods and providing taxonomic capabilities useful for pest-management. Some embodiments include an image sensor (for example, a digital color camera, scanner or a video camera) with optional illumination that communicates with a computer system. Some embodiments include a color scanner connected to a computer. Sampled arthropods are put on a scanner to be counted and identified. The computer captures images from the scanner, adjusts scanner settings, and processes the acquired images to detect and identify the arthropods.

U.S. Pat. No. 5,668,718 to Jinkui Liu, et al. issued on Sep. 16, 1997 with the title "Generating growth alternatives," and is incorporated herein by reference. U.S. Pat. No. 5,668,718 describe an apparatus and method for determining when a living animal (e.g., poultry) reaches its optimum rate of growth. This information is then used to calculate the optimal parameters for achieving the maximum return on investment. The computer determines the optimal number of birds for a flock, type and amount of feed, length of time between hatching and sale to food processor, etc.

With this general understanding of the basic and fundamental food and growth related knowledge, consumers and shoppers can be assisted via smart phones, computers and wearables such as MoveEye™ (e.g., see U.S. Pat. No. 9,250,746 to Shafa Wala, which issued on Feb. 2, 2016 and which is incorporated herein by reference) and other computing device food applications ("apps" loaded onto their smartphones or other personal computing devices) that use embedded evidence-based methods that offer insights into food attributes about to be purchased for family household use, personal use, retail, or for use by their pets, backyard farms or animals at zoos by zoo personnel.

The globalization and digitization of markets and the heavy economic emphasis on food procurement costs has enabled firms to procure foods thousands of miles from where the food is sold or consumed. This new way of global trade across thousands of miles inherently requires foods be treated and augmented by a plethora of methods, packaging and chemicals to preserve their wholesomeness properties, flavor, color, optics, mitigate bacteria or other similar infestations, and diminish perishability and food quality. Some consumers may not desire to eat foods frozen for days during transit or months in a freezer, or would like to learn of food origin source so they are "in the know" (i.e., informed) about what is being ingested and going into their bodies.

U.S. Pat. No. 6,076,043 titled "Utilization effectiveness of nutrients in a population" issued Jun. 13, 2000 to Jinkui Liu is incorporated herein by reference. This patent provides a method and apparatus to model the impact of consumable items on growth and nutrient and weight accretion based on concentration of components (calories)/nutrients in consumable once item is consumed and the accretion dependent upon age and other biofactors.

U.S. Pat. No. 6,115,692 titled "Generating growth alternatives" issued Sep. 5, 2000 to Jinkui Liu et al., and is incorporated herein by reference. In this patent, Jinkui Liu et al. describe an apparatus and method for determining when a living animal reaches its optimum rate of growth, including growth-result properties of food and nutrient intakes as a function of different living and environmental factors.

U.S. Pat. No. 8,055,599 to Werth issued Nov. 8, 2011 with the title "Pattern recognition using cycles or traces in an associative pattern memory (APM), vertical sensors, amplitude sampling, adjacent hashes and fuzzy hashes," and is incorporated herein by reference. In U.S. Pat. No. 8,055,599, Werth describes pattern recognition based on associative pattern memory (APM) and properties of cycles generated by finite cellular automata. APM addresses (e.g., positions in a two-dimensional array) represent states. Cycles are repeating sequences of addresses. Each state is mapped to a "randomly" selected region within the input pattern. Each feature extracted from this region determines one of many next states. All next states (one for each feature type) and all sampled regions are assigned to each state randomly upon APM initialization. The process progresses from state to state, sampling regions of the pattern until the state-transition sequence repeats (generates a cycle). Each feature pattern is represented by one cycle; however, different cycles can be derived from one pattern depending on the initial state. Some embodiments use a refractory period assuring a minimum cycle length, making it likely that any given pattern yields only one cycle independent of the initial state.

Example of prior-art methods to determine linear and/or volume measurements of objects include the following:

U.S. Pat. No. 8,897,539 to Stone, et al. issued on Nov. 25, 2014 with the title "Using images to create measurements of structures through the videogrammetric process," and is incorporated herein by reference. This patent describes according to various embodiments, a stream of image frames depicting a structure in a scene are obtained. The stream of image frames may comprise first image frames from a first imaging device and second image frames from a second imaging device. Using the first image frames and the second image frames, a wireframe of at least a portion of the structure is generated. From the wireframe, as-built dimensions may be identified, materials estimates may be determined, and/or data for a fabrication device may be generated, for example.

U.S. Pat. No. 8,855,406 to Lim, et al. issued on Oct. 7, 2014 with the title "Egomotion using assorted features," and is incorporated herein by reference. This patent describes a system and method are disclosed for estimating camera motion of a visual input scene using points and lines detected in the visual input scene. The system includes a camera server comprising a stereo pair of calibrated cameras, a feature processing module, a trifocal motion estimation module and an optional adjustment module. The stereo pair of the calibrated cameras and its corresponding stereo pair of camera after camera motion form a first and a second trifocal tensor. The feature processing module is configured to detect points and lines in the visual input data comprising a plurality of image frames. The feature processing module is further configured to find point correspondence between detected points and line correspondence between detected lines in different views. The trifocal motion estimation module is configured to estimate the camera motion using the detected points and lines associated with the first and the second trifocal tensor.

U.S. Pat. No. 8,953,024 to Wang, et al. issued on Feb. 10, 2015 with the title "3D scene model from collection of images," and is incorporated herein by reference. The patent provides a method for determining a three-dimensional model of a scene from a collection of digital images, wherein the collection includes a plurality of digital images captured from a variety of camera positions. A set of the digital images from the collection are selected, wherein each digital image contains overlapping scene content with at least one other digital image in the set of digital images, and wherein the set of digital images overlap to cover a contiguous portion of the scene. Pairs of digital images from the set of digital images to determine a camera position for each digital image. A set of target camera positions is determined to provide a set of target digital images having at least a target level of overlapping scene content. The target digital images are analyzed using a three-dimensional reconstruction process to determine a three-dimensional model of the scene.

PCT Publication No. WO2013/173383 by Brilakis et al. published Nov. 21, 2013 titled "Methods and apparatus for processing image streams," and is incorporated herein by reference. PCT Publication No. WO2013/173383 describes apparatus and related methods for obtaining 3-dimensional spatial data associated with civil infrastructure. The method includes obtaining a stereo videogrammetric video, via a first and second video camera. The video includes a first plurality of video frames of the infrastructure. The method further includes calibrating the first and second video camera. The method also includes detecting a second plurality of features of the infrastructure selected from the group consisting of lines, points, and planes of the infrastructure in a third plurality of video frames from the first plurality of video frames of the infrastructure. The method further includes matching the second plurality of detected features of the infrastructure in the third plurality of video frames.

PCT Publication WO2008/074340 by Karkkainen is titled "Mobile apparatus with smell, biological or DNA sensor and method for location and identification" and is incorporated herein by reference. This publication describes a mobile electronic apparatus with a smell sensor and/or a biological sensor and/or a DNA sensor. The mobile apparatus is configured to identify smells, smell tags, biological tags and/or DNA tags for finding or identifying objects that are provided with said tags.

U.S. Pat. No. 6,858,182 to Ito, et al. issued on Feb. 22, 2005 with the title "Exhalation gaseous component gauge and a cellular phone equipped with function of measuring gaseous components", and is incorporated herein by reference. This patent describes an exhalation gaseous component gauge including, in a palm-sized casing having exhalation taking-in and taking-out slots made on its front and rear sides, a semiconductor gas sensor so placed that the air flowing from one's mouth may pass the sensor, a CPU responsive to the signal from the sensor for determining the quantity of the exhalation gaseous components, and a display for showing the so determined result. The palm-sized casing is so sized and configured as to permit one to have a look at the display while holding the gauge in hand to direct the air from the mouth to the exhalation taking-in slot. Also, disclosed is a cellular phone equipped with an exhalation gaseous component gauge.

U.S. Pat. No. 9,250,746 issued to Shafa Wala on Feb. 2, 2016 with the title "Position capture input apparatus, system, and method therefor", and is incorporated herein by reference. U.S. Pat. No. 9,250,746 describes an input system that uses a camera to capture an image of a displayed graphical user interface that may be partially obstructed by an object, such as a user's hand or other body part. The position-capture input system also includes a software component that causes a computing device to compare the captured image with a displayed image to determine which portion, if any, of the graphical user interface is obstructed. The computing device can then identify any user interface elements with which the user is attempting to interact. The position-capture input system may also include an accelerometer or accelerometers for detecting gestures performed by the user to, for example, select or otherwise interact with a user-interface element. The position-capture input system may also include a haptic feedback module to provide confirmation, for example, that a user-interface element has been selected.

U.S. Pat. No. 5,478,989 to Shepley issued on Dec. 26, 1995 with the title "Nutritional information system for shoppers," and U.S. Pat. No. 5,841,115 to Shepley issued on Nov. 24, 1998 with the title "Nutritional Information System for Shoppers" and each is incorporated herein by reference. U.S. Pat. Nos. 5,478,989 and 5,841,115 describe a method for providing personalized nutrition information to an individual comprising the following steps: (a) inputting personal data relating to an individual; (b) inputting data identifying at least one food product which the individual intends to purchase or consume; (c) accessing pre-stored information relating to the at least one food product which the individual intends to purchase or consume; (d) generating and outputting information about the at least one food product which the individual intends to purchase or consume pertinent to the input personal data.

U.S. Pat. No. 6,024,281 issued to Shepley on Feb. 15, 2000 with the title "Nutritional information system for shoppers", and is incorporated herein by reference. U.S. Pat. No. 6,024,281 describes a method for providing personalized nutrition information to an individual comprising the following steps: (a) inputting personal data relating to an individual; (b) inputting data identifying at least one food product which the individual intends to purchase or consume; (c) accessing pre-stored information relating to the at least one food product which the individual intends to purchase or consume; (d) generating and outputting information about the at least one food product which the individual intends to purchase or consume pertinent to the input personal data.

U.S. Pat. No. 6,232,602 to Kerr issued on May 15, 2001 with the title "Enhanced vision system sensitive to infrared radiation," and is incorporated herein by reference. U.S. Pat. No. 6,232,602 describes an enhanced vision system and method for use with vision systems with an imager sensitive to infrared radiation of less than 2-microns in wavelength, to produce a first image signal. Another imager sensitive to infrared radiation at least 3-microns in wavelength may be used to produce a second image signal. Preferably, the first image signal represents sensed electric light sources, and the second image signal represents sensed background such as terrain, runways, structures, and obstacles. A signal processor combines an image signal representing locally maximum values of the first image signal with the second image signal to create a displayed image.

U.S. Pat. No. 9,065,254 to Geske et al. issued on Jun. 23, 2015 with the title "Multi-wavelength VCSEL array to reduce speckle," and is incorporated herein by reference. U.S. Pat. No. 9,065,254 describes an illuminator having a light source to originate an illumination beam, wherein the light source further comprises a set of vertical-cavity surface emitting lasers (VCSELs), including a first VCSEL having a first laser emission wavelength, and a second VCSEL having a second laser emission wavelength different than the first laser emission wavelength. Thus, by varying laser emission wavelengths of VCSELs in a VCSEL array, embodiments of the invention produce low-contrast speckle, and do not limit the imaging capabilities of the host illumination system. In some embodiments of the invention, vertical external cavity surface emitting lasers (VECSELs) are utilized to produce the above described varying laser emission wavelengths.

U.S. Pat. No. 6,095,949 to Arai issued on Aug. 1, 2000 with the title "Health management device", and is incorporated herein by reference. U.S. Pat. No. 6,095,949 describes a health management device that includes an exercise quantity measurer for measuring a quantity of exercise; an intake calorie calculator for calculating an intake calorie on the basis of input information of meal including the types and quantities of foods; a consumption calorie calculator for calculating, on the basis of the information of a quantity of exercise measured by the exercise quantity measurer, a calorie consumed by the exercise; a calorie balance analyzer for analyzing a calorie balance on the basis of the calculation results of the intake calorie and the consumption calorie; a diet effect simulator for simulating a diet effect on the basis of the information of the analyzed calorie balance and personal information; and a moving image display controller for changing a display character to display the diet effect with a moving image.

U.S. Patent Publication US 2014/0214618 by Pedley et al. published on Jul. 31, 2014 with the title "IN-STORE CUSTOMER SCAN PROCESS INCLUDING NUTRITIONAL INFORMATION", and is incorporated herein by reference. Pedley et al. describe a computer-implemented process can be implemented to provide a customer with nutritional information about an item to be purchased. The process includes monitoring a scan of the item to be purchased within a processor of a portable computerized device. The process further includes automatically referencing a remote database to identify nutritional information for the item to be purchased and displaying the nutritional information to the customer upon a display of the portable computerized device.

U.S. Patent Publication 2008/0172244 of Coupal et al. titled "Systems and Methods for Displaying Current Prices, Including Hotel Room Rental Rates, With Markers Simultaneously on a Map" is incorporated herein by reference. Publication 2008/0172244 discloses systems and methods for displaying current prices of goods or services provided at a plurality of locations within a geographical area. In an embodiment, their system includes a computer terminal, a map server, an information source, a set of map markers, and a web server. In another embodiment, a method includes specifying the geographical area by an input of data, providing a map of the geographical area to a computer terminal, sending a query to an information source, matching map markers indicating specific prices to the current prices for selected one's goods or services, and relaying the map markers to the computer terminal, and overlaying the map markers onto the map so as to display current prices simultaneously for each of the plurality of locations. Other embodiments are also disclosed.

U.S. Pat. No. 8,690,578 to Nusbaum et al. issued on Apr. 8, 2014 with the title "Mobile Computing Weight, Diet, Nutrition, and Exercise Management System with Enhanced Feed Back and Data Acquisition Functionality" and is incorporated herein by reference. This patent describes an illustrative mobile computing device executing weight, nutrition, health, behavior and exercise application software serves as a simulated combination personal trainer and dietician/nutritionist for the user using comprehensive databases storing personalized health, nutrition and exercise information. A mobile computing device, such as a smartphone, executing such software monitors, tracks and/or adjusts caloric intake, energy expenditure taking into account nutritional information and behavioral factors. The mobile computing device receives food consumption, exercise-related, behavior and other input using speech input and the device's GPS subsystem to ease data entry burden on users and to promote continued long-term usage. The system rewards user goal achievement in an automatic, seamless manner, through, for example, downloading music, books, or other media. In illustrative implementations, the system assists users to make healthy food and exercise choices by using a comprehensive color code system to identify good choices, bad choices and those in between.

U.S. Pat. No. 8,788,448 to Fadell et al. issued on Jul. 22, 2014 with the title "Occupancy pattern detection, estimation and prediction," and is incorporated herein by reference. U.S. Pat. No. 8,788,448 describes systems and methods for predicting and/or detecting occupancy of an enclosure, such as a dwelling or other building, which can be used for a number of applications. An a priori stochastic model of occupancy patterns based on information of the enclosure and/or the expected occupants of the enclosure is used to pre-seed an occupancy prediction engine. Along with data from an occupancy sensor, the occupancy prediction engine predicts future occupancy of the enclosure. Various systems and methods for detecting occupancy of an enclosure, such as a dwelling, are also described.

U.S. Pat. No. 8,594,850 to Gourlay et al. issued on Nov. 26, 2013 with the title "Updating control software on a network-connected HVAC controller," and is incorporated herein by reference. U.S. Pat. No. 8,594,850 describes providing software updates to client devices. A client device (such as a thermostat) executes software to perform one or more functionalities of the device. Upon receiving an indicating that a software update is available, the device waits to download the software update until pre-download conditions are satisfied. Once the software update is downloaded, the device then waits to install the software update until pre-install conditions are satisfied. If the software update is non-critical and received during an initial installation of the device, the software update may not be installed until after installation of the device is complete. If the device is a thermostat, the device may delay installation of the software update until a controlled HVAC system in inactive. Control of the HVAC system may be disabled during installation of the software update.

U.S. Pat. No. 8,478,447 to Fadell et al. issued on Jul. 2, 2013 with the title "Computational load distribution in a climate control system having plural sensing microsystems" and is incorporated herein by reference. U.S. Pat. No. 8,478,447 describes controlling one or more HVAC systems using a distributed arrangement of wirelessly connected sensing microsystems are described. A plurality of wirelessly communicating sensing microsystems is provided, each sensing microsystem including a temperature sensor and a processor, at least one of the sensing microsystems being coupled to an HVAC unit for control thereof. The plurality of sensing microsystems is configured to jointly carry out at least one shared computational task associated with control of the HVAC unit. Each sensing microsystem includes a power management circuit configured to determine an amount of electrical power available for dedication to the at least one shared computational task. The at least one shared computational task is apportioned among respective ones of the plurality of sensing microsystems according to the amount of electrical power determined to be available for dedication thereto at each respective sensing microsystem.

U.S. Pat. No. 9,212,996 to Watson et al. issued on Dec. 15, 2015 with the title "Analyzing and correlating spectra, identifying samples and their ingredients, and displaying related personalized information," and is incorporated herein by reference. U.S. Pat. No. 9,212,996 describes obtaining two spectra from the same sample under two different conditions at about the same time for comparison, where at least one of the spectra measures magnitudes of electromagnetic radiation on at least four different ranges or weightings of wavelengths or frequencies. Classifying a sample using these spectra obtained by a user, and using spectra obtained from different samples by different users to identify the sample. Computing correlations between data related to food and ingredient consumption by one or more users over time, and data related to passive personal log data, user entered feedback, user interaction data or personal information related to those users, and detecting: foods or ingredients to which a user may be allergic or intolerant; a possible medical condition of a user; a possible link between food and ingredient consumption and a medical or health condition; or a similarity between at least two such users.

U.S. Pat. No. 9,291,504 to Goldring et al. issued on Mar. 22, 2016 with the title "Spectrometry system with decreased light path," and is incorporated herein by reference. U.S. Pat. No. 9,291,504 describes a spectrometer comprises a plurality of isolated optical channels comprising a plurality of isolated optical paths. The isolated optical paths decrease cross-talk among the optical paths and allow the spectrometer to have a decreased length with increased resolution. In many embodiments, the isolated optical paths comprise isolated parallel optical paths that allow the length of the device to be decreased substantially. In many embodiments, each isolated optical path extends from a filter of a filter array, through a lens of a lens array, through a channel of a support array, to a region of a sensor array. Each region of the sensor array comprises a plurality of sensor elements in which a location of the sensor element corresponds to the wavelength of light received based on an angle of light received at the location, the focal length of the lens and the central wavelength of the filter.

An article by Colman et al. titled "Caloric restriction reduces age-related and all-cause mortality in rhesus monkeys" (www.nature.com/articles/ncomms4557, Nature Communications 5, Article number: 3557 (2014) doi: 10.1038/ncomms4557) is incorporated herein by reference. In this article, Colman et al. write: "Caloric restriction (CR) without malnutrition increases longevity and delays the onset of age-associated disorders in short-lived species, from unicellular organisms to laboratory mice and rats. The value of CR as a tool to understand human ageing relies on translatability of CR's effects in primates. Here we show that CR significantly improves age-related and all-cause survival in monkeys on a long-term ~30% restricted diet since young adulthood. These data contrast with observations in the 2012 NIA intramural study report, where a difference in survival was not detected between control-fed and CR monkeys. A comparison of body weight of control animals from both studies with each other, and against data collected in a multi-centered relational database of primate ageing, suggests that the NIA control monkeys were effectively undergoing CR." The report and data indicate that the benefits of CR on ageing are conserved in primates.

An article by Ramsey et al. titled "Dietary restriction and aging in rhesus monkeys: the University of Wisconsin study" (www.ncbi.nlm.nih.gov/pubmed/11113597, Exp Gerontol. 2000 December; 35(9-10):1131-49) is incorporated herein by reference. In this article, Ramsey et al. write: "Dietary restriction (DR) retards aging and extends the maximum lifespan of laboratory mice and rats. To determine whether DR has similar actions in a primate species, we initiated a study in 1989 to investigate the effects of a 30% DR in 30 adult male rhesus monkeys. In 1994, an additional 30 females and 16 males were added to the study. Although the animals are still middle-aged, a few differences have developed between the control and DR animals suggesting that DR may induce physiologic changes in the rhesus monkey similar to those observed in rodents. Fasting basal insulin and glucose concentrations are lower in DR compared to control animals while insulin sensitivity is higher in the restricted animals. DR has also altered circulating LDL in a manner that may inhibit atherogenesis. These results suggest that DR may be slowing some age-related physiologic changes. In addition to measures of glucose and lipid metabolism, the animals are evaluated annually for body composition, energy expenditure, physical activity, hematologic indices, and blood or urinary hormone concentrations. In the next few years, the first animals will reach the average lifespan (approximately 26 years) of captive rhesus monkeys and it will become possible to determine if DR retards the aging process and extends the lifespan in a primate species."

What is needed is an improved food-assessment method and apparatus for purchase and health recommendations and notices.

SUMMARY OF THE INVENTION

The present invention provides an apparatus, method and process that elicits and receives inputs from various sources, and calculates and displays customized outputs for a particular user or a specified population of users to help that user make better-informed and evidence-based decisions as to what to eat or avoid to improve their well-being, personal food economics, happiness, longevity, as well as sexual, mental and general health. This provides to a particular human user with immediate information, focusing on health and wellness, on items the user chooses for possible consumption. The articles referenced above provide a basis and evidence that food consumed is an important and significant life variable that impacts health, happiness and longevity in humans and animals, knowing this fact in the back on one's mind is much less helpful than having a device of the present invention that provides the user with instant feedback regarding a consumable that the user is contemplating purchasing and or consumption. By using data captured by a personal handheld computing device (such as a smartphone) for example, data from a plurality of sensors such as a captured optical image and spectrum, sound and/or ultrasonic imaging, odor, chemical, electrical conductivity, pH (acidity or alkalinity), and other various input sensors, as well as communications with databases in an internet-connected computer server system and IOT devices ("internet of things" devices such as refrigerators and cupboard food shelves) that identify food types and ingredients and track or determine the effects on the health and well-being of various types of human users as well as historical data from prior user inputs from the particular human user, some embodiments of the present invention identify items and their probable or possible components. By using user input, GPS (global positioning system), geographically local conditions and alerts, some embodiments of the present invention determine and present information specific to the user and the geographic location and environment occupied by the user. By using established databases and augmenting such databases, and by creating new computer-automated machine-learning and knowledge databases, some embodiments of the present invention compile, compare, transmit and store data on various food, supplements and/or cosmetics consumables.

In some embodiments, the system of present invention includes one or more of the human user's personal computing devices (PCDs) (such as, for example, a smartphone, Apple Watch®, FitBit®, iPad®, Google Glass®, other "wearables," and the like), optionally includes their personal home computer system that has a plurality of appliances (such as a refrigerator) and other devices each having wireless communications connected as an internet of things (IOT), and a central database server system (which includes one or more computers connected to one another and the internet). In some embodiments, the system of present invention obtains and stores, for each human user, identifying information as to each of the consumables that user has purchased and when each of these were purchased. The system further obtains information, warnings and recalls from the United States FDA (Food and Drug Administration) and other government and non-governmental agencies, as well as manufacturers, suppliers, and transportation companies. In some embodiments, the system then correlates the information, warnings and recalls with the products and ingredients in the consumables of each user that has been identified and stored for that particular user, and filters the information to just the affected consumables such that when a warning or recall has been issued that affects a consumable of that particular user, the system automatically (i.e., without any inquiry or prompting by the user) activates that user's PCD(s) and/or their IOT appliance(s) such that the PCD(s) and/or their IOT appliance(s) alert the user (for example, by lights flashing, specific sounds, or haptic vibrations) as to the nature of the warning and as to the exact consumable affected.

Some embodiments of the present invention elicit and receive, from the user and the user's personal computing device(s), the user's profile information, which includes such data as the user's height, weight, age, ethnic heritage, residence location (e.g., the user's home and/or at the current GPS coordinates), allergies, pre-dispositions to certain health problems, body-mass index (BMI), high-density and low-density lipoprotein cholesterol, total cholesterol, c-reactive proteins, certain targeted protein markers (e.g., prostate-specific antigens and brain proteins, blood pressure, blood-sugar levels, base-line health, and the like. Some embodiments of the present invention elicit and receive into the user's profile information a history of every food item that the user has purchased and/or consumed, in order to modify the calculations of what additional foods the user should consume or avoid.

In some embodiments the personal computer device of the user elicits and receives the user's activity information as to what the user is doing, for example sitting on a couch watching television, walking on a treadmill, taking an online educational class, riding a bike, playing soccer, eating watermelon and grapes versus eating a hotdog wrapped in bacon and peanut butter, smoking or the like. In some embodiments, the personal computing device tracks and accumulates this activity information into the user's profile information and uses this activity information to calculate a MIL (Movement in Life) score with calories expended in state of rest and mobility. In some embodiments, the user's activity information and the MIL score are stored as part of the user's profile information.

In some embodiments, the present invention elicits and receives information from government agencies (e.g., the FDC, USDA, CDC of the U.S., or agencies of other nations) as well as from private companies, universities and institutions regarding the calorie and nutrition needs of persons having certain personal characteristics, as well as the calorie and nutrition characteristics of various consumable items. In some embodiments, this information on caloric and nutrient needs is calculated using the descriptions in U.S. Pat. Nos. 5,668,718 and 6,076,043, both to Jinkui Liu, and both of which are incorporated herein by reference. In some embodiments, this information is stored in a centralized or distributed database, and portions of the information are also transmitted to and stored in certain user's personal computing devices (PCDs).

Some embodiments of the present invention give a user access to information on the consumable items from various companies, producers, manufacturers, and various other components, including travel time and distance, in an item's trip from dirt (earth) to dinner table. Some embodiments of the present invention establish methods and procedures to attempt to ascertain both the point of origin of a consumable, and the route along which it has traveled in its journey to the user. Some embodiments of the present invention use this food-content information, along with the user's profile information to derive and present to the user a "goodness of the food's fit for the user's purpose" that is used to generate "FIT and FAT" score or rating for the specified food in order to give data to the user about the quality of health the consumable item provides (or propensity to cause and accrue better or poorer health). In some embodiments, the user's MIL score (the calories expended by this particular user in state of rest and in a state mobility) is used to customize and calibrate the value of each consumable item to each particular user, and to adjust the weightings used to calculate the FIT and FAT score for the consumable item for that particular user.

In some embodiments, the FIT and FAT scores of all items are tracked (and, in some embodiments, used for an accumulated FIT-and-FAT score from a repository of FIT-and-FAT scores of past purchases in the user's profile information) for the given user. This information is used to also estimate the person's likely longevity, mental or sexual health, or other aspects resulting from the person's activities (accumulated on the user's MIL score) and the items that are consumed over time. For example, the effect on longevity might be a computed estimation of the shortening or lengthening of the expected lifetime by a few seconds or several days or even years.

In the context of human-consumption choices, it is beneficial to have an invention and method that characterizes consumables using methods of the present invention. There are a number of different groups, companies and governmental organizations that bring parts and pieces of information for health of a user, but rarely do they give data on the probable effects on a generic person (i.e., the average human) of an item's consumption, and there is no way for a particular individual with a given genotype and specific attributes to obtain customized information as to the effects (both immediate and cumulative) of a particular food item on that particular person. The ability to discover what chemicals an individual may be sensitive to, even sensitive to in a life-threatening or life-altering way, is still difficult to obtain. While there is much information on what companies do in the larger scale to the environment and workers for many industries, there is not a good source for this information when it comes to foods and their journey from dirt to dinner. The ability to get the overall, long-term and scientifically validated data on the effects on multiple areas of individual and population health and wellness is currently not implemented for humans, even though certain subsets of such data have long been used in animal production. The present invention addresses these and related issues and problems.

BRIEF DESCRIPTION OF THE DRAWINGS

FIG. 1B is a high-level block diagram of a method 102 for identification of a consumable and its condition and ingredients, according to some embodiments of the present invention.

FIG. 2A is a block diagram of a method 201 for alerting a user of late-arriving data that changes a recommendation made earlier by method 101 such that a different recommendation should now be considered, according to some embodiments of the present invention.

FIG. 4A is a schematic diagram of a device 401, such as a handheld, with a pair of cameras to give stereoscopic imaging and sensing, with a small predetermined distance between them to compute things such as volume or creating a 3D image, according to some embodiments of the invention.

FIG. 4B is schematic diagram of a diagram of a wearable device 402, specifically glasses, with a pair of cameras to give stereoscopic imaging and sensing, with a larger predetermined distance between them to compute things such as volume or creating a 3D image, according to some embodiments of the invention.

FIG. 4C is schematic diagram of a device 403 (similar to device 402 as described in FIG. 4B) as an example of a different embodiment for the camera, according to some embodiments of the invention, showing one of many variations of the design.

FIG. 4D is a block diagram of a method 404, wherein stereoscopic imaging takes two (or more) images, and performs calculations to create a 3D model and/or a measurement of the volume of a three-dimensional object, according to some embodiments of the invention.

FIG. 4E1 and FIG. 4E2 together form a block diagram of an example method 405 wherein a captured object is compared against a database of known objects (e.g., a database of reference patterns that is created by training the pattern recognition program with known items, each creating one or more reference patterns for that type of item), in order to identify the object, or one or more of its closest alternatives, according to some embodiments of the invention.

FIG. 17 is a table of features, some or all of which are combined and used in some embodiments of the invention.

DESCRIPTION OF PREFERRED EMBODIMENTS

Figure 1A:
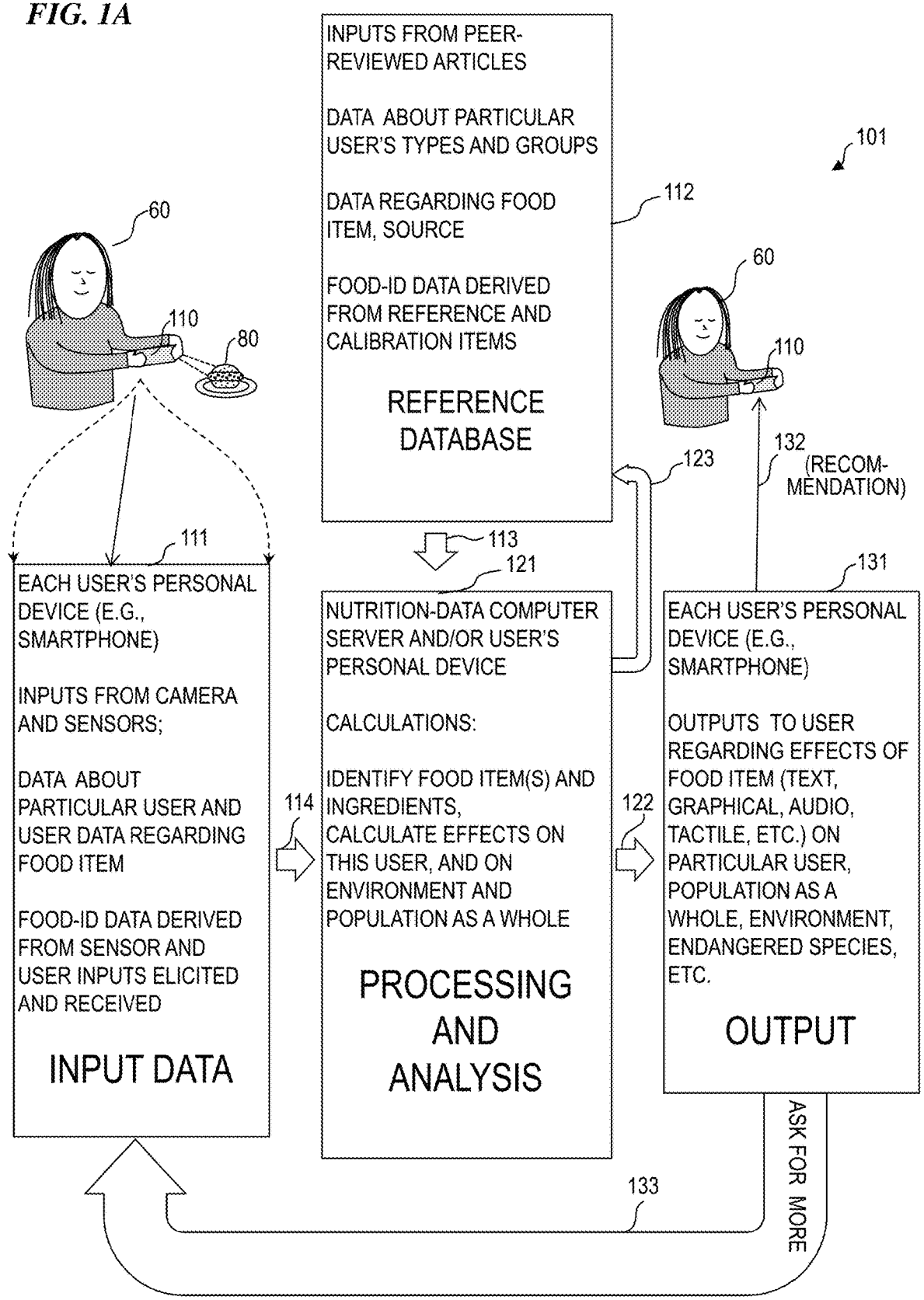
FIG. 1A is a block diagram of a method 101 for assisting a user in informed personal well-being decision making, according to some embodiments of the present invention.

Although the following detailed description contains many specifics for the purpose of illustration, a person of ordinary skill in the art will appreciate that many variations and alterations to the following details are within the scope of the invention. Specific examples are used to illustrate particular embodiments; however, the invention described in the claims is not intended to be limited to only these examples, but rather includes the full scope of the attached claims. Accordingly, the following preferred embodiments of the invention are set forth without any loss of generality to, and without imposing limitations upon the claimed invention. Further, in the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention. The embodiments shown in the Figures and described here may include features that are not included in all specific embodiments. A particular embodiment may include only a subset of all of the features described, or a particular embodiment may include all of the features described.

The leading digit(s) of reference numbers appearing in the Figures generally corresponds to the Figure number in which that component is first introduced, such that the same reference number is used throughout to refer to an identical component which appears in multiple Figures. Signals and connections may be referred to by the same reference number or label, and the actual meaning will be clear from its use in the context of the description.

In various embodiments of the present invention, the user's device and/or a central or distributed knowledge-nutrition-database server performs one or more of the following functions. In some embodiments, the user's personal computing device 1310 (such as, for example, a smartphone, Apple Watch®, FitBit®, iPad® and the like—see FIG. 13A), or internet-of-things (IOT) appliance 1319 (such as, for example, a television, personal computer, a smart refrigerator, microwave oven or home-security system, or the like—see FIG. 13A; any or all of which wirelessly communicate with one another) activates itself and provides an indication output (visual, audio or haptic/tactile) to the user of a consequence or a recommended alternative to consumption of a particular item.

In general, some embodiments of the present invention include evaluating those food items (consumables) for the presence and/or baseline health impact of
  i.) allergens,
  ii.) total concentration and intensity of the allergens in food,
  iii.) impact of the consumable and its portion size on the baseline weight gain,
  iv.) impact of the consumable on the speed (acceleration or deceleration) of aging, and
  v.) general wellness, herein defined by the impact on the well-being of the individual and sub-culture genotype that the individuals belonged population (e.g., Alaskan Eskimos).

To add to the complexity of food choice and lack of evidence and information based methods in consumable purchase decisions are a conundrum of food label definitions acceptable or even provided by various governments and countries around the world. For example, in the USA food labels of foods on the shelves or refrigerators of Walmart and other grocery stores have a plethora of terms on foods that are supposed to provide clarity to shoppers and consumers. Foods labeled, for example, as:
  1.) bread "Made with whole grains or 'Oatnut Bread'" does not necessarily mean the bread contains 100% whole grains or is made with Oatnuts,
  2.) cage-free eggs, does not necessarily mean the birds are roaming freely in sun-drenched ranches,
  3.) Washington natural cherries does not necessarily mean they are from Washington state (in the U.S.) nor are they 100% free of preservatives,
  4.) products labeled as "made with" or "has" (e.g., "Made with pomegranate juice") can have very small traceable amounts of the material advertised as "made with",
  5.) no hormones or GMO (genetically modified foods) only means the item meets the definitions as allowed and registered with the FDA,
  6.) organic meat and poultry does not mean that the food is 100% organic, nor does it mean that the animals were fed only organic feed and supplements certified to be free from non-organic ingredients,
  7.) natural does not mean raised with only natural products, and
  8.) natural flavors, colors and preservatives with such terms as carmine (extract from certain cochineal insects) can be in truth "natural" but perhaps may cause allergic reactions in some people and is not necessarily what the consumer thought was in the food nor what they intended to eat.

Furthermore, "natural" does not necessarily mean that the foods are not allergenic (prone to cause allergies in certain people or segments of a population), toxic, nor necessarily free from pesticides or hormones. In addition, there are various other legally allowed terms such as "Free," "Low," or "Reduced" can be, at best, confusing to consumers, let alone professional shoppers for restaurants or buyers of produce and meat for retailers and governments. The government's objective in labeling is to help buyers and consumers in providing veracity and truthfulness according to the Office of Nutrition and Food Labeling of the United States Food and Drug Administration (FDA).

It is also very difficult for a consumer or a shopper to decipher all the smart and clever terms used to label food and food contents let alone understand the impact of food on one's health and happiness. For example, the term "made with" in the real world can mean made with a lot of a certain ingredient (e.g., "whole grain") or made with very little of that ingredient. The fine print and the printed font size can make it hard for many people, particularly seniors, people with impairments, and aged people with reading difficulties, to decipher these terms and learn what the food really contains to be informed and efficient shoppers. The United States FDA does not have legally binding definitions for terms such as "made with." Even terms such as "gluten free" does not guarantee it is 100% gluten free all the time.

Foods with certain preservatives and packaging when placed and cooked in microwave ovens can create chemical derivatives which when consumed on a regular basis can have health consequences due to the derived chemical's hormetic toxic effects (those resulting from accumulation in the body—"hormesis" is a term used by toxicologists to refer to a biphasic dose response to an environmental agent characterized by a low-dose stimulation or beneficial effect and a high-dose inhibitory or toxic effect).

It is also difficult for an individual to evaluate every food item about to be consumed for that food item's immediate and cumulative effect on the individual's health, happiness and well-being. Different foods and ingredients, even if they superficially appear similar, can have different allergens, and different carbohydrate, fat, and protein content and thus will have different effects on the person's health. For example, foods with identical caloric content but with different sources for its ingredients, which result in the food's calories, can have pronounced short term or long term elevated blood sugar levels which can make an individual more prone to early onset diabetes, as well as putting the person in a state of surplus energy intake and thus in a state of positive body calories energy balance, resulting in higher BMI over time and other health consequences. Further, depending on the user's baseline health, certain consumables have higher propensity to generate more adipose tissue (stored body fat)

or higher muscle-mass deposition depending on the user's MIL index and the point in time on his or her life trajectory. Lack of knowledgeability on food energetics and health outcomes predisposes a consumer to irrational purchases resulting in early-onset diabetes and other long-term health problems.

Persons that have certain allergies (e.g., to peanuts, certain insect extracts, or particular artificial sweeteners) need to (or should) scan the ingredient list on every food item to be consumed to ensure they do not eat something that could cause a severe allergic reaction. An additional difficulty is that an ingredient can be identified by different names by different food producers, or can be lumped under generic terms that lack specific information such as "natural and artificial flavors."

Thus, it is difficult for shoppers and food consumers to identify and keep track of all the components of foods they consume. It is also difficult to perform well-controlled experiments on humans to determine the immediate and cumulative health impacts of various foods and combinations of foods. It is particularly difficult to determine the effects of particular foods on people of differing genotypes (tribes/race, epigenetics, etc.).

In addition to food; non-regulated food (sometimes termed generally recognized as safe (GRAS)), vitamin supplements, feed supplements that were fed to the animal that is now being used as food, enzymes, probiotics, prebiotics and various other food or parenteral (via blood or direct fed into gut and stomach) food supplements, as well as cosmetics and topical ointments and lotions can have good or deleterious health effects. For example, medical researchers at the University of Minnesota are exploring interactions between cancer drugs and dietary supplements (source: Wall Street Journal, Mar. 1, 2016). These researchers have discovered an interaction with an herbal supplement *Echinacea* and a cancer drug. There are many other such antagonistic results with food supplements that interfere with antibiotic therapy or components of the food augmenting the effect of blood thinners or interfering with the potency of antibiotics, blood cholesterol lowering drugs, cancer or mental health management drugs. Herbal supplements when used in small amounts in cooking can augment food aroma and food flavor. When concentrated in pills and capsules, these herbal supplements can still be helpful but may also cause serious side effects in patients consuming other drugs for cancer, or prior to surgery antibiotics or immunity augmenting vitamins.

Given this reality, animal experiments provide one basis (in the absence of large-scale epidemiological trials of food items on human population health) to get proven data and theories that can be extrapolated from animals to humans and recognized in the 'peer-to-peer' scientific community and research communities. At this time, animal experiments are heavily done with regard to the effect of commercial antibiotics, vaccines and other toxins on animals (e.g., in livestock or animals that are generally considered pets) under controlled conditions. This includes the use of animal-growth and toxicity experiments on live animals, as well as the use of animal growth models, metabolic efficiencies by weight and age in computer-simulation computations (growing animals in a virtual computer).

There are a number of conventional public-domain methods, scientific communities, the USDA (United States Department of Agriculture), as well as proprietary systems that can assist consumers via devices and methods that report calorie counts from pictures, or calorie needs per person per day based on age, weight, health status and exercise level. There has been a good amount of discovery in terms of systems and methods to determine food consumption amounts and thus caloric consumption. All of this is used to help a person making a decision based on the person's following questions:

a.) "What am I buying?"
b.) "What am I really eating beyond the main food item along with other embeds in the food we have purchased?"
c.) "How much time has elapsed from the time the product or food is lifeless or plucked from a plant?"
d.) "What else am I eating along with (as an unknown part of) my main food purchase?"
e.) "If I buy a meal containing beef, is the "meat" I am buying beef alone or is the "meat" actually beef plus "SOMETHING" else (such as breading, soy sauce, a "pumping" material, or mono-sodium glutamate (MSG))?" Is the beef sourced locally or is it coming from Australia or other far-away country? What is the percentage of this "SOMETHING" else?"
f.) "Are the calories labeled on the food that I am consuming accurate? If not, how much higher or lower is it from the labeled value?" Food caloric-content reports often have errors or bias (e.g., salad calorie count may omit contribution from the dressing).
g.) "If the $0.99 shrimp nuggets have only portion of the item as real shrimp, what would happen in the long run if I eat these nuggets on a daily basis?"
h.) "How old is the shrimp in the shrimp morsel and where did it start its journey?"
i.) "If I am purchasing and eating Washington natural cherries, are they from Washington? What else should I know about these cherries that would be beneficial for my life health?"

In some embodiments, the present invention provides a system that includes a personal computing device, along with an associated remote server system, and the associated method used to evaluate a consumable (items and ingredients consumed for food, cosmetics (skin, eye and body care) or the like), wherein the system provides information and alerts to facilitate and enable the users to lead healthier lives; the system elicits and receives information "on-site" (i.e., from within the user's personal computing device (PCD)) and/or "off-site" (i.e., from the associated remote server system) regarding source, use, ingredients, attributes and resulting medical health effects of consuming such food/s and cosmetic items on the particular user or a population of users in an identified group of users. In some embodiments, the apparatus predicts and displays information regarding, for example, food freshness (i.e., age, perhaps as measured from the moment or times of harvest of the various ingredients), allergen type and its presence, age-spot-causing food components, country source, and certain targeted biochemical contents, and the like, customized for the particular user, as well as outputting identified alternative consumables that are predicted to provide better cost-benefit results, improved medical and metabolic health outcomes. Some embodiments further determine a MIL (Movement in Life) score related to the user's rate of calorie expenditure based on their amounts and intensity of physical movement and rest; and based on the user's MIL score some embodiments further determine a "Food Goodness for User Purpose" index quantified via FIT (Food Information Technology) and FAT (Food-to-Aging Trajectory) score algorithms (see, e.g., FIG. 13B) that helps categorize foods to be consumed based on the food's health or non-health attributes (e.g., the speed of decay of food and the amount of waste generated or left over) as determined using domain-expert-provided peer-reviewed and evidence-based data and based on the rate of calories consumed by the average person (the general-population MIL score) and/or based on the user's personal MIL score.

The apparatus and scientific method of the present invention includes methods to obtain information about the particular user and the user's current environment to create individualized user profiles for each user. In some embodiments, the present invention elicits and receives information from the individual herself or himself as to their personal health history, attributes, allergies and sensitivities, as to such data about their relatives, as to their genetic heritage or ethnicity, and like information. These embodiments also gather customized information and formulae, based on the information provided by the user, from the knowledge-nutrition-database of the server of the present invention. These embodiments then generate a customized personal private profile that is stored on the user's personal data device (such as a smartphone, wearable computer, desktop computer, laptop computer or tablet computer). The person's customized personal private profile is referenced (retrieved) later with respect to each consumable in order to provide an analysis of the short-term and cumulative effects that are likely to result if that person consumes the particular item or combination of items. In some embodiments, the present invention keeps track of when, which items and how much of each are consumed such that long-term results can be correlated to past behavior and consumption patterns.

In some embodiments, the present invention also includes methods, sensors, devices and other means to identify certain histamine-triggering allergens, non-histamine-triggering allergens and other unwanted components in food, their origins and source of the food and its components and any relevant information for identification. The apparatus (performing its method) then sends out a request (in some embodiments, this request is encrypted for maintaining the privacy of the individual) for information on biochemical content (including nutrients) and other building blocks of the chosen item(s) to a knowledge-nutrition database computer server of the present invention (e.g., in some embodiments, the user's personal device requests data from a computer server that contains the nutrition-database and that is connected to the internet). In some embodiments, the knowledge-and-nutrition database computer server of the present invention checks against online databases (e.g., databases provided by food companies, universities, user groups, non-governmental organizations (NGOs) and governmental agencies) and/or "on-device" databases (e.g., data stored locally on the user's personal smartphone, wearable computer or iPad®-type device as to past consumption by this particular user and resulting effects of that past consumption) to acquire data to obtain adequate information for the process. That acquired data (which includes the set of ingredients, the condition of the food item, past reactions of the particular user to having eaten the item, past consequences of the consumption on a particular group of people of which the user is a member, and the effects of consumption on the health and well-being of the population as a whole, as well as the effects on the Earth's environment, populations of fish, unintended effects on populations of other animals, trees and plants, use of non-renewable energy, ocean health and sustainability, and mineral accumulations in ocean beds, fertilizers, the release of heavy metals in obtaining ocean or river protein (e.g., by drag-netting the ocean floor off a river delta, heavy metals, phosphorus or organic pesticides may be released) or mining chemicals and fertilizers for raising the animals or crops, the effect of pesticides used to grow and store the food's ingredients, and the like) is then processed by the knowledge-and-nutrition database computer server of the present invention (or offsite elsewhere) and/or on the user's personal device, and the results are output from the user's personal device to the user as a prediction of the effect of each food item on their health, baseline weight, longevity, personal wellness and other wellness attributes. In some embodiments, the output also includes a prediction as to how well the food item will satisfy the user's particular craving (for example, the need for Vitamin D in persons living in high latitudes, or Vitamin B12 in vegetarians) or need for deliciousness. In some embodiments, the output also includes a prediction as to the effect of consumption of this type of food on the environment, climate, endangered species, human rights, and the like.

In some embodiments, the present invention tracks each of a set of targeted food items as to when and how much was consumed by each anonymous person with correlated data as to that person's genotype and particular characteristics as a means to aggregate the impact of each targeted food item (and combinations of food items) on the sub-population or genotype to which that the person belongs (e.g., Caucasian, Latino, American Indian, Asian or other race genotypes, ethnicities, religions, geographical-region populations, and/or phenotypes) as well as a mean to aggregate data for the entire population assuming the whole population is culturally conditioned to consuming certain foods (e.g., the addition of lard in certain food items and in certain cultural genotypes).

As noted in the background section above, it is extremely expensive to do well-controlled human biosciences and health experiments, unless humans of a wide array of different ages and genotypes were to be locked in biospheres (controlled, isolated, and heavily monitored environments) and subjected to double-blind tests of food items, alternatives and combinations of foods (and/or cosmetics and/or pharmaceuticals), as well as timing and amount of consumption and environmental conditions.

As an alternative to such well-controlled human biosciences and health experiments, some embodiments of the present invention aggregate data from millions of instances of an individual of an identified genotype or phenotype consuming a particular food item or combination of foods along with data as to the amount and timing of consumption and the short-term and long-term consequences to the individual. This aggregate data is then analyzed to determine the regressions and correlations of what is consumed and the resulting consequences, and the results of that correlation analysis (to the entire population, to each tracked genotype or phenotype, to populations in a geographical or climate region, and to the individual user) is then used to generate later predictions and recommendations to the individual user the next time the user uses the present invention to inquire about that food item or combinations of foods.

In some embodiments, a particular user has provided personal information in response to the user's device eliciting that data. The user's device receives, tracks and accumulates personal data over time and, to protect privacy, provides "anonymized" versions of the data to the nutrient-database computer server, which aggregates the data from many users and consuming many food items over a long period of time. This aggregation and the resulting modifications to the database that associates consumption to the resulting effects to certain types of individuals and to society and the environment as a whole.

U.S. Pat. No. 8,897,539 (which is incorporated herein by reference) describes that a stream of image frames depicting a structure in a scene are obtained. The stream of image frames may include first image frames from a first imaging device and second image frames from a second imaging device. Using the first image frames and the second image frames, a wireframe of at least a portion of the structure is generated. From the wireframe, as-built dimensions may be identified, materials estimates may be determined, and/or data for a fabrication device may be generated.

In some embodiments, the present invention uses similar techniques but modified to apply to determine the volume (i.e., portion size) of a food consumable, which is then combined, using the user's PCD, with other specific information about the food consumable (such as that the food consumable is a burger of a particular type from a particular fast food restaurant, or that the food consumable is a slice of pizza from a particular type of pizza baked from a particular brand of frozen pizza, or the like) in order to compute an estimate of the total calories, the number of calories from fat versus the number of calories from carbohydrates, the amount of each type of meat or vegetables, the amount of salt, sodium or other preservatives, and other relevant nutritional data about each food consumable that the user plans to eat.

FIG. 1A is a block diagram of a method 101 for assisting a user 60 make informed personal well-being decisions regarding a consumable item 80, according to some embodiments of the present invention. In some embodiments, FIG. 1A is related to feature number 4 of FIG. 17. In some embodiments, data 111 in the user's device 110 (note that reference number 110 refers both to the user's device (such as PCD 1310 of FIG. 13A) and to the method (such as method 1302 of FIG. 13B) performed by the device, and the device 110 is any suitable user personal computing device, or network of such devices, such as a smart phone with camera, a smart watch, a iPad®-type computing device, or the like) elicits and receives inputs from camera and sensors in the device 110 (as well as controlling outputs from device 110 such as light flashes of different colors, sound pulses from the device's speaker or ultrasound transducer, and the like) regarding a consumable item 80; elicits and receives data from the user 60 about the particular user 60 (e.g., user profile 1338 of FIG. 13A) and data regarding food item 80 (the user's input as to the food-identification data (e.g., sensor data 1333 of FIG. 13A, which includes data elicited and received into device 110 from user 60)), and calculates food-id data derived from sensor and/or user inputs, in order to form data 111 (e.g., each user's personal device (e.g., smartphone) gathers inputs from camera and sensors; elicited and received data about particular user 60 and user data regarding food item 80 to generate food-id data derived from sensor and user inputs to form the input data 111) and communicates 114 the user data and/or food data to a process 121, some or all of which can be located in the device 110 of each particular user 60 and/or in a remote centralized and/or distributed server connected to the internet. In some embodiments, reference database data 112 (including inputs from peer-reviewed articles, data about particular user's types and groups, data regarding food item and its source, food-id data derived from reference and calibration items, and the like) is also input 113 and stored as a reference database used by processing and analysis process 121. In some embodiments, processing and analysis process 121 runs on nutrition-data computer server and/or user's personal device and performs calculations to: identify food item(s) and ingredients, and calculate effects on this user, and on environment and population as a whole. In some embodiments, the results are communicated 124 to and presented from the device 110 of user 60 to user 60 (e.g., in some embodiments, the output from each user's personal device (e.g., smartphone) to user 60 includes effects of food item on particular user and on the population as a whole, the environment, endangered species, etc. (presented as text, graphical, audio, tactile, etc.). In some embodiments, the output causes a request 133 for more information about user 60 and/or consumable item 80.

FIG. 1B is a high-level block diagram of a method 102 for identification of a consumable and its condition and ingredients, according to some embodiments of the present invention. In some embodiments, FIG. 1B is related to features 4, 9, 10, 23, 24, 25 and 26 of FIG. 17. In some embodiments, method 102 includes one or more of the flowing blocks: block 141 obtains inputs from camera: QR or bar-code reader; optical-character recognition (OCR) of ingredient list, etc.; block 142 that obtains a plurality of images for volume calculations, spectral analysis, shininess determinations and the like; block 143 obtains sound information such as receiving multiple sounds reflections or sonogram data resulting from emitting a very-short duration and/or shaped sound emitted from device 110; block 144 receives chemical information from odors, food-sniffing sensors, breathalyzer sensors that analyze the breath of user 60 after consuming some or all of item 80, and the like; and clock 145 elicits and receives input from user 60 such as gestures from a graphical user interface (GUI), touch sensors and buttons, voice recognition, and the like. Process 151 performs pattern recognition (e.g., in some embodiments, uses a pattern-recognition method such as described in U.S. Pat. No. 8,055,599 to Werth that issued Nov. 8, 2011 with the title "Pattern recognition using cycles or traces in an associative pattern memory (APM), vertical sensors, amplitude sampling, adjacent hashes and fuzzy hashes," which is incorporated herein by reference) to determine food type, age, source, processing, and ingredient contents, etc. and generates output identification data 161 about consumable item 80. In some embodiments, the user aims the camera in their personal or wearable device to obtain one or more images of item-identification codes that are on a label in QR form or bar-code form; this data is used to look up food-item data from the producer or other source of data associated with the bar code or QR data. In some embodiments, (alternatively or additionally) the user aims the camera to obtain one or more images of the label (brand name, item name and/or ingredient list) that are decoded using well-known OCR techniques to obtain a list of ingredients, calorie count, amount of carbohydrates, fats, proteins, sodium, and the like. The ingredients are then compared to ingredient that the system of the present invention has determined are beneficial or detrimental to this particular user.

In some embodiments, the present invention uses methods and apparatus for pattern matching of the processed data obtained from the imager and other sensors of the user's personal computing device. For example, some embodiments use methods such as described in U.S. Pat. No. 8,055,599 of Werth, which is incorporated herein by reference. In some embodiments, a plurality of images taken by the camera under different color LED flashes are processed to generate multi-dimensional histograms using method 301 described below, and the histograms and other sensor date and user-inputted data are processed by a pattern-matching algorithm, such as described in U.S. Pat. No. 8,055,599, to obtain an identification of the food item and its characteristics and components (ingredients, allergens, age, source, travel, processing and the like).

In some embodiments, any of the features described herein as "block nnn" are implemented as software that controls operation of one or more suitable computing devices to make that (those) computing device(s) into special purpose machine(s) that receive inputs and control or generate outputs (such as turning on a device to alert the user and/or outputting visual, haptic or audio information). In some embodiments, such blocks are implemented in part (or entirely) by electronic circuits or programmable logic circuits (PLCs).

FIG. 2A is a block diagram of a method 201 for alerting a user of late-arriving data that changes a recommendation made earlier by method 101 such that a different recommendation should now be considered, according to some embodiments of the present invention. In some embodiments, method 201 includes block 221 (connected to a database 212) wherein a centralized server receives exigent data (different from prior data) regarding a particular batch of items or shipment of ingredients, and the server generates and communicates a warning or recommendation that is different than one generated for the same user 60 about the same consumable item 80. The communication 222 turns on the user's device 110, which wakes up and alerts 211 the user 60 about the item. If the warning is delivered before the user has already consumed the particular item 80, the user can choose to dispose of the item, whereas if the item 80 has already consumed the item 80, the user 60 can seek medical help to obtain a remedy or treatment.

Figure 2B:
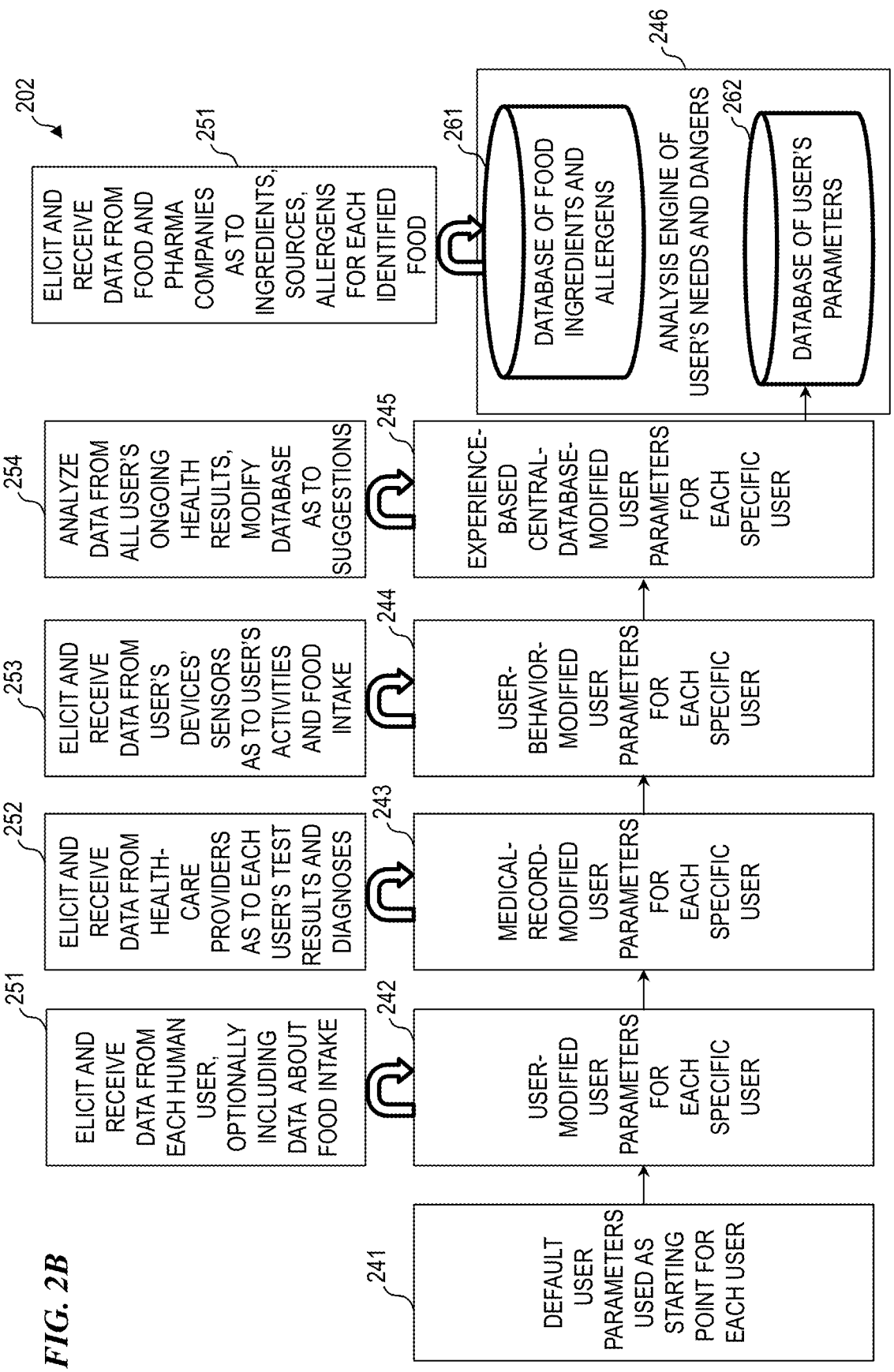
FIG. 2B is a block diagram of a method 202 for gathering data from a plurality of sources for identifications and recommendations, according to some embodiments of the present invention.

FIG. 2B is a block diagram of a method 202 for gathering data from a plurality of sources for identifications and recommendations, according to some embodiments of the present invention. In some embodiments, method 202 includes block 241 (which includes storing default user parameters used as a starting point for each user); block 242 (which calls block 251 to elicit and receive data from each human user, optionally including data about their normal food intake) generates user-modified user parameters for each specific user; block 243 (which calls block 252 to elicit and receive data from each of a plurality of health-care providers as to each user's test results and diagnoses) generates medical-record-modified user parameters for each specific user; block 244 (which calls block 253 to elicit and receive data from each of a plurality of user's devices' sensors as to user's physical activities and food intake) then generates user-behavior-modified user parameters for each specific user; block 245 (which calls block 254 to analyze data from all user's ongoing health results, modify database as to suggestions) then generates experience-based central-database-modified user parameters for each specific user, which is then stored into database of user's parameters 262. in some embodiments, some or all of the database of user's parameters 262 is stored on the PCD(s) 80 of the particular user 60 and some or all of the database of user's parameters 262 of the particular user 60 is stored on the centralized database part of the system having analysis engine block 245 (e.g., user account 1348 of FIG. 13A) that calculates the user's needs and dangers. in some embodiments, analysis engine block 245 (which calls block 254 to elicit and receive data from food and pharma companies as to ingredients, sources, allergens for each identified food, pharmaceutical, vitamin supplement and cosmetic item and put the results in database 261 of food ingredients and allergens) uses data from database 261 and database 262 to form a plurality of linear equations with parameters and weightings from and about the particular user 60 and particular consumable item 80 and to solve the linear equations and use the result to generate (e.g., in some embodiments, using table lookup functionality) a recommendation to present to the user 60 and/or control an output such as turning on the user's PCD 110 and delivering a warning via the now-activated PCD 80. In some embodiments, the PCT 80 includes a refrigerator or cupboard connected by the user's internet of things (JOT).

Figure 3A:
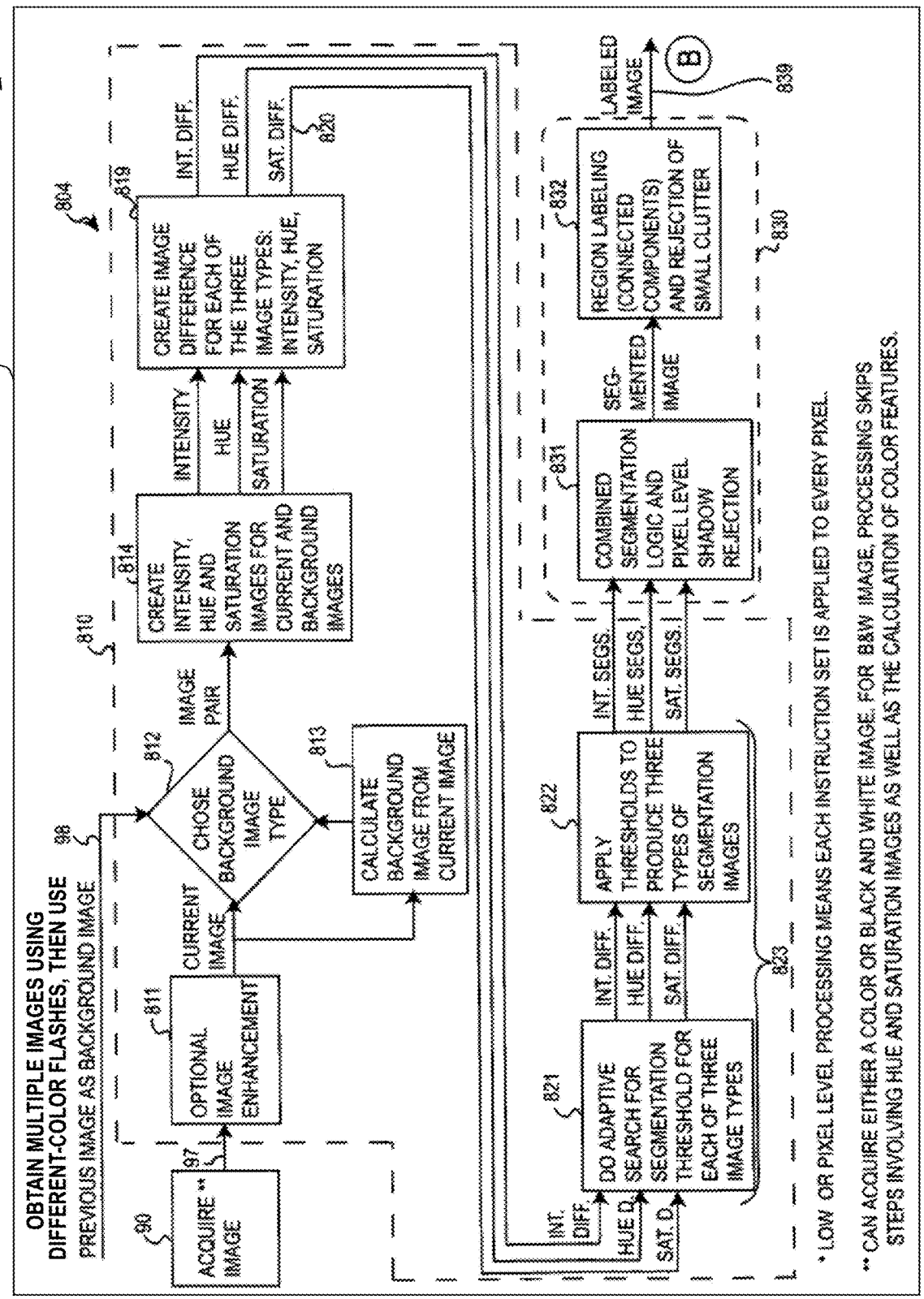
FIG. 3A is a block diagram of the first, low-level-processing, portion 301 of a method 300 for identification of a consumable and its condition and ingredients, according to some embodiments of the present invention.
Figure 3B:
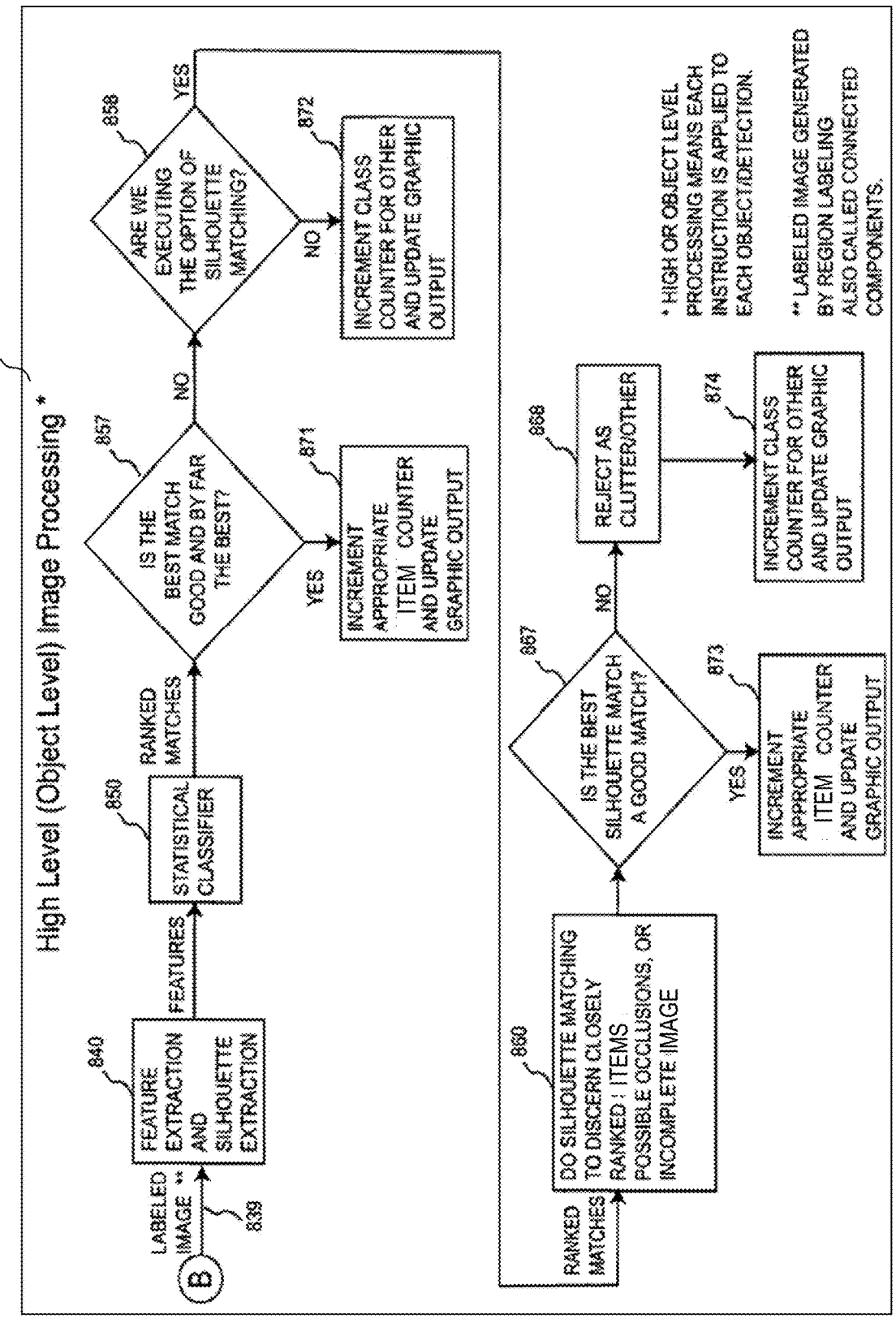
FIG. 3B is a block diagram of the second, high-level-processing, portion 302 of a method 300 for identification of a consumable and its condition and ingredients, according to some embodiments of the present invention.

FIG. 3A and FIG. 3B show two portions of an image-processing method 300 (which includes portions 301 and 302) that, in some embodiments, is a modification of the methods described in U.S. Pat. No. 7,496,228 to Landwehr, et al. to instead identify, via hue, saturation, intensity of colors, and outline shape and size across an image of the entire consumable item 80 and the level of processing (LP number) and other parameters about the consumable item 80, which is incorporated herein by reference. In some embodiments, FIG. 3A and FIG. 3B are related to features 23, 24, 25 and 26 of FIG. 17. In some embodiments, (and in contrast to the method of Landwehr, et al.), the present invention uses a dual-flash feature (or multiple-color flash, wherein the colors include successive flashes from (1) an ultraviolet (UV) flash LED to obtain fluorescent images of the food item, (2) a blue flash LED, (3) a green flash LED, (4) a yellow flash LED, (5) a red flash LED, (6) one or more different infrared wavelengths (IR) flash LED(s), (7) a white-blue (cold-color-tone) flash LED, and/or (8) a white-orange (warm-color-tone) flash LED) feature of the user's smart phone to take two or more images in quick succession (in some embodiments, at 60 frames per second). In some embodiments, method 301 uses image differences between the various images (taken under various lighting conditions) to deduce the identification, ingredients, age, condition, and other characteristics of the food item. As was done in U.S. Pat. No. 7,496,228, some embodiments of method 301 determine the outer boundary of the object, and calculate a multiple-dimensional histogram of intensity, hue and saturation of the red-green-blue values of each/all (or a subset) of the pixels of the object within the boundary. In some embodiments, the multiple-dimensional histogram further includes fluorescent colors that are stimulated by the UV or blue flashes, and/or one or more infrared wavelengths stimulated by the IR flash LED(s) and/or fluorescence that downshifts the IR light from the other colored flash LEDs.

FIG. 3A is a block diagram of the first, low-level image-processing, portion 301 of a method 300 for identification of a consumable and its condition and ingredients, according to some embodiments of the present invention. In some embodiments, method portion 804 provides low-level (or pixel-level) image processing, according to some embodiments of the invention. Low-level processing means that each function is applied to each pixel. At block 90, some embodiments of method portion 804 include acquiring the image. The acquired image can be either a color or black-and-white (B&W) image. For B&W images, the processing skips functions involving hue and saturation images as well as the calculation of color features. At block 811, some embodiments of method portion 804 include optional enhancing of the image as described for FIG. 3B. At block 813, some embodiments of method portion 804 include calculating a background image from the current image (e.g., determining what color most of the pixels are in a given area, and using that color as the background for that area). At block 812, some embodiments of method portion 804 include receiving multiple images 98 and choosing which background image type to use. At block 814, some embodiments of method portion 804 include creating intensity, hue, and saturation images for the current and background images, as described in U.S. Pat. No. 7,496,228, which is incorporated herein by reference. At block 819, some embodiments of method portion 804 include creating difference images (between the current and background images) for each of the three image types (intensity, hue, and saturation), and producing outputs 820. At block 821, some embodiments of method portion 804 include performing an adaptive search for a segmentation threshold for each of the three image types. At block 822, some embodiments of method portion 804 include applying thresholds to produce three types of segmentation images. Block 830 includes blocks 831 and 832. At block 831, some embodiments of method portion 804 include applying combined segmentation logic and pixel-level shadow rejection to produce a segmented image. At block 832, some embodiments of method portion 804 include labeling regions (using connected components logic) and/or rejecting small clutter, to produce a labeled image 839. The labeled image generated by region labeling is also called connected components. Control then passes to FIG. 3B.

FIG. 3B is a block diagram of the second, high-level image-processing, portion 805 of a method 301 for identification of a consumable and its condition and ingredients, according to some embodiments of the present invention. High-level processing means that each function is applied to each object or detection. At block 840, some embodiments of method portion 805 include extracting features and/or silhouettes. At block 850, some embodiments of method portion 805 include performing statistical classification. At branch block 857, some embodiments of method portion 805 include going to block 871 if the best match is "good" and by far the best; else control passes to block 858. At block 871, some embodiments of method portion 805 include incrementing the appropriate species counter and/or updating graphical output. At branch block 858, some embodiments of method portion 805 include going to block 872 if the method is not executing the option of silhouette matching; else control passes to block 860. At block 872, some embodiments of method portion 805 include incrementing the classification counter for "other" (for detected objects that were not matched to any reference item included in the reference database) and/or updating the graphical output. At block 860, some embodiments of method portion 805 include performing silhouette matching to discern closely ranked food items, or possible occlusions, or incomplete or damaged food items. At branch block 867, some embodiments of method portion 805 include going to block 873 if the best silhouette match is "good"; else control passes to block 868. At block 873, some embodiments of method portion 805 include incrementing the appropriate species counter and/or updating graphical output. At block 868, some embodiments of method portion 805 include rejecting the detected object as clutter or "other" and going to block 874. At block 874, some embodiments of method 805 include incrementing the classification counter for "other" and/or updating the graphical output.

FIG. 4A is a schematic diagram of a device 401, such as a handheld, with a pair of cameras 411 to give stereoscopic imaging and sensing, with a small predetermined distance between them to compute things such as volume or creating a 3D image, according to some embodiments of the invention. In some embodiments, FIG. 4A, FIG. 4B, FIG. 4C and FIG. 4D are related to features 3, 9, and 10 of FIG. 17. In some embodiments, device 401 includes case 413, a plurality of imager-acquisition units 411 (e.g., digital cameras) and a plurality of light-emitting flash units (e.g., LEDs or lasers that each emit a spectrum of wavelengths that is unique— different than the other spectra). In some embodiments of the devices of FIG. 4A, FIG. 4B, FIG. 4C and FIG. 4D, the present invention uses methods and devices to determine a food-item's size or volume such as described in U.S. Pat. No. 8,897,539 titled "Using images to create measurements of structures through the videogrammetric process," PCT Publication No. WO2013/173383 by Brilakis et al. titled "Methods and apparatus for processing image streams," U.S. Pat. No. 8,855,406 to Lim, et al. titled "Egomotion using assorted features," and/or U.S. Patent Publication US2013/0083990, which are all incorporated by reference in their entirety.

FIG. 4B is a schematic diagram of a wearable device 402, specifically glasses, with a pair of cameras 411 to give stereoscopic imaging and sensing, with a small predetermined distance between them to compute things such as volume or creating a 3D image, according to some embodiments of the invention. In some such embodiments, wearable device 402 includes case (including, e.g., eyeglasses or video screens) 414, a plurality of light-emitting flash units 412 (e.g., LEDs or lasers that each emit a spectrum of wavelengths that is unique—different than the other spectra).

FIG. 4C is a schematic diagram of a device 403 (similar to device 402 as described in FIG. 4B) as an example of a different embodiment for the camera, with a larger predetermined distance between them to compute things such as volume or creating a three-dimensional (3D) image, according to some embodiments of the invention, showing one of many variations of the design.

FIG. 4D is a block diagram of a method, wherein stereoscopic imaging takes two (or more) images, and performs calculations to create a 3D model 81 that includes linear measurements in three dimensions (e.g., volume elements (voxels) for each component of food item 80, such as voxels for the hamburger meat, each of the condiments, and the bun) and/or a measurement of the volume of a three-dimensional object, according to some embodiments of the invention. For example, in some embodiments, all of the voxels estimated to be hamburger meat are combined to generate a total volume value (e.g., number and size of voxels) for hamburger meat, which is then multiplied by the estimated calories per voxel to output the total calories for hamburger meat, multiplied by the estimated salt per voxel to output the total salt for hamburger meat, multiplied by the estimated fat per voxel to output the total fat for hamburger meat, and so on for each desired parameter or ingredient, and this process is repeated for each of the condiments, and for the bun. In some embodiments, 3D model 81 is used to generate a 3D rendition on the viewing screen of user's PCD 1310 (see FIG. 13A).

FIG. 4E1 and FIG. 4E2 together form a block diagram of an example method 405 (comprising parts 405A, 405B and 405C) wherein a captured object is compared against a database of known objects (e.g., a database of reference patterns that is created by training the pattern recognition program with known items, each creating one or more reference patterns for that type of item), in order to identify the object, or one or more of its closest alternatives, according to some embodiments of the invention. In some embodiments, the present invention uses a pattern-recognition method such as described in U.S. Pat. No. 8,055,599 to Werth that issued Nov. 8, 2011 with the title "Pattern recognition using cycles or traces in an associative pattern memory (APM), vertical sensors, amplitude sampling, adjacent hashes and fuzzy hashes," and which is incorporated herein by reference. In some embodiments, method portion 405A includes block 431 where user 60 holds consumable item 80 to obtain an image via device 110 (e.g., wearable imaging goggles); block 432 where the image has been captured; block 433 where the image is transmitted to the PCD (e.g., smartphone) of the user and/or is transmitted via the internet to a centralized program and database for analysis; and block 434 where the image is processed to isolate the consumable item and compare the isolated item to a database of processed image data of previously identified items. In some embodiments, method portion 405B has the same processing, but performed on image(s) obtained via a smartphone device 110. In some embodiments, method portion 405C includes block 435 that uses fuzzy logic to determine probabilities of match versus each one of a plurality possible matches; block 436 prioritizes or sorts the matches to obtain the top one, two, or three matches, and blocks 437 then present, to the user (e.g., on their wearable goggles) the proposed matches from the system so that the user, if necessary, can choose among a plurality of possible matches or can choose the correct match 439 to replace an incorrect match 438, and that choice is provided as feedback to the system for future use.

Figure 4F:
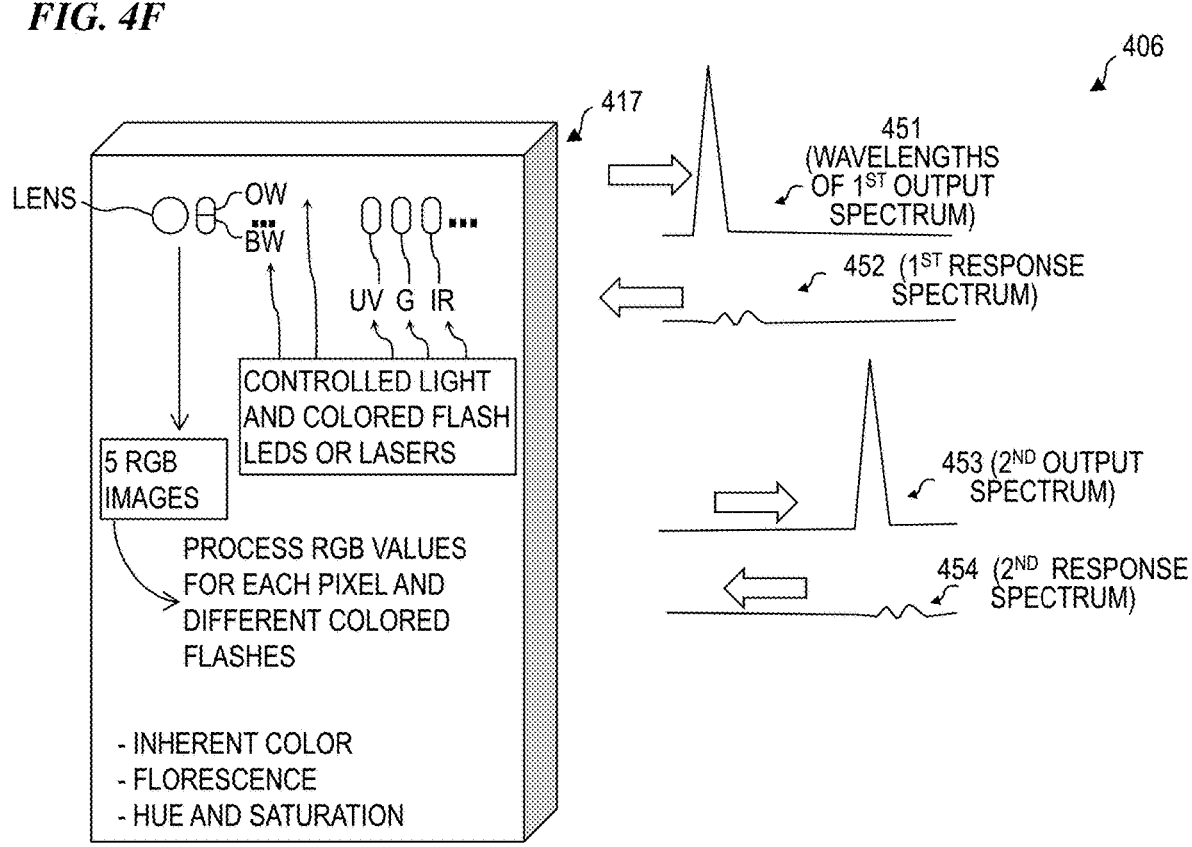
FIG. 4F is a block diagram of a method 406 that uses a device 417 an example of a multiple-flash setup for a device, taking images from the multiple flashes to give a combined differential analysis, according to some embodiments of the invention.

FIG. 4F is a block diagram of a method 406 that uses a device 417 an example of a multiple-flash setup for a device, taking a plurality of digital photograph images from the multiple flashes (for example, each flash being generated by a different set of one or more LEDs or semiconductor lasers, each having different color spectra (the combination of wavelengths) to give a combined differential analysis of the color reflected and/or fluoresced by the food item, according to some embodiments of the invention. In some embodiments, a first light flash 451 having a first spectrum of wavelengths is output, and the return light 452 (reflected or fluoresced) from the item 80 is imaged, then each of one or more other (e.g., a second) light flash 453 having a different spectrum of wavelengths is output, and the return light 454 (reflected or fluoresced) from the item 80 is imaged. In some embodiments, wavelength shifts (due to Ramon scattering) in return light 452 of narrowband laser light 451 is used to determine ingredients or components of the food item 80.

Figure 4G:
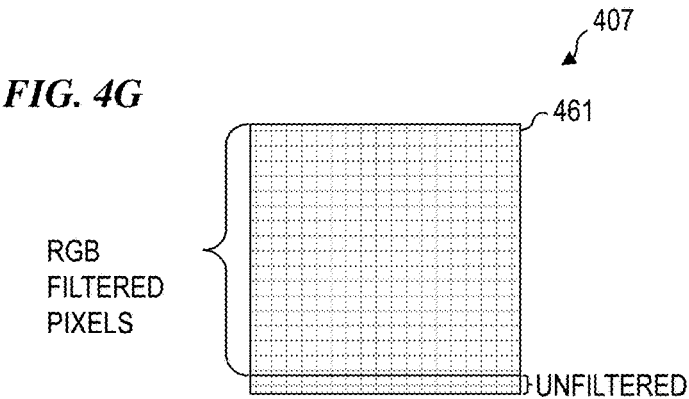
FIG. 4G is a block diagram of camera image sensor 407 with part of the sensor filtered with red-green-blue filters that block infrared (IR) and another part of the sensor left unfiltered (or filtered to block visible light and pass IR and/or ultraviolet wavelengths) to detect information outside the usual visual spectrum, according to some embodiments of the invention.

FIG. 4G is a block diagram 407 of camera image sensor with part of the sensor left unfiltered to detect information outside the usual visual spectrum (the visible light spectrum of human eyes generally being considered to be having wavelengths in the range of 400 nm to 700 nm), according to some embodiments of the invention. In some embodiments, FIG. 4F and FIG. 4G are related to features 23, 25 and 26 of FIG. 17 (varying the flash spectrum emitted for obtaining each of different ones of the images of consumable item 80). In some embodiments, the imager 461 obtains a plurality of sets of filtered image pixels and of unfiltered image pixels, which are then analyzed as set forth herein.

Figure 5A:
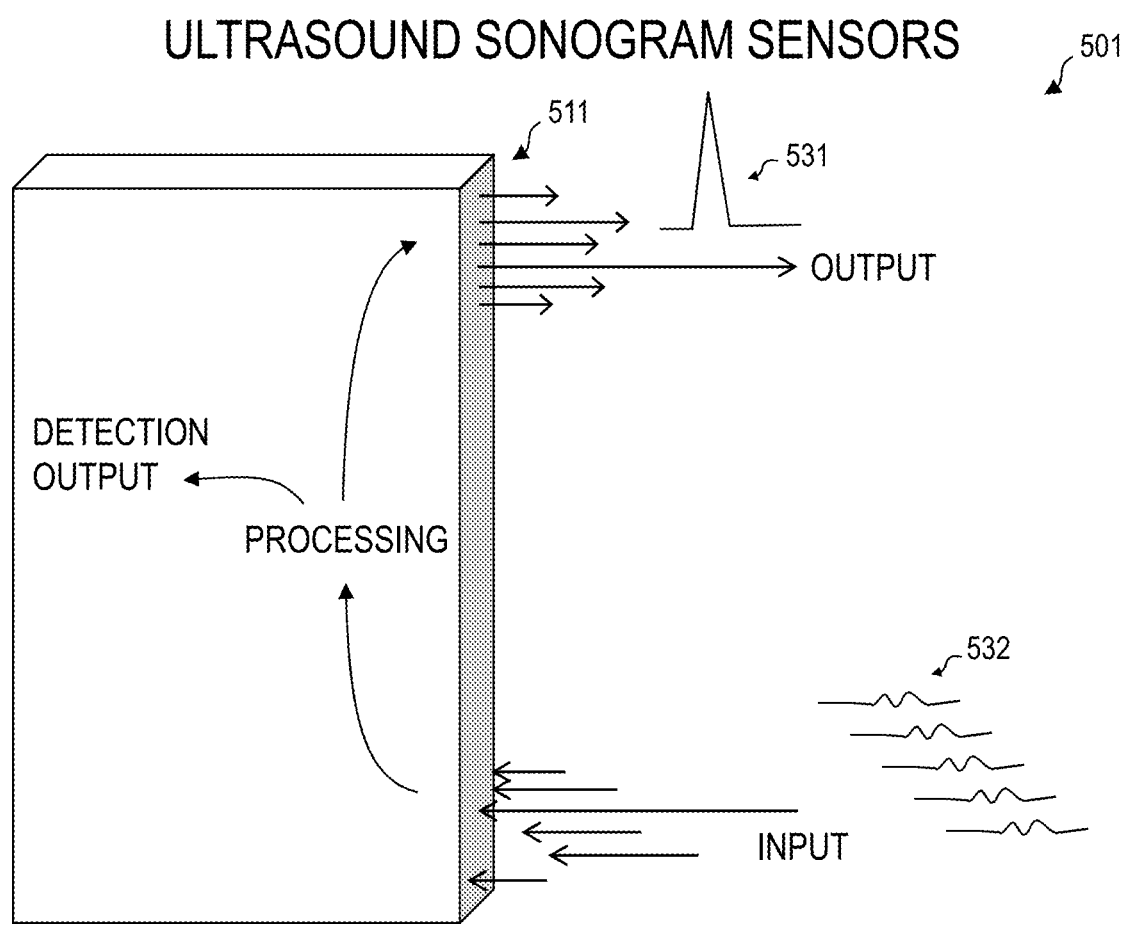
FIG. 5A is a diagram of method 501 that uses a device 511 having sonogram transducers and sensors (e.g., ultrasonic speakers and microphones), sending out sound-pressure information, receiving the reflected sound information, then processing the input, both for analysis, feedback and continued sensing and output, according to some embodiments of the invention.

FIG. 5A is a diagram of method 501 that uses a device 511 having sonogram transducers and sensors (e.g., ultrasonic speakers and microphones), sending out sound-pressure information 531, receiving the reflected sound information 532, then processing the input, both for analysis, feedback and continued sensing and output, according to some embodiments of the invention. In some embodiments, FIG. 5A is related to features 24 and 57 of FIG. 17, obtaining ultrasound-echo data and sonogram images.

Figure 5B:
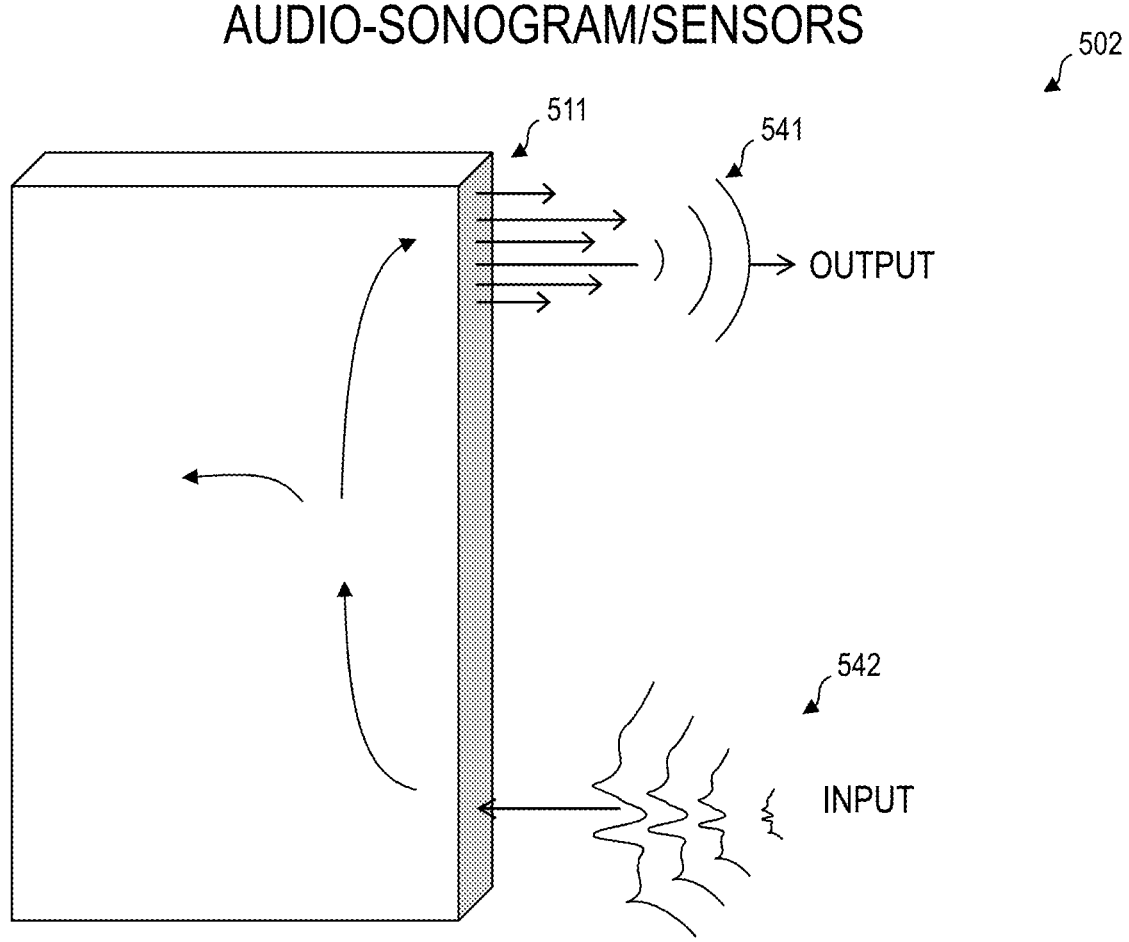
FIG. 5B is a block diagram of method 502 that uses device 511 for other types of sonography sensors, according to some embodiments of the invention.

FIG. 5B is a diagram of method 502 that uses device 511 for other types of sonography sensors, according to some embodiments of the invention. In some embodiments, FIG. 5B is related to features 24 and 57 of FIG. 17, obtaining infrasound-and-audible-echo data images. In some embodiments, device 511, sends out structured (in space and time) directional sound-pressure information 541, receiving the reflected structured (in space and time) directional sound information 542, then processing the input, both for analysis, feedback and continued sensing and output, according to some embodiments of the invention.

Figure 6:
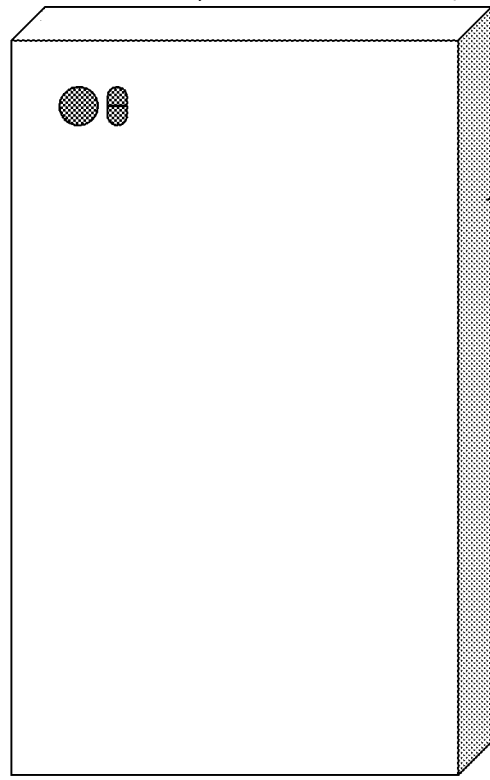
FIG. 6 is a set 601 of diagrams provided as an example of barcodes and QR codes, as well as logos and ingredient lists, that are scanned to obtain product information, according to some embodiments of the invention
Figure 6:
Figure 6:
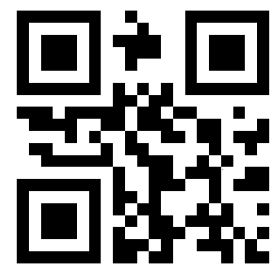
Figure 6:
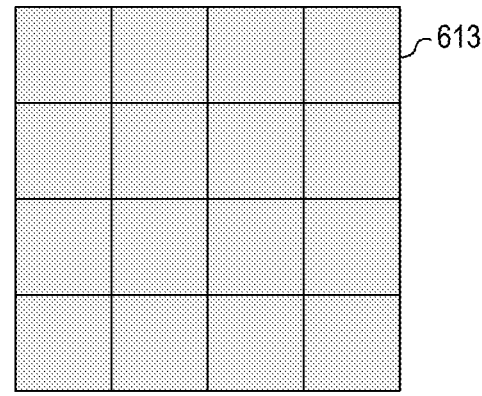
Figure 6:
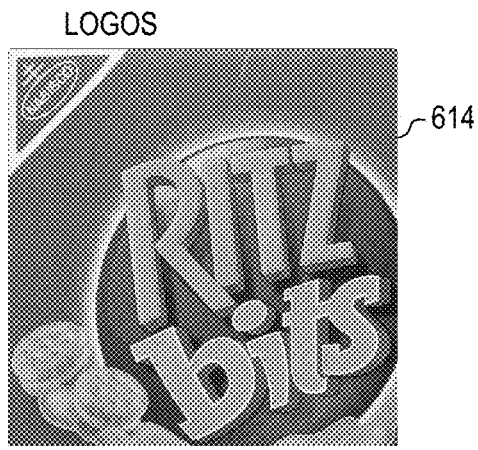
Figure 6:
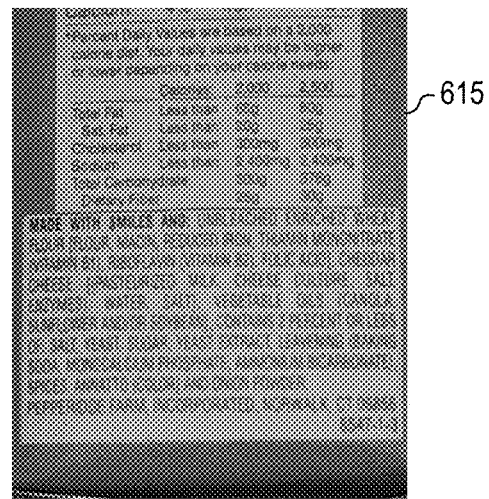

FIG. 6 is a set 601 of diagrams provided as an example of barcodes and QR codes, as well as logos and ingredient lists, that are scanned to obtain product information, according to some embodiments of the invention. In some embodiments, set 601 includes scan codes 611, QR codes 612, pixel information 612, ingredient lists 615 for OCR recognition, and/or logos 614, each of which is imaged by device 610 (which, in some embodiments, is embodied in device 110 of FIG. 1A or device 1310 of FIG. 13A).

Figure 7:
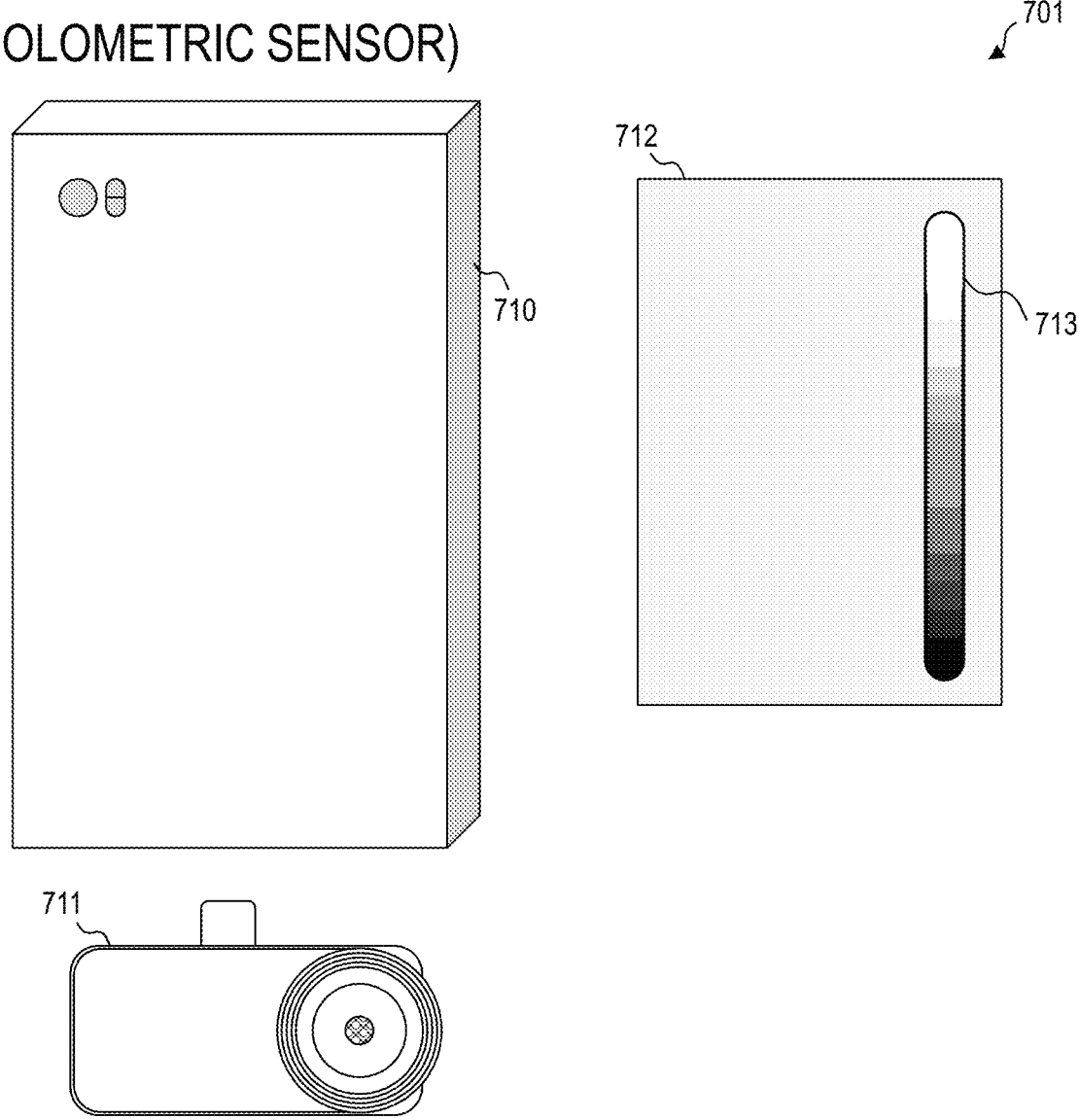
FIG. 7 is an example method 701 that uses an infrared sensor 711 and information output from said sensor, according to some embodiments of the invention.

FIG. 7 is an example method 701 that uses an infrared sensor 711 and information output from said sensor, according to some embodiments of the invention. In some embodiments, a far-longwave IR image 712 with a calibrated temperature scale 713 is imaged by FLIR device 711 (wherein FLIR stands for forward-looking infrared or far-long infrared wavelengths, and which, in some embodiments, is implemented as a plug-on attachment as shown, or in other embodiments, is built into device 710). In some embodiments, FLIR device 711 is implemented as a microbolometer and additional imager, for example such as described in U.S. Pat. No. 6,232,602 to Kerr, which is incorporated herein by reference.

Figure 8:
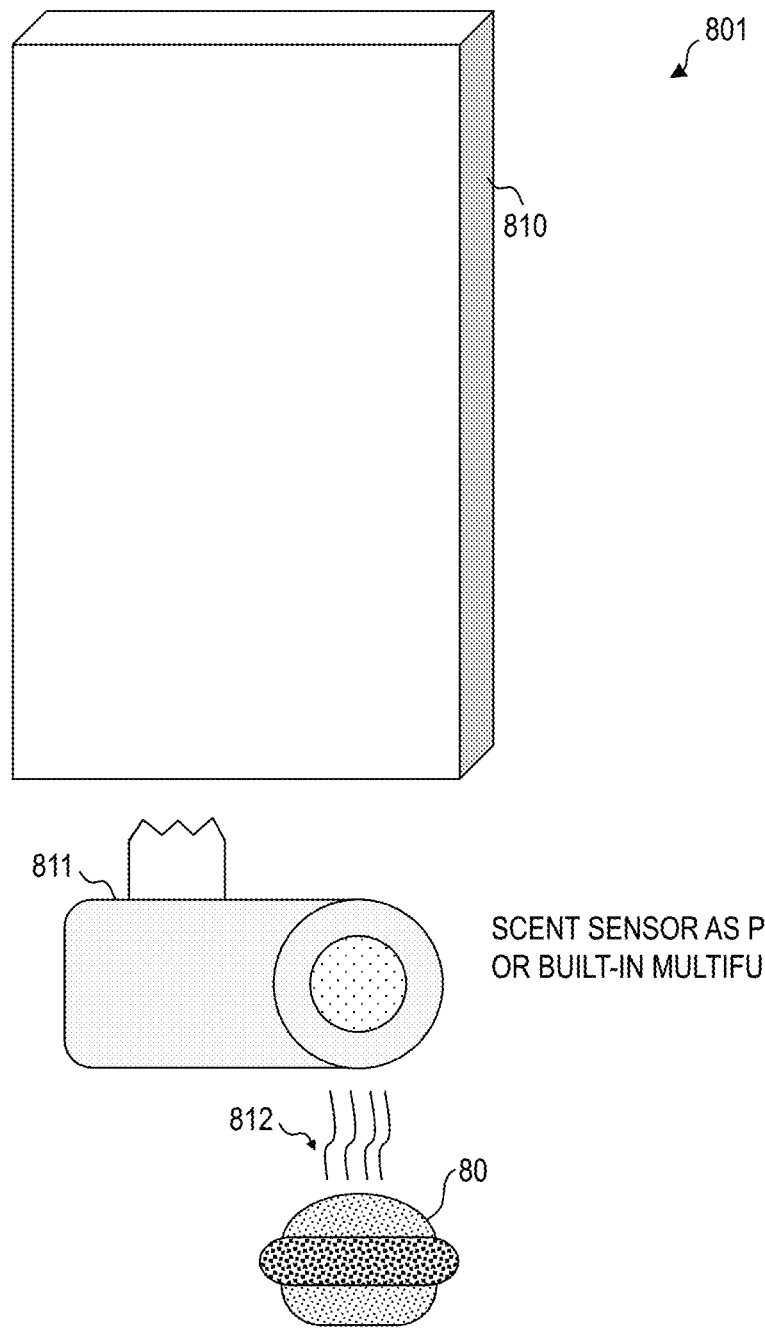
FIG. 8 is block diagram of a method 801 that uses a scent sensor 811, which is used to identify consumable and the quality of the item (whether or not spoiled/cooked), according to some embodiments of the invention.

FIG. 8 is block diagram of a method 801 that uses a scent sensor 811, which is used to identify consumable and the quality of the item (whether or not spoiled/cooked), according to some embodiments of the invention. In some embodiments, a biochemical detector 811 (which, in some embodiments, is implemented as a plug-on attachment as shown, or in other embodiments, is built into device 810) gathers scents or other chemicals from the air around consumable item 80 and generates a chemical signature signal for analysis.

Figure 9A:
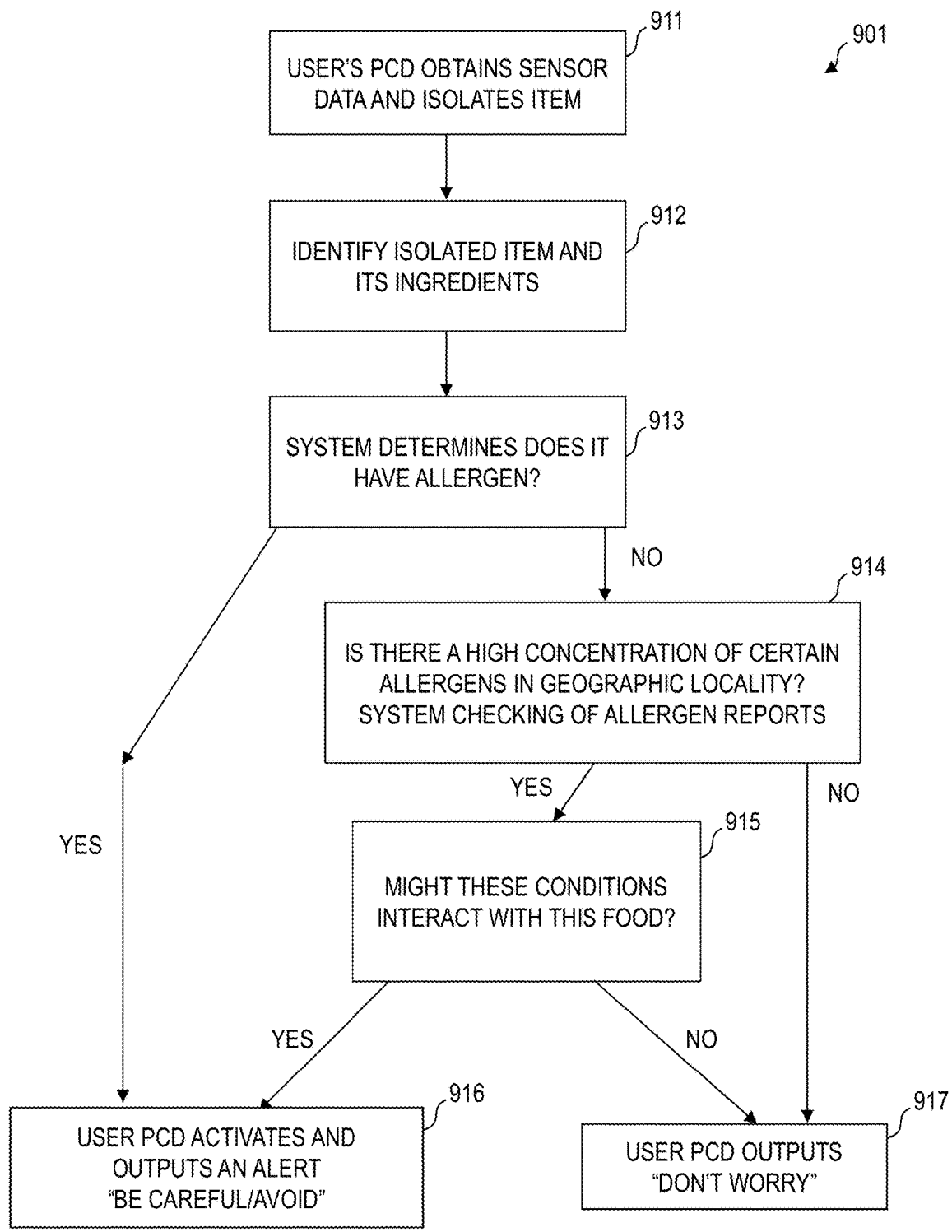
FIG. 9A is a block diagram of a method 901 of detecting whether there is a possibility of an allergic reaction when ingesting the identified item, according to some embodiments of the invention.

FIG. 9A is a block diagram of a method 901 of detecting whether there is a possibility of an allergic reaction when ingesting the identified item, according to some embodiments of the invention. In some embodiments, method 901 includes block 911 (where the user's PCD obtains sensor data and isolates item); block 912 (where the user's PCD identifies isolated item and its ingredients); block 913 (where the user's PCD and/or other portions of system 1301 determines whether it has allergen(s)) and if yes, goes to block 916 (where the user's PCD is activated and outputs an alert (such as be careful of too much or avoid all together) and if no then go to block 914; block 914 (where the user's PCD or the system determines is there a high concentration of certain allergens in geographic locality, including system checking of allergen reports); block 915 (where the user's PCD or the system determines might these conditions interact with this food?) and if yes, goes to block 916 (where the user's PCD is activated and outputs an alert (such as be careful of too much or avoid all together) and if no then go to block 917 (where the user's PCD signals that the food item is safe or "do not worry").

Figure 9B:
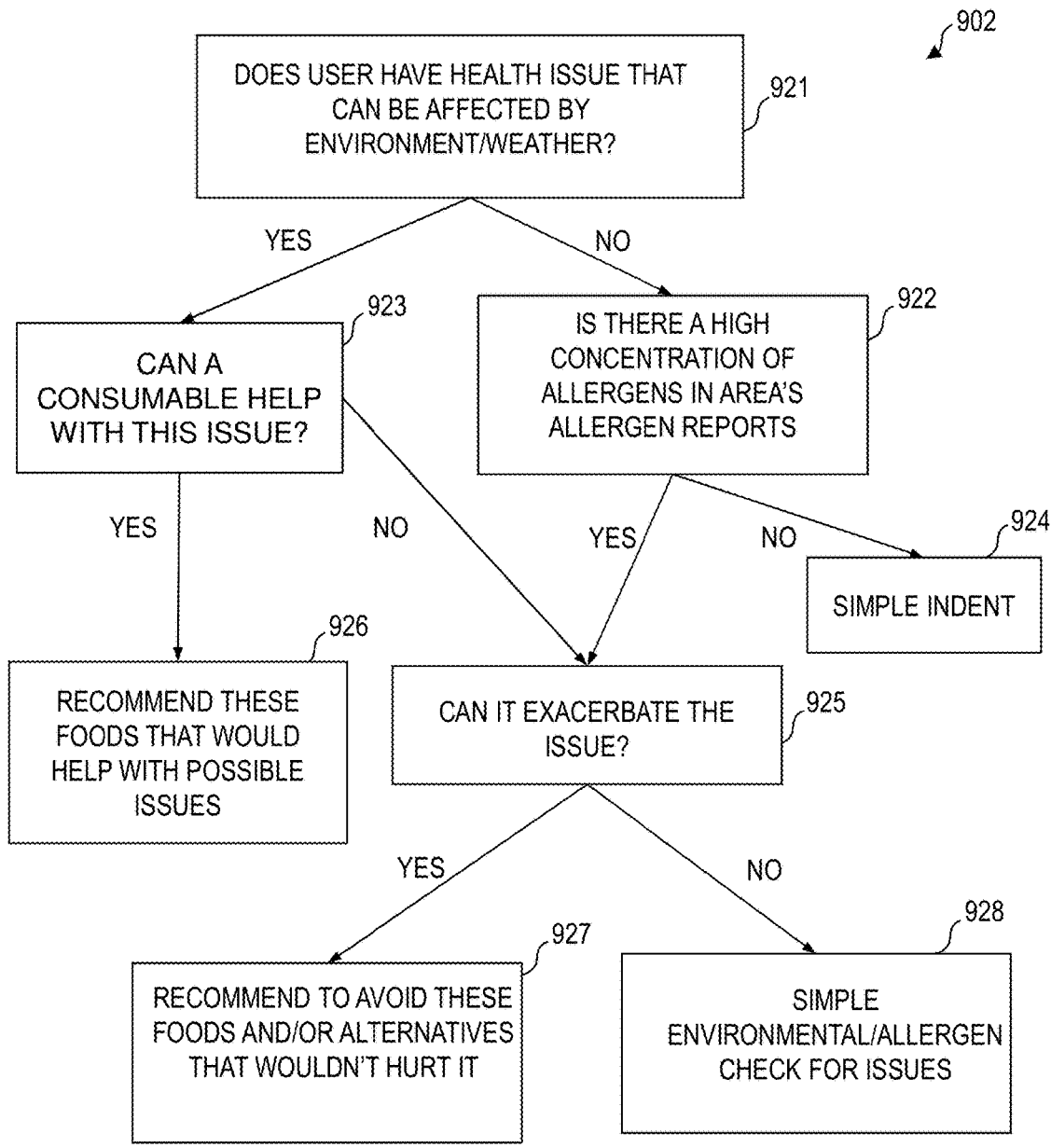
FIG. 9B is a block diagram of a method 902 for determining whether the current environment of the user could cause consumption of the consumable to cause an adverse reaction with the user, according to some embodiments of the invention.

FIG. 9B is a block diagram of a method 902 for determining whether the current environment of the user could cause consumption of the consumable to cause an adverse reaction with the user, according to some embodiments of the invention. In some embodiments, method 902 (which can be implemented in a system that includes the user's PCD and/or other parts of system 1301 of FIG. 13A) includes block 921 (where the system determines does user 60 have health issue that can be affected by environment/weather?

and if yes goes to block 923 and if no goes to block 922); block 922 (where the system determines is there a high concentration of allergens in area's allergen reports? and if yes goes to block 925 and if no goes to block 924 where the system outputs a simple identification); block 923 (where the system determines can a consumable help with this issue? and if yes goes to block 926 and if no goes to block 925); block 925 (where the system determines can the item exacerbate the issue? and if yes goes to block 927 and if no goes to block 928); block 926 (where the system determines recommends a set of one or more foods that would help with possible issues); block 927 (where the system determines recommends to avoid these foods and/or use alternatives that would not hurt or worsen the issue); and block 924 where the system outputs a simple environmental/allergen check for issues.

Figure 9C:
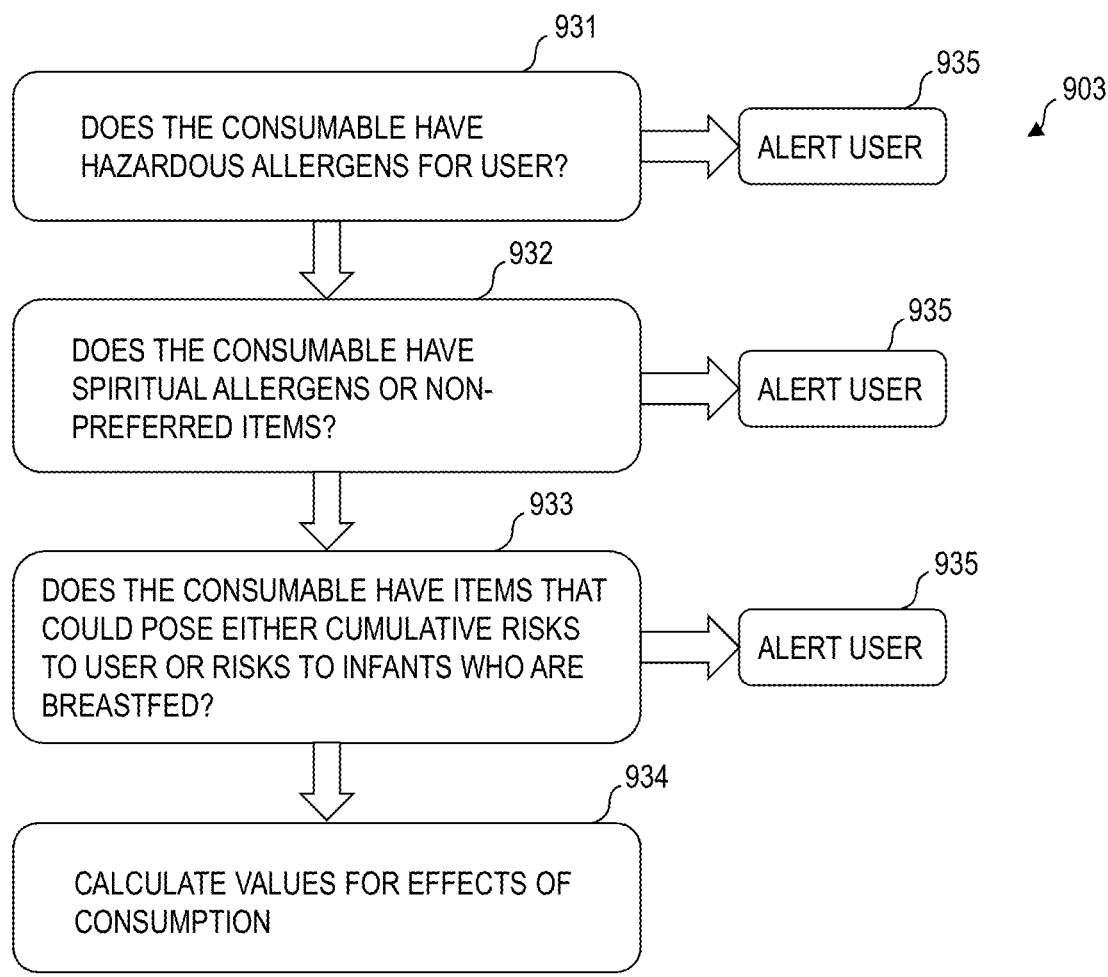
FIG. 9C is a block diagram of an example diagram of the method 903 that checks to alert the user of issues that are more imperative to the user, possibly before doing calculations on the item, according to some embodiments of the invention.

FIG. 9C is a diagram of a method 903 that checks to alert the user of issues that are more imperative to the user, possibly before doing calculations on the item, according to some embodiments of the invention. In some embodiments, method 903 (which can be implemented in a system that includes the user's PCD and/or other parts of system 1301 of FIG. 13A) includes block 931 (where the system determines does the consumable have hazardous allergens for user? and if yes goes to block 935 to alert the user and if no goes to block 932); block 932 (where the system determines does the consumable have spiritual allergens or non-preferred items? and if yes goes to block 935 to alert the user and if no goes to block 933); block 933 (where the system determines does the consumable have items that could pose either cumulative risks to user or risks to infants who are breastfed? and if yes goes to block 935 to alert the user and if no goes to block 934); and block 934 (where the system calculates values for effects of consumption).

Figure 10A:
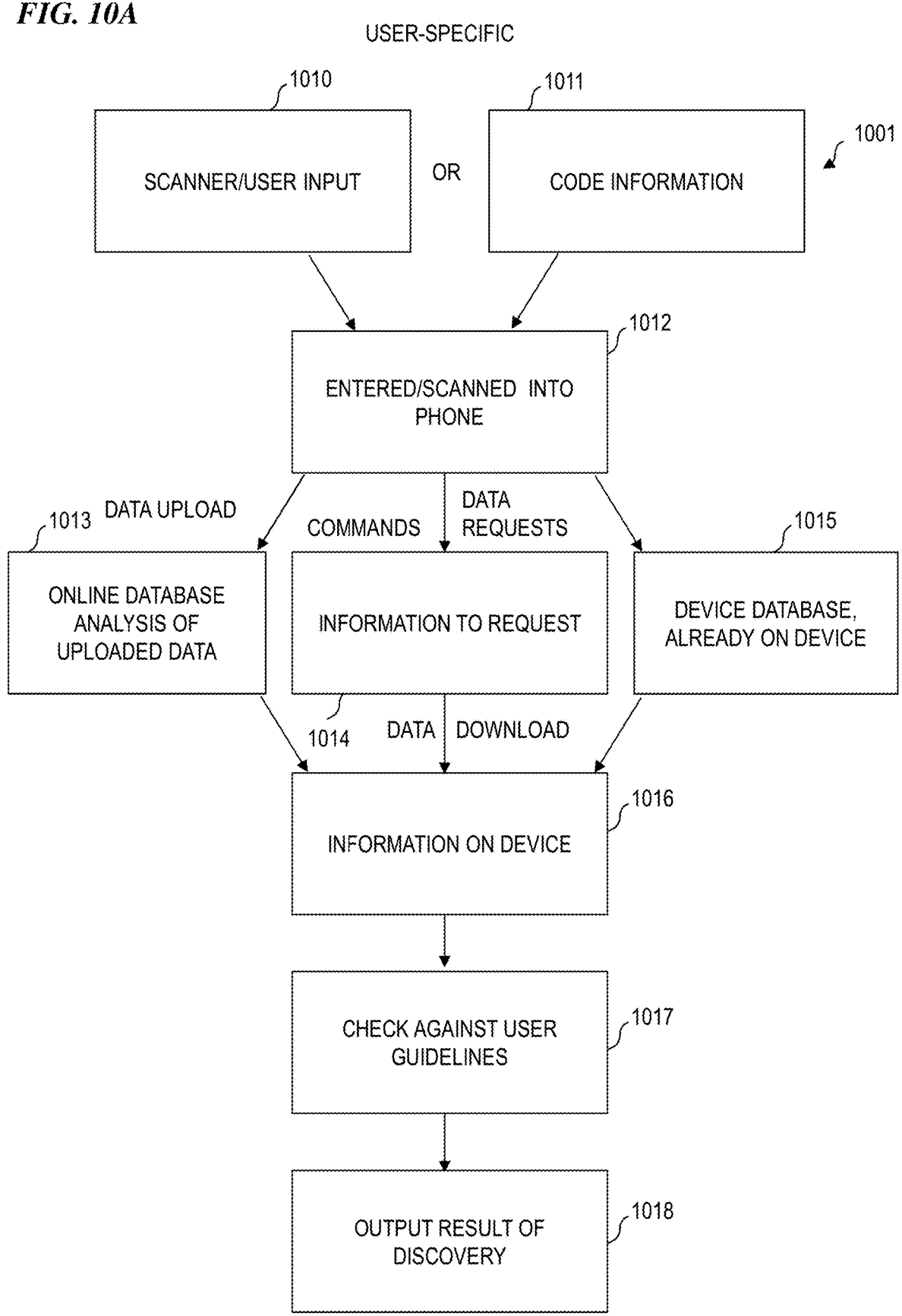
FIG. 10A is a block diagram of a method 1001 showing exemplary processing from data acquisition of the item to output to the user of information obtained and/or calculated, according to some embodiments of the invention.

FIG. 10A is a block diagram of a process 1001 showing exemplary processing from data acquisition of the item to output to the user of information obtained and/or calculated, according to some embodiments of the invention. In some embodiments, method 1001 (which can be implemented in a system that includes the user's PCD and/or other parts of system 1301 of FIG. 13A) includes block 1010 (where the system elicits and receives scanner and/or user input from the PCD 1310 (see FIG. 13A)); block 1011 (where the system elicits and receives code information (e.g., bar code or QR code) from the PCD 1310); block 1012 (where the system enters and/or scans data from the PCD 1310, and depending on the information needed, goes to block 1013, 1014 and/or 1015); block 1013 (where the system elicits and receives information from online database 1342 (see FIG. 13A)); block 1014 (where the system determines which are needed and then sends commands and data requests for information to online database 1342); block 1015 (where the system determines that the data are already in the PCD 1310 and fetches those data); block 1016 (where the system has or places the information into the PCD 1310); block 1017 (where the system checks the data versus the individual user's stated preferences and guidelines); and block 1018 (where the system outputs the results of the comparison of data versus the individual user's stated preferences and guidelines).

Figure 10B:
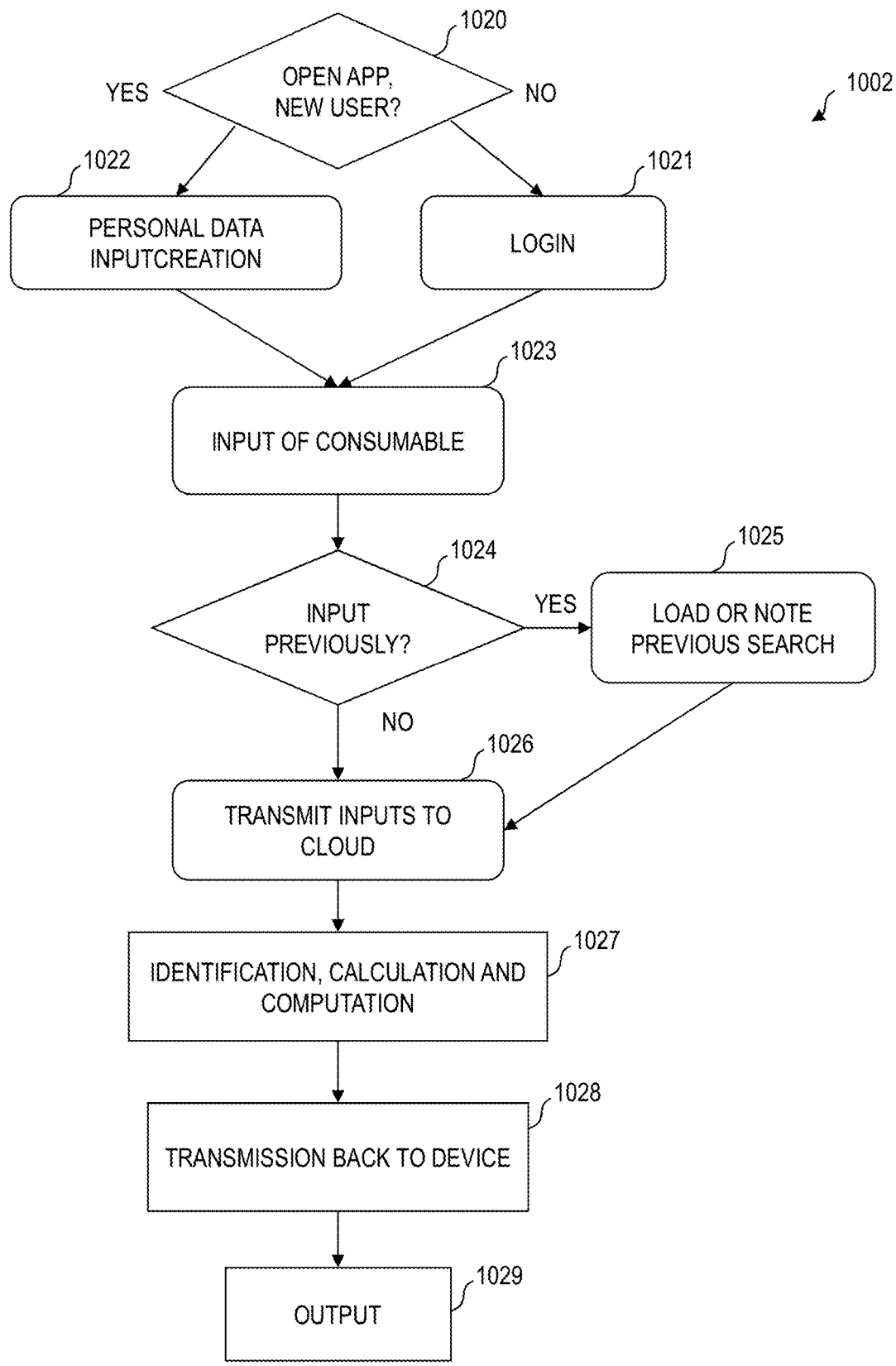
FIG. 10B is a block diagram of a method 1002 showing exemplary processing to get a new user 60 and their data entered into the system and to obtain data about a particular consumable item 80, process the user data about user 60 and the item data about the consumable item 80, and generate an output.

FIG. 10B is a block diagram of a method 1002 showing exemplary processing to get a new user 60 and their data entered into the system and to obtain data about a particular consumable item 80, process the user data about user 60 and the item data about the consumable item 80, and generate an output. In some embodiments, method 1002 (which can be implemented in a system that includes the user's PCD and/or other parts of system 1301 of FIG. 13A) includes block 1020 (where the system opens the app (application program on the user's PCD 1310) and determines whether this is a new user, and if yes goes to block 1022 and if no goes to block 1021); block 1021 (where the system collects personal and account information from the new user); block 1022 (where the system elicits and receives login information from the existing user); block 1023 (where the system elicits and receives data about a consumable item 80); block 1024 (where the system determines whether this is a new item or has been entered before, and if yes (previously entered) goes to block 1025 and if no (new item) goes to block 1026); block 1025 (where the system obtains data from a prior search); block 1026 (where the system transmits to the "cloud" e.g., a server on the internet); block 1027 (where the system calculates an identification of the item and its ingredients); block 1028 (where the system transmits to the user's PCD 1310 from the "cloud" e.g., from the server on the internet); and block 1027 (where the PCD 1310 outputs to the user).

Figure 10C:
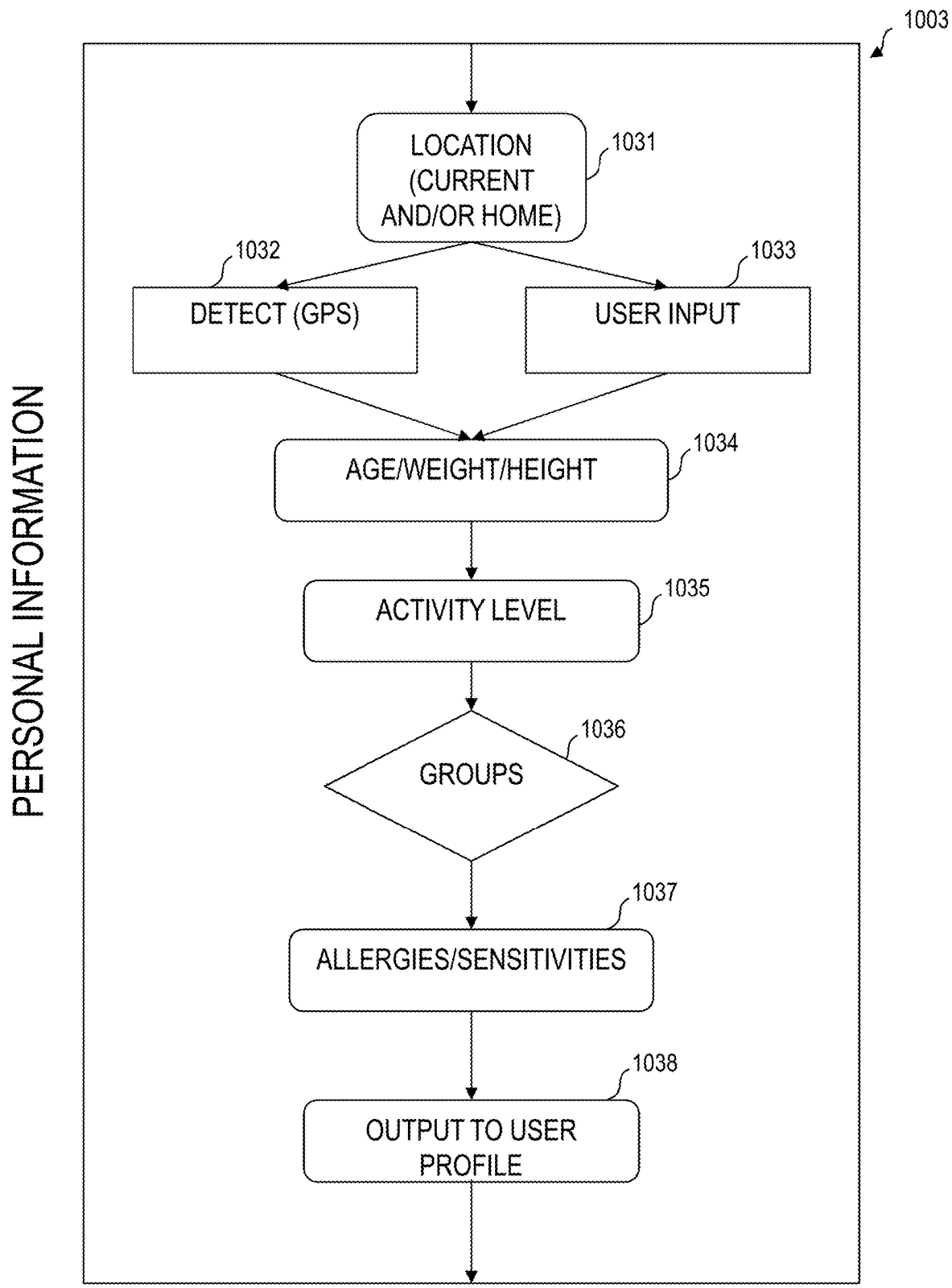
FIG. 10C is a block diagram of a method 1003 showing exemplary processing to get a location of user 60 and their personal-profile data entered into the system and to obtain data about a group or groups with which the user identifies or is affiliated.

FIG. 10C is a block diagram of a method 1003 showing exemplary processing to get a location of user 60 and their personal-profile data entered into the system and to obtain data about a group or groups with which the user identifies or is affiliated. In some embodiments, method 1003 (which can be implemented in a system that includes the user's PCD and/or other parts of system 1301 of FIG. 13A) includes block 1031 (where the system determines how the location will be determined, and if from PCD 1310's GPS subsystem gets the geo-location coordinate data at block 1032 and if no goes to block 1033 to elicit and receive the information from the user 60); block 1034 (which elicits and receives age, weight, height and like physiological data); block 1035 (which elicits and receives activity data); block 1036 (which elicits and receives or otherwise determines groups and similar data associated with subpopulations of which the user is a member); block 1037 (which elicits and receives allergy and sensitivity data); and block 1038 (which outputs the gathered data to the user profile 1338 of the user 60).

Figure 11:
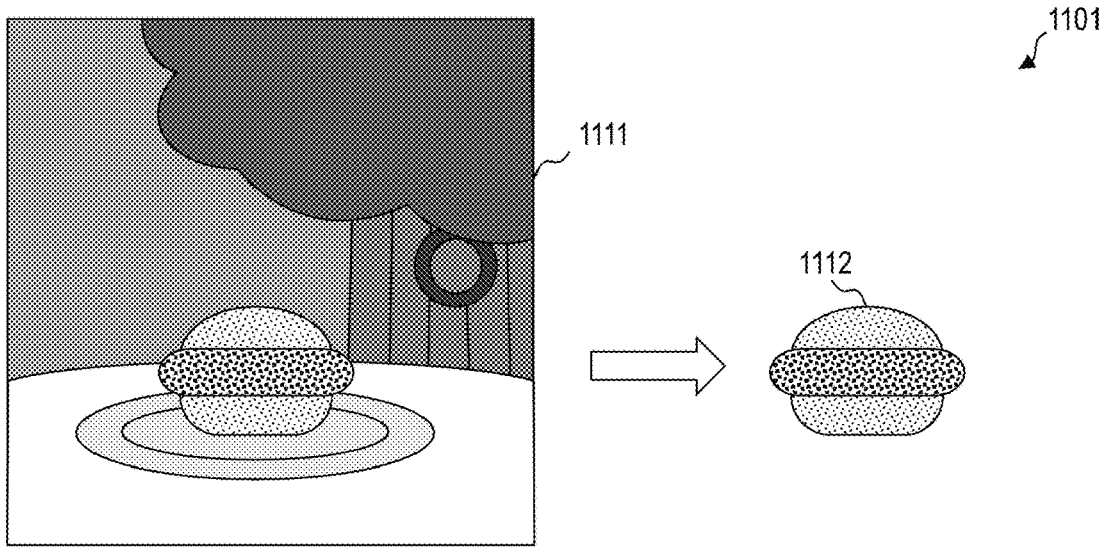
FIG. 11 is a block diagram of an example of a method 1101 for the isolation of an item in an image taken against a background, according to some embodiments of the invention.

FIG. 11 shows an example of a method 1101 for the isolation of an item image 1112 showing only the item from an initial image 1111 taken against a background, according to some embodiments of the invention.

Figure 12:
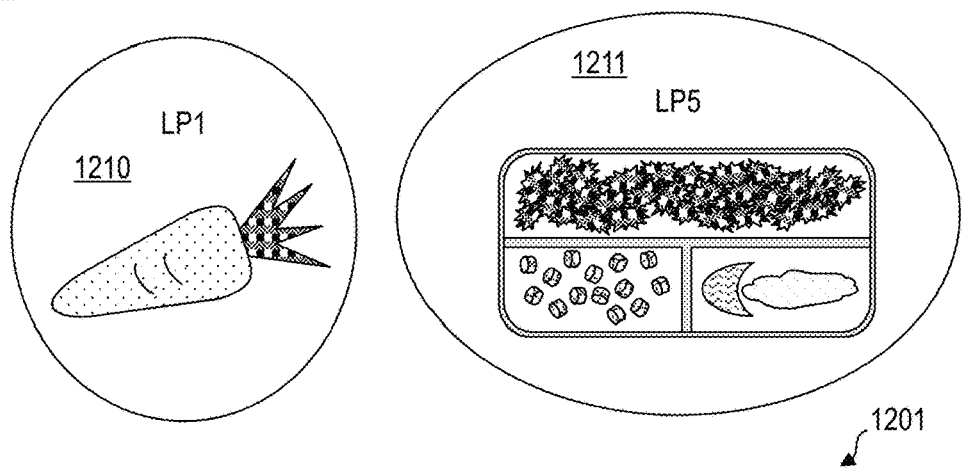
FIG. 12 is a block diagram of a method 1201 of how the classification of processing might be set up to classify different LP scores (levels of processing), according to some embodiments of the invention.

FIG. 12 is a block diagram of a method 1201 of how the classification of processing might be set up to classify different LP values (levels of processing), according to some embodiments of the invention. In some embodiments, an LP1 value (processing level 1) indicates that the food is merely picked and cleaned (e.g., as a raw carrot in a bundle of carrots at the grocery store), while an LP5 value indicates many levels of processing on many of the ingredients (e.g., as frozen TV dinner at the grocery store).

Figure 13A:
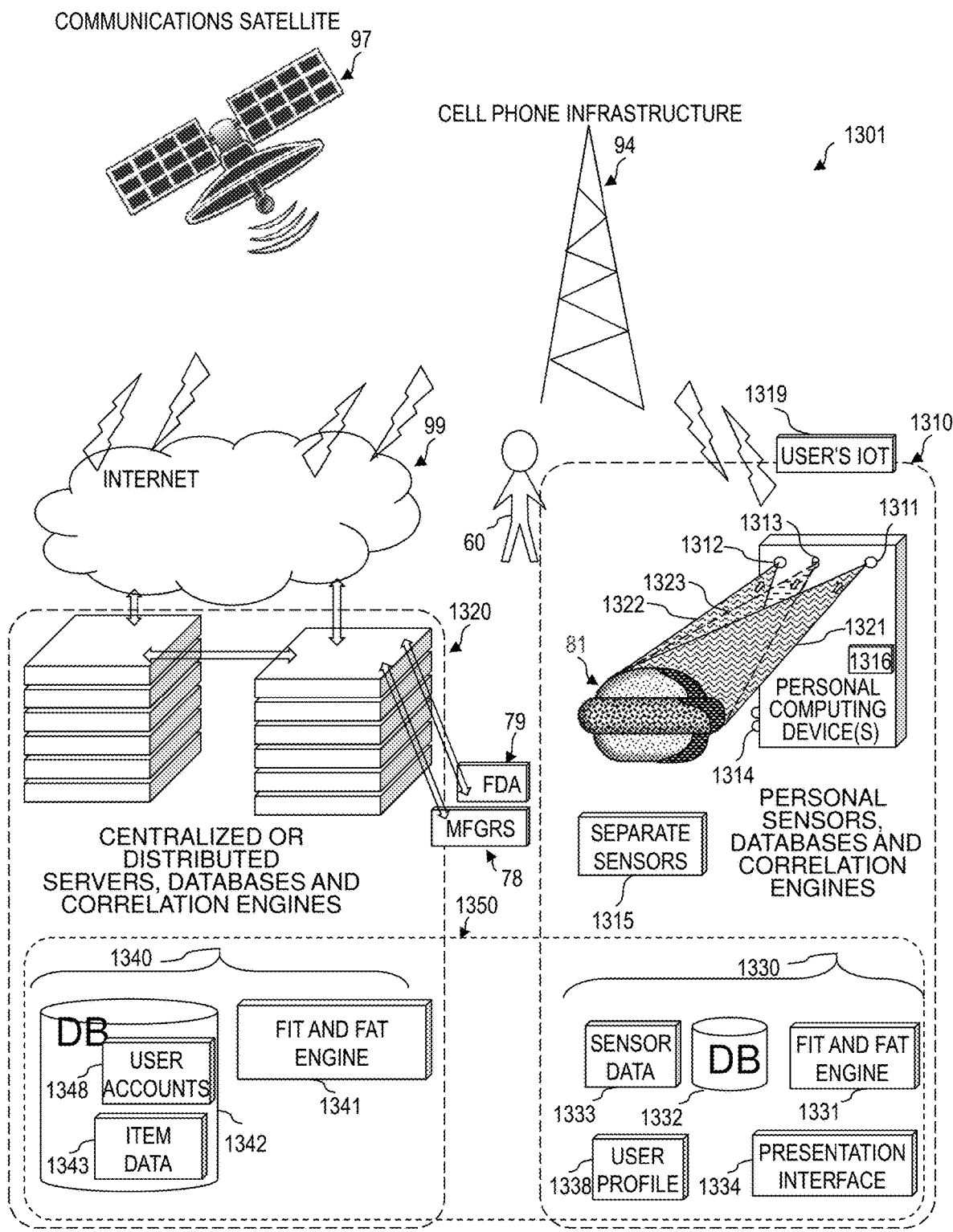
FIG. 13A is a block diagram of a FIT-and-FAT system 1301, according to some embodiments of the invention.

FIG. 13A is a block diagram of a FIT-and-FAT system 1301 for generating a FIT-and-FAT score for a consumable item 80, according to some embodiments. In some embodiments, a representation of the consumable item 80 is in an image taken by the user's PCD 1310. The block diagram of FIG. 13A may also be considered to represent the flow and storage of data and software programs of a method 1301 that executes in hardware suitable for the method. In some embodiments, system 1301 includes one or more PCDs 1310 for each one of a plurality of users, including, for example, a first user 60. In some embodiments, the one or more PCDs 1310 include household IOT appliances 1319 (such as refrigerators, microwave ovens and the like) connected as an internet of things (JOT). In some embodiments, the PCD 1310 of user 60 includes a plurality of emitting devices 1313 such as LEDs and/or lasers each emitting an optical signal 1323 different color, spectrum, linewidth or bandwidth (e.g., semiconductor lasers emit narrow linewidths, while LEDs emit colors having a wider bandwidth of wavelengths, the wavelengths being in the visible ranges between 400 nm and 700 nm or sub-portion ranges thereof, in the ultraviolet (UV) ranges between 100 nm (or shorter) and 400 nm or sub-portion ranges thereof, or in the shortwave infrared (IR) ranges between 700 nm and 2200 nm (or longer) or sub-portion ranges thereof). In some embodiments, a plurality of optical imagers and sensors 1311 and 1312 (receiving electromagnetic radiation 1321 and 1322, respectively) are sensitive to a plurality of different received wavelengths and produce images containing different data for each of a plurality of different wavelengths (e.g., producing a different image for red, green, blue, UV, shortwave IR (e.g., one or more wavelength bands between 700 nm and 1,500 nm) and/or longwave IR (e.g., one or more wavelength bands between 1,500 nm and 10,000 nm), wherein each wavelength band generates a different image. The differences between the plurality of images from each wavelength band generate data used to identify ingredients, biochemical components, allergens, and the like in the item 80.

In some embodiments, PCD 1310 includes a plurality of internal sensors 1316 such as global positioning system (GPS), accelerometers, gyroscopes, microphones, proximity sensors, magnetometers, and the like. In some embodiments, PCD 1310 includes communications systems such as Bluetooth®, near-field communications (NFC), various cell-phone bands and protocols, and the like.

In some embodiments, an external sensing device 1315 is communicatively coupled (e.g., either wirelessly or by being plugged on) to PCD 1310 to provide additional sensing capabilities that were perhaps not included or available when PCD 1310 was manufactured. Examples include FUR sensors (forward-looking infrared imagers that obtain IR images in the wavelength ranges typically from 4,000 nm to 10,000 nm; for example, such as described in U.S. Pat. No. 6,232,602 to Kerr, which is incorporated herein by reference), electrical conductivity meters, pH meters, temperature sensors and the like.

In some embodiments, PCD 1310 and/or external sensing device 1315 includes one or more sensors 1314 that, when touched to a food item 80, detect electrical conductivity (used, e.g., to estimate the amount of salt in item 80), pH (used, e.g., to estimate tartness or perhaps how well the food item 80 is cooked), density and/or size (e.g., ultrasound/sonar used to estimate calories by how dense is the food item 80, or ultrasound sonograms used to estimate a volume or amount of a serving of food item 80), temperature (e.g., thermistor data used to warn the user 60 if the item is perhaps undercooked or if the item 80 is too hot to eat right now), or even perhaps LIDAR data (light distancing and ranging used, e.g., to estimate a size of a food item).

In some embodiments, PCD 1310 includes a processor system and memory that contain software and data 1330 of the present invention. Software and data 1330 includes, for example, sensor data 1331 received from the plurality of sensors (e.g., 1311, 1312, 1314) as well as input data received from eliciting and receiving input (such as touchscreen input, voice recognition, and/or video-gesture analysis such as described in U.S. Pat. No. 9,250,746, which is incorporated herein by reference) from the user 60, a database 1333 (which contains, e.g., a history of consumable items that this user has purchased and when, and whether or not the user 60 has already consumed the item or has stored the item in a cupboard or refrigerator), a personal user profile 1338 (which contains, e.g., information as to the user's weight, height, levels of melatonin, allergies, sensitivities, nutrition requirements, food preferences, social norms and information identifying things that the user wants to avoid (such as non-Kosher, non-Halal or other impermissible foods, feed-lot beef, caged poultry, farm-raised fish, alcohol, caffeine, food raised by persons working in unsafe conditions, food processed or transported in allergen-containing equipment and the like; in some embodiments, the personal user profile 1338 on the user's PCD 1310 and/or the centrally stored personal user account 1348 of the human user 60 includes a plurality of stored parameters $X1, X2, X3, \ldots Xn$—see FIG. 13B), countries and companies that are preferred and that are to be avoided, preferences as to the maximum distance that the food items travels, and the like), a FIT-and-FAT engine 1331 that is used to calculate a FIT-and-FAT score for each consumable item 80 by weighting the benefits and detriments of each ingredient and the age and processing state of the consumable item 80 based at least in part on the factors stored in the user's user profile 1338 and/or on the factors stored in the user's user account 1348. In some embodiments, the weighting factors for each user, which are applied to the ingredients and other parameters of each consumable item 80, are stored in the user's user profile 1338 (and not shared with system 1320 or others) and/or stored in the user's user account 1348 (which can contain data that is private to each user, or, by contrast, data that is shared with other companies or used by system 1320 to direct customized advertising to each user on a user-by-user basis and/or to collect public health information (such as detecting patterns of health benefits or adverse reactions to certain foods, sources, or processing methods).

Further regarding FIG. 13A, in some embodiments, system 1301 includes a database server system 1320 (which in some embodiments, is centralized, and in other embodiments, is distributed over a range of geography and interconnection systems) is connected for two-way communications with a plurality of users 60. via the internet 99 to communications satellite(s) 97 and the cell-phone infrastructure 94. In some embodiments, database server system 1320 provides a web-browser interface used to elicit and receive information from each user 60 in order to set up accounts and customize like, dislikes, nutritive requirements and things to avoid, personal physiological information (such as weight, height, DNA markers, as well as heritage, religious preferences, cultural preferences, social preferences, groups that the user prefers to be associated with and those they prefer not to be associated with, and the like), billing and contact information and the like. In some embodiments this data obtained from each user is separately stored in each user's personal user account record 1348. In some embodiments, database server system 1320 also elicits and receives information (such as, for example, ingredients and content information, warnings, recall information, health and requirement information, effects of prolonged or constant intake of particular foods or additives, and the like) from governmental agencies 79 (such as the U.S. FDA and the U.S. Department of Agriculture, National Institutes of Health (NIH), Centers for Disease Control (CDC), and the like) and from commercial entities 78 (such as, for example, farms, food processors, meat packers, manufacturers, transportation companies, import companies, private health-research and testing companies, hospitals, and the like). This information from sources 78 and 79 is stored and continually updated in database 1342 and used to push warnings and advisories to only those particular users that may be affected by the information based on information from each user as to the types of information and warnings that they want to receive.

Some warnings may be "pushed" to devices of certain affected users regardless of their stated preferences because of the urgency and exigency of the conditions. In some embodiments, database server system 1320 further includes at least part of the FIT-and-FAT calculation engine 1341 that (alone or working with FIT-and-FAT calculation engine 1331 in the PCD 1310 of each user 60) correlates the information about each food item (ingredients, processing, source, and the like) that is about to be purchased or that has already been purchased with the personal preferences of the particular user (from user account 1348 or user profile 1338, either or both of which may contain the profile data needed) to weight the factors and to accumulate/calculate the FIT-and-FAT score to be presented to the user by the presentation interface 1334. In some embodiments, database server system 1320 further correlates warnings and recalls from the governmental agencies 79 and the commercial suppliers 78 with the consumable items each user has purchased, in order to filter the warnings and to communicate the warnings to only those ones of the plurality of users that are affected by each particular warning and recall.

Figure 13B:
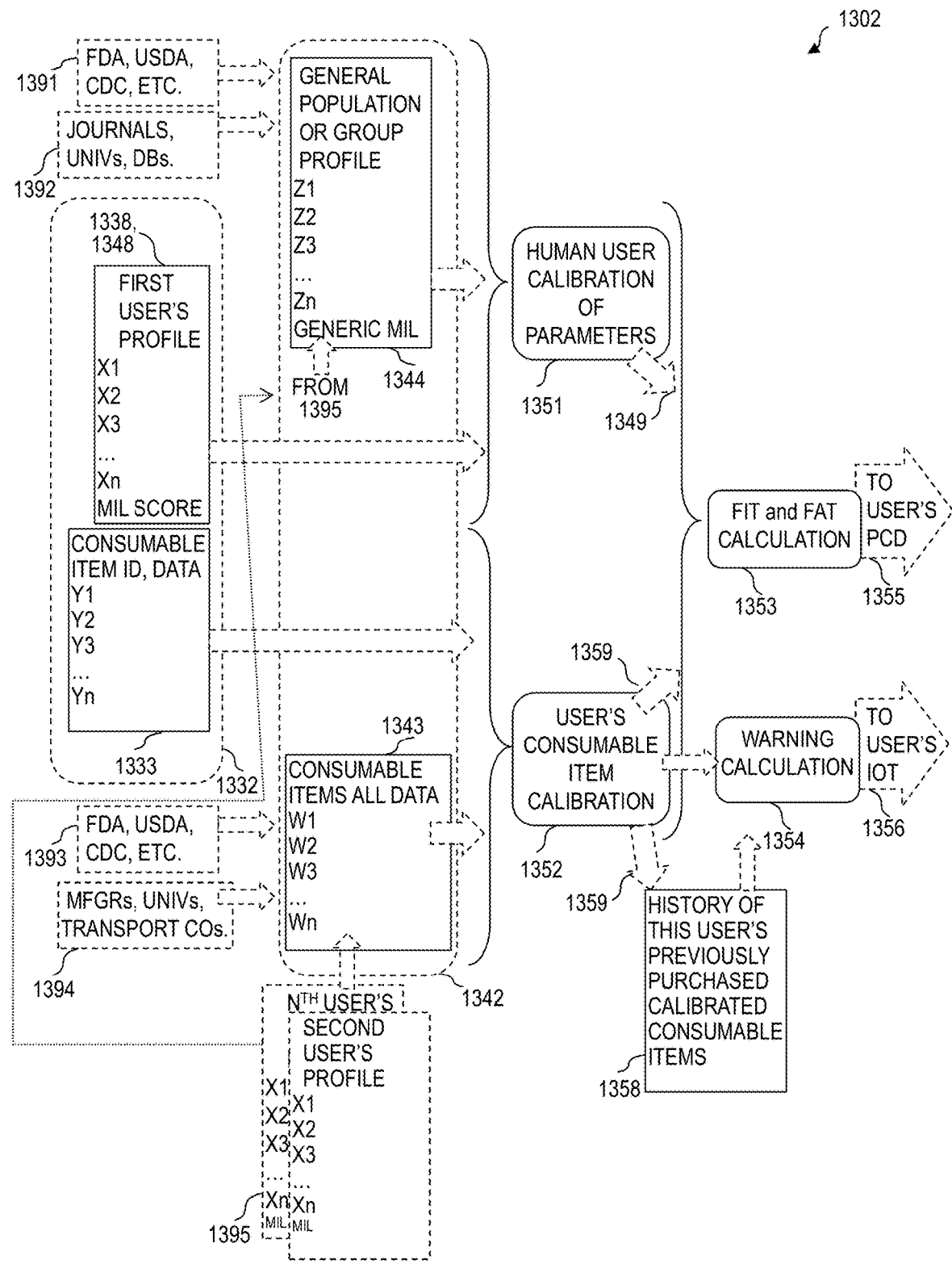
FIG. 13B is a block diagram of a FIT-and-FAT method 1302, according to some embodiments of the invention.

FIG. 13B is a block diagram of a FIT-and-FAT method 1302, according to some embodiments of the invention. The block diagram of FIG. 13B may also be considered to represent an apparatus or system 1302. In some embodiments, a generic population profile 1344 of a human person includes a plurality of parameters $Z1, Z2, Z3, \ldots Zn$ representing nutritional needs, social norms, data regarding toxins and allergies, and the like. In some embodiments, the generic population profile 1344 also includes parameter variations for specified groups such as religious taboos or requirements for specific foods or ways of preparing foods, sensitivities of persons having certain genetic heritages, and the like.

In some embodiments, system 1320 elicits and receives data for the generic population profile 1344 from government agencies 1391 (such as FDA, USDA, CDC and the like), from non-government entities 1392 (such as peer-reviewed journal, universities, specialized databases, and the like), as well as from a population 1395 of other users of system and method 1301 and 1302. Thus, process 1302 uses group-identification parameters and specific modifications and calibrations of persons in each of a plurality of groups (such as, for example, groups having "spiritual prohibitions, aversions or needs" such as, perhaps, Jews, Muslims, vegetarians and the like; and groups having "physiological prohibitions, aversions or needs" such as light-skinned persons, persons having certain allergies, and the like), wherein group-based modifications to the plurality of parameters $Z1, Z2, Z3, \ldots Zn$ are brought into consideration when a given user 60 is identified (e.g., by their personal user profile 1338, user account 1348, or by past reported reactions (positive or negative) to certain consumable items) to be a member of, or associated with, one or more identified groups. In some embodiments, user-calibration process 1351 combines and calibrates information (parameters $X1, X2, X3, \ldots Xn$) from the user profile 1338 and/or user account 1348 with information (parameters $Z1, Z2, Z3, \ldots Zn$) from the general-population or group profile 1344 to obtain a calibrated set of user-and-group parameters 1349 specific to the particular user 60.

In some embodiments, system 1320 elicits and receives data for the generic consumable-item profile 1343 from government agencies 1393 (such as FDA, USDA, CDC and the like, which may or may not be the same as the set of government entities in 1391), from non-government entities 1394 (such as company-provided information about consumable items made by each grower or processor of food or preparation items, transportation companies who may report when they received and when they delivered a shipment of goods, peer-reviewed journal articles, universities, specialized databases, and the like), as well as from a population 1395 of other users of system and method 1301 and 1302. In some embodiments, consumable-item-calibration process 1352 combines and calibrates information (parameters $Y1, Y2, Y3, \ldots Yn$) from the consumable-item data 1333 regarding a specific item that the first user 60 is presently contemplating (such as information elicited and received directly from the user (typed in or received from voice-recognition dictation subsystems) and/or data from the sensors in the user's PCD 1310) with information from the database information (parameters $W1, W2, W3, \ldots Wn$ about each consumable item 80, which, in some embodiments, include parameters for adjusting weights of parameters $W1, W2, W3, \ldots Wn$ based on specified characteristics (parameters $Z1, Z2, Z3, \ldots Zn$) of identified subgroups of the general population as identified in the data 1344) regarding all known consumable items 1343 to obtain a calibrated set of specific-consumable-item parameters 1359 specific to the particular consumable item 60 (referring again to FIG. 13A).

In some embodiments, warning-calculation process 1354 performs calculations based on the presently considered item 80 (to provide warnings and/or suggestions for alternatives that are better suited to this first user 60) as well as on items in the stored history 1358 of this user's previously purchased consumable items (e.g., not-yet-consumed consumable items that may yet be in the refrigerator or cupboard of the user 60), and warning-calculation process 1354 outputs (in some embodiments, pushes without an explicit current inquiry or request from user 60) warning 1356 to the user's PCD 1320 and/or to one or more of the IOT appliances 1319 of user 60. For example, the FDA (e.g., in the set of entities 1393) or some company (e.g., in the set of entities 1394) may send out a product-recall notice that a particular batch of hundreds of thousands of pounds of curry has lead (Pb) contamination, but the notice is sent out after the affected products have been sold and those products (e.g., items containing mostly, meat, vegetables or rice) would not specify which kind or source of curry was used in preparation of the items. It is impractical for all consumers to receive all possible such notices, nor for the consumers who do receive these notices to figure out which of the hundreds of items in their personal inventory might have curry. Such a notice does not affect all curry, nor do all consumable items contain curry. In some embodiments, method 1302 thus filters the notice based on which products were made from the contaminated batch, and on whether this particular user 60 purchased any of the affected products in the past, and only sends warning 1356 to this particular user's IOT appliances 1319 only if the history 1358 indicates that such a purchase was actually made (based on data actually received by PCD 1320) or was probably/possibly made (based on a pattern of past purchases by this particular user 60 or by a group in which this user 60 is a member. As a result, an IOT-connected refrigerator of this particular user 60 can then immediately flash a warning to this particular user 60 identifying exactly which item is affected so that the user 60 can dispose of the item, or, if the item has been consumed, the user can go to a doctor to obtain treatment or can obtain other items that can remedy the problem.

In a like manner of some embodiments, FIT-and-FAT-calculation process 1353 performs calculations based on the presently considered item 80 to provide warnings and/or suggestions for alternative items (e.g., alternative items having fewer calories or more nutrients) that are better suited to this first user 60, and/or supplemental items (e.g., items having missing nutrients, items having ingredients that counteract detrimental properties of the contemplated item, and/or items that together with the contemplated item 80 would provide a more nutritious and delicious meal)). FIT-and-FAT-calculation process 1353 then outputs the recommendations and information 1355 to the user's PCD 1320. In some embodiments, all, or various portions of the data 1338, 1348, 1333, 1344, 1343 and 1358 are stored on either the user's PCD 1310 or on the servers and databases 1320, or both. In some embodiments, all, or various portions of the processes 1351, 1352, 1353, and 1354 are performed on either the user's PCD 1310 (e.g., by FIT-and-FAT engine 1331) or on the servers and databases 1320 (e.g., by FIT-and-FAT engine 1341), or both.

To evaluate the consumable, the system 1301 and method 1302 use sensor data and data received from the user to more precisely identify the consumable. In some embodiments, this is done using data that is elicited and received from the user and/or by information gathered from sensors in and/or connected to the device.

In some embodiments, sensor data 1331 include data from a plurality of input sensors inside the personal computing device 1310 of each human user (such as GPS, optical-image cameras 1311, IR and/or UV imagers 1312, electrical-conductivity sensors and/or pH sensors 1314, sound and ultrasound sensors, DNA sequencers, and the like), sensor systems in separate devices 1315 (such as smart watches or dedicated sensor devices) that communicate wirelessly to the personal computing device 1310 of user 60, database devices 1333 communicating with or connected to the device 1310, or otherwise used on an item 80 to be consumed. In some embodiments, this input sensor data 1331 includes visual, auditory, microbial and/or a plurality of other different inputs.

Figure 14:
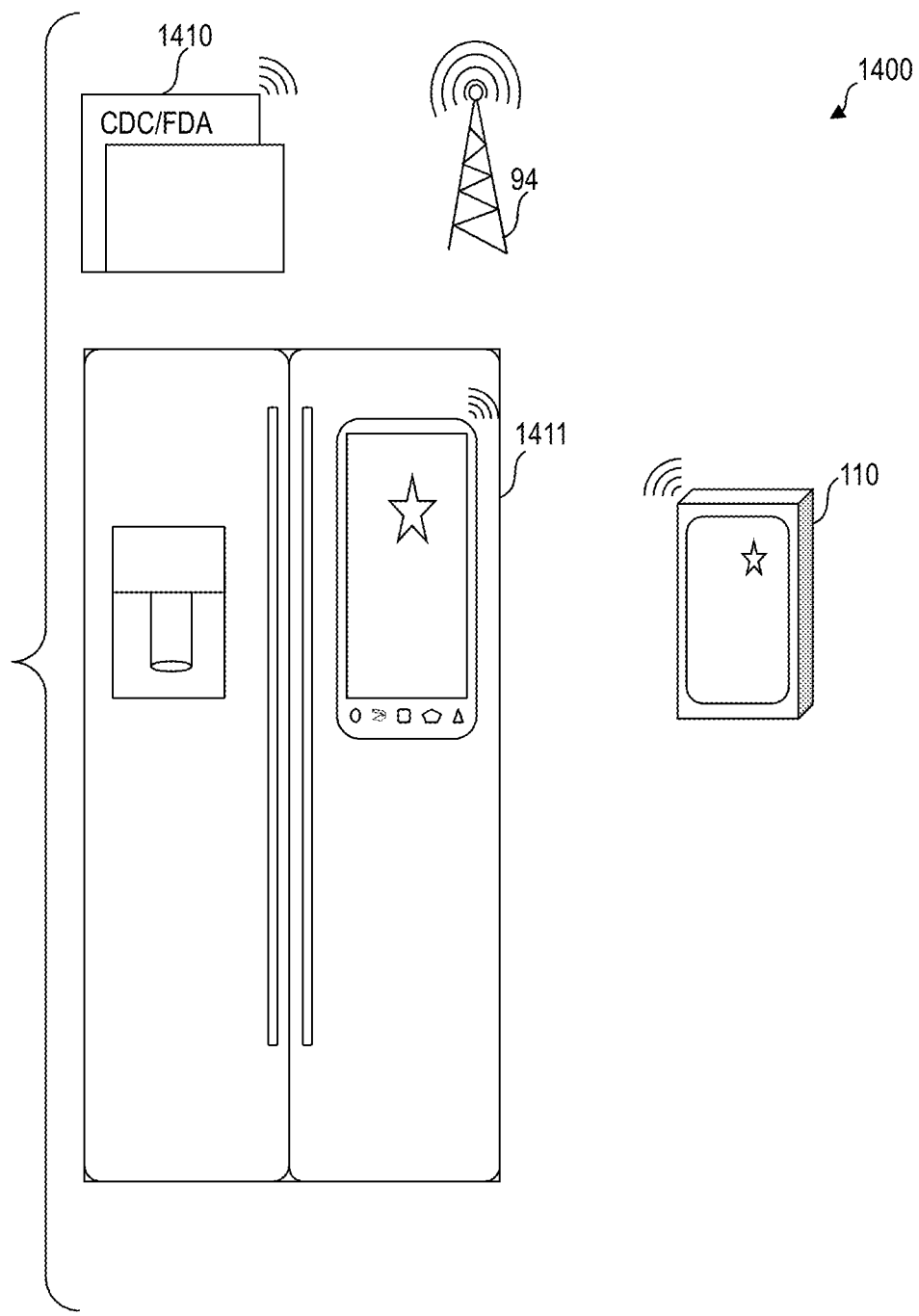
FIG. 14 is a block diagram of a system 1400 that updates and alerts the IOT devices of user 60, according to some embodiments of the invention.

FIG. 14 is a block diagram of a system 1400 that updates and alerts the IOT devices of user 60, according to some embodiments of the invention. In some embodiments, system 1400 includes reception of alerts, recalls and warnings from the FDA, CDC, manufacturers and the like 1410, which periodically transmit such data across the internet 99 and then through the cellphone wireless network 94 to the user's device 110 (sometimes implemented by PCD 1310) and/or to the user's IOT including IOT-enabled refrigerator 1411.

Figure 15:
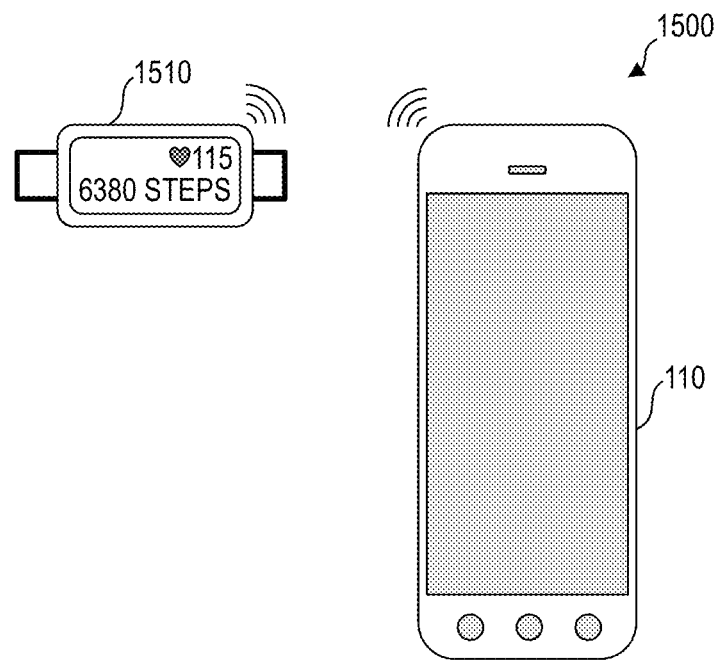
FIG. 15 is a block diagram of an interconnected system 1500 that includes a plurality of wirelessly connected, personally carried PCDs of user 60, according to some embodiments of the invention.

FIG. 15 is a block diagram of an interconnected system 1500 that includes a plurality of wirelessly connected, personally carried PCDs of user 60 (e.g., such as wrist-mounted exercise detector 1510 (or a subdermal implanted system—not shown—such as a heart pacemaker, insulin pump or the like) and smartphone device 110), according to some embodiments of the invention.

Figure 16:
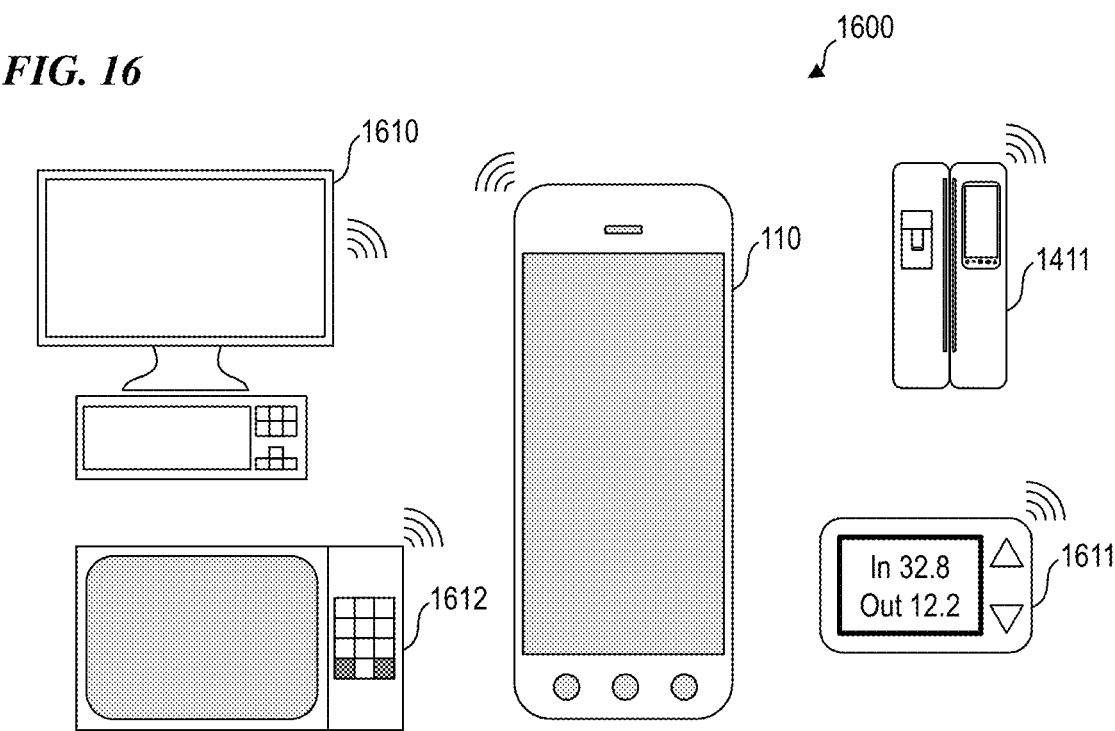
FIG. 16 is a block diagram of an interconnected system 1600 that includes a plurality of IOT (internet-of-things) devices of user 60, according to some embodiments of the invention.

FIG. 16 is a block diagram of an interconnected system 1600 that includes a plurality of IOT (internet-of-things) devices of user 60 (e.g., such as personal computer 1610, IOT-enabled microwave oven 1612, IOT-enabled refrigerator 1411, thermostat/security alarm system 1611, smartphone device 110 and the like), according to some embodiments of the invention.

FIG. 17 is a table of features, some or all of which are combined and used in some embodiments of the invention. The features are as set forth in FIG. 17, and described elsewhere in this specification and the other Figures.

In various embodiments of the present invention, the user's device 1310 and/or central server 1320 performs one or more of the following functions:

In some embodiments, the user's personal device 1310 provides an indication (visual, audio or tactical) to the user of a consequence or a recommended alternative to consumption of a particular item.

In some embodiments, the system 1300 uses spectroscopy, either by Raman scattering or other suitable technology, as provided by one or more sensors 1311, 1312, 1314 and the like in the user's PCD 1310 or auxiliary supplemental sensor system(s) 1315.

In some embodiments, camera 1312 of system 1300 obtains data printed on the item, and receives data, such as using recognition of images though OCR, Barcodes, QR codes and the like that are printed on or supplied with the consumable items 80.

By taking a digital image with a plurality of colors (in some embodiments, including UV, visible (e.g., blue, green and red), and short-wave and/or long-wave IR) and/or obtaining a spectrum of the food item 80, some embodiments of the present invention decipher the presence of a targeted allergen, for example, by analysis of one or more of the following: Raman scattering and/or Brillion scattering (illuminating the food item with laser light and detecting Raman-shifted and/or Brillion shifted wavelengths in the light received back from the food item), hue, saturation, and intensity of a population of pixels, such as described in Landwehr et al.'s U.S. Pat. No. 7,496,228, or methods such as described in U.S. Pat. No. 9,212,996 or 9,291,504 which are all incorporated herein by reference. Some embodiments use volumetric measurements such as described in U.S. Pat. No. 9,250,746 to Shafa Wala, which issued on Feb. 2, 2016, as well as U.S. Pat. Nos. 8,897,539, 8,855,406, U.S. Patent Publication No. US2013/0083990 and PCT Publication No. WO2013/173383, which are each incorporated herein by reference.

In some embodiments, system 1300 and its associated method identify consumables and compute information on the item 80. Some examples of the computation include: computing information on the object (type, ingredients, age, geographic source, processing that was incurred, travel route from dirt to table, and the like), Identify presence of a targeted allergen, and elicit and receive input from the user as to identity of the food, and to elicit and receive image(s) from the user, then locate within the image, and perform optical character recognition (OCR) on, ingredients list of packaging.

In some embodiments, system 1300 and its method compute the volume of a consumable; in some embodiments, with methods and devices such as described in U.S. Patent Publication US 2011/0225534, as well as U.S. Pat. Nos. 8,897,539, 8,855,406, U.S. Patent Publication No. US2013/0083990 and PCT Publication No. WO2013/173383, which are each incorporated by reference.

In some embodiments, system 1300 and its method take a plurality of images using different spectra to identify components and ingredients though image spectrograph/histogram in a method similar to that described in U.S. Pat. No. 7,496,228 to Landwehr, et al., which is incorporated herein by reference.

In some embodiments, system 1300 and its associated method identify volume, substances and composition of item 80 though sonography/sonographic imaging/volumetric measurement (sonograms).

In some embodiments, system 1300 and its associated method using spectroscopy (e.g., fluorescence, Raman spectroscopy, microwave spectroscopy, near IR etc.) to identify consumables, components, ingredients, temperatures, biochemical signatures, and other properties of a consumable such as how well an item has been cooked. In some embodiments, the data regarding components, ingredients, biochemical signatures and the like are communicated to the central database system 1320, which then uses the communicated data to look up possible detrimental or beneficial aspects of consuming the item in its present state (age, how well it is cooked, presence of allergens, and the like), and then send the results back to the PCD 1310 of the particular user 60.

In some embodiments, system 1300 and its associated method take multiple images in different spectra of light (e.g., in some embodiments, infrared, visible, and/or ultraviolet light) to identify food items and components in it. In some embodiments, the data regarding infrared, visible, and/or ultraviolet light and fluorescent light and the like are communicated to the central database system 1320, which then uses the communicated data to look up possible detrimental or beneficial aspects of consuming the item in its present state (age, how well it is cooked, presence of allergens, and the like), and then send the results back to the PCD 1310 of the particular user 60.

In some embodiments, system 1300 and its associated method identify food from its:

a. spectroscopy, hue, saturation used to determine freshness, contamination and the like;
b. barcode/QR-code/linear and matrix barcodes;
c. restaurant or grocer from which the item was bought (identification of a particular restaurant or grocery establishment provides additional data elucidating the ingredient mix typically used by that establishment, as well as the typical nutrients, concentration of oxidized molecules (e.g., peroxides), total caloric content and the like in the restaurant's meals (including salad dressings and desserts) and the source and transport distance of the ingredients in the mix. Each establishment will produce a different version of a particular end product that is otherwise conforming to the named produce (e.g., a "hamburger"). These restaurant-or-grocer data can be particularly important or disregarded, depending on the particular user, and thus each user's profile 1338 of desired or to-be-avoided ingredients is used differently (user-to-user) to weight the FIT-and-FAT score. For example, if a given user is overweight, the data that a particular restaurant serves meals having higher-than-average caloric content would be used by that user's PCD to recommend that the user should minimize patronizing that restaurant or that the user should limit the portions consumed;
d. the original or private-label firm marketing the item (to ascertain users the desirability of OFM (Original food producer/Farmer/Manufacturer);
e. identify the countries in which the item was produced and re-assembled or traveled through (to ascertain that the source country had hazard analysis and critical control points (HACCP) systems in place that conforms to U.S. regulatory standards (e.g., from the FDA and U.S. Department of Agriculture) and import quotas from the U.S. Department of Commerce, particularly for meats and milk, so the public does not end up having imports of un-reliably processed meat. milk products, and produce with higher-than-allowed pesticide levels);
f. identify presence of unwanted compounds via sniff test (via information from an odor detector, breathalyzer, and the like); certain food items that have aged emanate certain volatile fatty acids that inherently diminish the "deliciousness" of the food (wherein "deliciousness" can be defined as the attractiveness of taste as well as the ability of the food to meet some nutritive need of the consumer);
g. branding/labeling (e.g., logos or recognition of a product by a tradename such as a Big Mac®)

In some embodiments, system 1300 and its associated method detect and identify real and natural versus synthetic flavorings under government-blessed USDA or FDA labels, or by OCR of an ingredient list on the packaging.

In some embodiments, system 1300 and its associated method attach to the phone to assist in sensing various data about the consumable.

In some embodiments, the human user inputs information about themselves or the items they are considering for consumption. For the user, this may include, but is not limited to, the user's weight, age, dietary restrictions or requirements (e.g., gluten-free diet, vegetarian, iron deficiency), activity level, hometown (for water supply data and other environmental information), or travel regimen. For the consumables, these may include, but are not limited to: name of the item, name of purchasing vendor, approximate size of serving being used, and so on.

In some embodiments, the present invention includes a device and method to take in user-specified information about the user (e.g., body-mass index (BMI), weight, age, height, etc.), In some embodiments, the device and method elicits and receives information from and about the user to use in computation of the likely effect, both short term and long term on the user's health, vitality, longevity, and the like.

In some embodiments, system 1300 and its associated method obtain the number of steps taken from, e.g., a pedometer.

In some embodiments, system 1300 and its associated method elicit and receive from the user exercise data.

In some embodiments, system 1300 and its associated method obtain fitness data from an external device, e.g., Fitbit®, Google Moves®, etc.

For some embodiments, once input has been obtained, one or more of the following methods are used as part of the present invention to identify the item(s).

In some embodiments, system 1300 and its associated method perform a "proximation" determination (e.g., provide the estimate or closest alternative: display or otherwise present to the user the closest "guesses" as to the food and its ingredients and elicit and receive input from the user to select which one) by ingredient, (again, in some embodiments, fuzzy algorithms such as described in U.S. Pat. No. 8,055,599 to Werth, which is incorporated herein by reference, are used to find closest match using adjacent and fuzzy hashes.)

In some embodiments, ingredient-information input is elicited and received from the user into system 1300, by the user's personal device 1310, and transmitted to the central database 1320 to have the database 1342 (sometimes called a knowledge-nutrition database (KDB)) of the present invention look for information on the identified consumable ingredients and methods that the user 60 will cook or prepare with (such as boiling in water or oil, frying, broiling, heating over charcoal, pickling, marinating or the like), as well as cosmetics and other skin-applied products, IV-supplied nutrients, parental nutrition, enteral (feeding or drug administration by the digestion process of a gastrointestinal (GI) tract), and per-Os (oral administration) or nil-per-Os (administration via rectum) nutrition.

In some embodiments, system 1300 and its associated method capture sensor information regarding a consumable and send the information along with a request for further information to other consumers (e.g., to obtain information from a crowd-sourced resource), and/or to searchable databases maintained by sellers, producers, and manufacturing companies, NGOs, universities, or government agencies, in order that the sensor information is used as a search request for further information about the item.

In some embodiments, the present invention includes a device and method to use social media for identification of an item. For example, Instagram® or the like could send out an inquiry as to "what is the item in this photograph, or conversely, could be used to disseminate information from one's group of friends or like-situated individuals as to certain desirable or undesirable ingredients in a particular food item using the item's QR code or other identification means.

In some embodiments, the present invention includes a device and method to determine whether majority of some food actually is the food it is purported to be (is it meat? where's the beef?)

In some embodiments, system 1300 and its associated method determine the age of food, e.g., sell-by-date vs. actual age of item.

In some embodiments, system 1300 and its associated method determine the age-from-picking of a food (e.g., using a given rule for freshness of food that may contain several ingredients, each having a different harvest date).

In some embodiments, system 1300 and its associated method determine the origin, manufacturer, and processing of an item from "dirt to dinner table."

In some embodiments, system 1300 and its associated method use background image information (the image data of the scene that surrounds but does not include the item of interest) to identify relevant foods or businesses.

In some embodiments, system 1300 and its associated method use background information (information previously entered by the user about themselves) along with the currently received data about the consumable item being contemplated to elicit further information from the user about the user or the item.

In some embodiments, system 1300 and its associated method use pattern recognition to identify similar images for identification of the item In some embodiments, system 1300 and its associated method use databases of information to help identify products, calculate information, streamline processing and various other things to assist in the operation of the process.

In some embodiments, system 1300 and its associated method compare and identify a chosen consumable item 80 against known databases of consumables (in some embodiments, a method such as described in U.S. Pat. No. 8,055,599 to Werth that issued Nov. 8, 2011 with the title "Pattern recognition using cycles or traces in an associative pattern memory (APM), vertical sensors, amplitude sampling, adjacent hashes and fuzzy hashes," and which is incorporated herein by reference).

In some embodiments, system 1300 and its associated method use an on-device database against which to compare consumable, and in which to store data on device to make comparisons.

In some embodiments, system 1300 and its associated method provide to the user the ability to access and use external databases (for example, databases from or in use by pharmaceutical companies, the government, or food-producing companies, etc.) in addition to, or as a substitute for, the internal database 1342 that the invention itself maintains, with the data of the present invention or crowd-sourced data and the user-specific data for each user 60.

In some embodiments, system 1300 and its associated method have a database that is accessed by the user's device 1310 to determine country/locale/corporation policies on file for users to decide upon as to whether to use a particular consumable (e.g., EPA, chemical dumping, gas mileage, food-generated green-house gasses, and the like).

In some embodiments, the user's device 1310 and/or central/distributed server DB (database) 1320 is queried to obtain and estimate or describe greenhouse impact (e.g., $CO_2$) using methods from peer-recognized articles. In some embodiments, the resulting data is then used to weight one or more factors used in calculating the FIT-and-FAT score.

In some embodiments, data for calculations are spread across and result data are obtained back from a plurality of servers, distributed computing, optimizers, and/or other computational devices (e.g., devices "in the cloud" and connected to the internet).

In some embodiments, system 1300 and its associated method provide comparisons or alternatives for items being considered for use or consumption.

In some embodiments, system 1300 and its associated method identify predetermined substances by analyzing incomplete data (input by user) such as generic term for a type of food that is used to determine ingredients usually used to make that food; or In some embodiments, system 1300 and its associated method differentiate identically priced/identified products: show the user what is the difference In some embodiments, system 1300 and its associated method provide suggestions to the user for alternative and/or cost-efficient items for consumption that are available.

In some embodiments, system 1300 and its associated method compare two or more products and the overall impact of each on health and which will most likely be aligned with user preference (as to environment (soil erosion), social (GMO or vegetarian), religious (Kosher or Halal), community (group peer pressure) other factors).

In some embodiments, system 1300 and its associated method determine which consumable to buy as an optimal buy (best use of your money, cumulative differences between nearly-identical foods or cosmetics). In some embodiments, this is implemented, at least in part, as an "app" on the user's device.

In some embodiments, a table of data such as the following is presented to the user 60, from their PCD 1320, displaying a comparison of a selected food item to alternatives that may be more beneficial, less detrimental, equal in benefit but more delicious or less costly, and the like. Note: In some embodiments, the preferences, benefits or detriments are defined by the user 60 and/or with information obtained from a commercial company or government agency.

In some embodiments, the Table 1 includes a plurality of alternative foods and such factors as: effect on the user's aging, deliciousness, freshness, nutrient quality, point of origin, allergens (physiological), allergens (spiritual), natural ingredients, antioxidants, rancidity, Caloric density, preservatives, salt, propionic acid, acidity or alkaline pH, and the like.

TABLE 1

| effect on aging | deliciousness | freshness | nutrient quality | point of origin | allergens (physiological) | allergens (spiritual) | natural ingredients | antioxidants | rancidity | Caloric density | etc. |
|---|---|---|---|---|---|---|---|---|---|---|---|
| Food 1 | | | | | | | | | | | |
| Food 2 | | | | | | | | | | | |
| Food 3 | | | | | | | | | | | |

In some embodiments, system 1300 and its associated method elicit and receive data on specific ingredients with certain nutritional values and suggest items that would provide user with these items inherently or organically. For example, the system 1300 may suggest different specific foods to obtain a particular beneficial substance such as omega-3 fatty acid: such as flax seeds (containing organically inherent omega-3) versus chicken that has been fed flax seeds or other sources in order to augment its omega-3. Such chicken would have other beneficial components such as protein.

In some embodiments, system 1300 and its associated method use location information (such as the GPS location of PCD 1310) of the user to determine a consumable and purchasing/usage area to help identify the item and local geographic environmental factors that affect the weightings of ingredient factors and user-profile factors.

In some embodiments, system 1300 and its associated method elicit and receive information from user 60, which allows the user 60 to identify or choose to manually input default (or overriding) location information or to have the user's location automatically acquired (e.g., via GPS of current location). In some embodiments, system 1300 and its associated method use this information to identify or choose local factors and sources, (e.g., local water quality and which store to patronize).

In some embodiments, system 1300 and its associated method elicit and receive purchase location or current location data from PCD 1310 itself or from user input into device 1310.

In some embodiments, system 1300 and its associated method elicit from the user a food or specific item the user would like to obtain and give local sources In some embodiments, system 1300 and its associated method search for manufacturers and consumer stores (e.g., organic (innate or inherent) Omega-3 chicken, filets.)

In some embodiments, system 1300 and its associated method elicit location data from the user or device to assist in operation of the invention In some embodiments, system 1300 and its associated method use location data to assist in identifying information (e.g., if the user is at a McDonald's® restaurant, the present invention limits the search to foods from McDonald's®.)

In some embodiments, system 1300 and its associated method use location data to identify water quality and components, and then use that data regarding the quality and components of the local water to adjust the FIT-and-FAT scores of food made with or boiled in the water.

In some embodiments, system 1300 and its associated method elicit altitude data (e.g., Denver vs New Orleans), and then use that altitude data to adjust the characteristics of food prepared at the determined altitude (e.g., water boils at a lower temperature at high altitudes and thus food items that are prepared by boiling for a given period of time will be less-well-cooked than at lower altitude; so in Denver, Colo., USA, which is at an elevation of about one mile, water boils at approximately 95 degrees C. (or 203 degrees F.); depending on the type of food and the elevation, the boiling water may not be hot enough to cook the food properly unless the time is lengthened).

In some embodiments, system 1300 and its associated method identify food produced within a reasonable distance of consumption. For example, food consumed in Paris (France) and produced in Japan may be considered to be (depending on the type of food and the processing performed before transit) not a reasonable distance due to certain chemical changes in foods due to extended storage time during transit as well as transit time.

In some embodiments, system 1300 and its associated method identify travelling food merchants (farmer's markets) or food trucks.

In some embodiments, system 1300 and its associated method use crowd-sourcing methods for a plurality of methods including but not limited to information gathering, processing distribution, and identification.

In some embodiments, system 1300 and its associated method identify an item (as described herein), wherein the user device transmits/sends a request and relevant data and/or image(s) to a crowd-sourced resource (internet-based server that presents questions to the crowd in order to elicit and receive information for identification (in some embodiments, a group-inclusion method is used such as described in U.S. Pat. No. 8,166,026 to Sadler, which is incorporated herein by reference).

In some embodiments, system 1300 and its associated method differentiate products via expert opinion(s) or crowd opinions (distinctive product characteristics and experiences from anywhere around the world)

In some embodiments, system 1300 and its associated method track prices and rates of consumables by using methods and devices such as described in US Patent Publication 2008/0172244 titled "Systems and Methods for Displaying Current Prices, Including Hotel Room Rental Rates, With Markers Simultaneously on a Map", which is incorporated herein by reference.

In some embodiments, system 1300 and its associated method use social media to track trends in and individual's eating, or trends of an individual or group In some embodiments, system 1300 and its associated method calculate the effect of a consumable on a user's overall health In some embodiments, system 1300 and its associated method compute the impact of consumables on user's baseline (health and aging)-positive, negative, or neutral.

In some embodiments, system 1300 and its associated method determine the ratio of current weight of the user over a calculated future mature weight of the user is a mathematical relationship for the desirability of consumption of item (as desirability or "deliciousness") and rate of caloric intake (total calories per lifetime of a human could be, perhaps, a total of about 60 million to about 90 million food calories (depending on location, occupation, exercise and genetics), rate of its use can affect longevity. For example, a person consuming an average of 2000 Calories per day times 365 days per year times 82 years results in the person consuming 59,860,000 Calories over their lifetime, while a person consuming an average of 2750 Calories per day times 365 days per year times 90 years results in 90,337,500 Calories, and a person consuming an average of 3000 Calories per day times 365 days per year times 57 years is 60,225,000 Calories. This can create a lifetime Calorie clock, and the present invention can provide to the user a running total of calories, wherein certain research indicates that restriction of food calories leads to extended lifetime.)

If an animal severely restricts caloric intake on a particular day, that animal's efficiency of caloric intake on the following day is increased, and thus the "effective" caloric rate for the intake on the latter day would be increased. In some embodiments, the present invention takes into account the caloric intake of each day as calibrated by one or more prior-days caloric intake and then calculates an accumulative caloric intake rate over months or years to provide an estimate of average past caloric intake and estimate of likely remaining lifetime. In some embodiments (because every user likely will not bother to track every food item consumed every day), the approximate caloric intake is estimated by the present invention based on ethnic background, height, age, weight (and change in weight over time), exercise, occupation or exertion per day or per week by the user, the user's locality (including climate, latitude, altitude and the like), and is calibrated as needed by whatever input the user provides as to actual tracked food items consumed. This calibrated approximate caloric intake is then tracked and presented to the user either directly (accumulated calories consumed over weeks, months or years) and/or indirectly as an input to the recommendations as to what food items the user should consider as alternatives or supplements to what the user is contemplating (e.g., telling the user that their recent caloric intake has been too high (as compared to what the user has inputted to the system as their preferred or desired rate of caloric intake), and thus the system suggests/recommends some number of (e.g., in some embodiments, five or so) alternatives such as a lower-calorie salad or other healthy food rather than a high-calorie hamburger, milkshake and fries). In some embodiments, the suggestions are provided as enticing photographs of the suggested alternative food items. The suggested recommendations as to what food items the user should consider as alternatives or supplements is a benefit provided by the present invention to the user.

In some embodiments, system 1300 and its associated method chart the effect of amount and intensity or concentration of a consumable on a child's maturation and growth.

In some embodiments, system 1300 and its associated method chart the effect of amount and intensity of a consumable on aging, maturation, and growth of mature humans (adults) as well as human children.

In some embodiments, system 1300 and its associated method estimate predictions on short-term and long-term health effects of consumption of an item (based on the cumulative consumption over time) In some embodiments, system 1300 and its associated method chart the cumulative effect of continued ingestion of certain ingredients or groups of ingredients, on build up toxins and other health effects (perhaps digestion and blood components) over time, wherein the effects are:
   a. deleterious (e.g., certain types of rice when consumed regularly over long periods of time due to their arsenic content); or
   b. advantageous (e.g., almonds due to their vitamin E content).

In some embodiments, system 1300 and its associated method calculate calories from one of a plurality of methods (such as determining calories from the portion size as derived from a calibrated set of one or more images captured on the camera of the human user's smartphone, combined with the type of food and ingredients determined from a QR code or OCR of the item's label, electrical conductivity as measured by sensors on the user's smartphone, and GPS source information and the like).

In some embodiments, system 1300 and its associated method compute calories in an item by taking known (calculated by algorithm such as 1302) calories by volume of the given substance and compare by volume given by device. (E.g., see example prior-art methods to determine linear and/or volume measurements of objects that include U.S. Pat. No. 8,897,539 titled "Using images to create measurements of structures through the videogrammetric process" and PCT Publication No. WO2013/173383 by Brilakis et al. titled "Methods and apparatus for processing image streams," U.S. Pat. No. 8,855,406 to Lim, et al. titled "Egomotion using assorted features," and U.S. Patent Publication No. US2013/0083990, which are each incorporated by reference. U.S. Pat. No. 8,953,024, the disclosure of which is incorporated herein in its entirety, indicates that 3D digital models of scenes can be generated using a passive digital video camera using, in one implementation, structure from motion algorithms.)

In some embodiments, system 1300 and its associated method take, as above, volume of item, and calculate calories by algorithm to actual calories in a particular serving size.

In some embodiments, system 1300 and its associated method determine presence of industrial calories (i.e., calories from large-scale manufacturing) e.g.:
   a. high-fructose corn syrup (HFCS);
   b. artificial sweeteners; or
   c. good vs. bad vs. toxic as defined by each user 60.

In some embodiments, system 1300 and its associated method determine the balance of calories:
   a. from intake vs. physical activity either input to, or detected by, the user's personal device (add device sensor as well as user input); or
   b. by computations against the "calorie clock" (total calories accumulated in body over various extended periods of time).

In some embodiments, system 1300 and its associated method identify specific substances or ingredients by providing health requirements or choice information.

In some embodiments, system 1300 and its associated method identify any unwanted compound(s) or substance(s) in an item and display to user the name of the identified unwanted substance(s) and/or display the deleterious effects on the health of the user, and/or the cost to society's economy and the community.

In some embodiments, system 1300 and its associated method identify spiritual/conscientious-objection-type allergens (a particular user's personal discomfort with eating any part of insects/arthropods, dogs, frogs or horses) in a given item (substances deemed unfit for consumption by the particular user or a given group or subset of individuals with whom the user identifies).

In some embodiments, system 1300 and its associated method identify substances that either pose a health risk to most humans, specific groups of humans, or specific individual humans, or could interact with medications or other foods or other items the user is using.

In some embodiments, system 1300 and its associated method identify and alert users for GMOs (genetically modified organisms, e.g., *brassica* (broccoli, cauliflower and the like), tomatoes and the like, and/or meat from GMO animals (e.g., GMO salmon) or animals that were fed GMO feed). For example, if the user's profile indicates that the particular user wants such notifications (which may be selected by the user on a food-by-food selection that provides warnings for some foods but ignores GMO content of other foods or cosmetics), then certain notifications will be provided and other notifications may be selected to not be presented.

In some embodiments, system 1300 and its associated method identify additives and added colors in an item, by image, scent, etc.

In some embodiments, system 1300 and its associated method measure deliciousness by detecting the presence and concentration of natural flavorings (e.g., isoflavonoids) vs. synthetic flavorings (e.g., even if one or the other include FDA-blessed ingredients).

In some embodiments, system 1300 and its associated method detect presence of monosodium glutamate (MSG), hormones or hormone-like substances, precursors or other consumer suggested and sensitive substances set forth in a particular user's profile.

In some embodiments, system 1300 and its associated method detect presence of certain non-nutritive fillers in food or cosmetics (e.g., titanium dioxide).

In some embodiments, system 1300 and its associated method include data about various groups such as preferences based on, for example, ethnicity, nationality, religious affiliation or other groups, to identify food choices and aversions and help with decisions thereof.

In some embodiments, system 1300 and its associated method detect the amount of iron (for iron sensitivities, iron deficiencies, and overdose protection).

In some embodiments, system 1300 and its associated method track and alert the user as to whether any targeted nutrients are being over-consumed or under-consumed by the particular user over a period of time (per day, week, month etc.; for example, five bags of potato chips in one evening might be too much, one serving of vegetables per week may be too little).

In some embodiments, system 1300 and its associated method chart and/or graph the effect on insulin of the consumption of a food item or sugar intake (e.g., the glycemic index assigned to a food item is a value based on how slowly or how quickly that food item causes increases in blood glucose levels) over a period of time), for example, by outputting a decision graph for user's use in deciding on more insulin or more food.

In some embodiments, system 1300 and its associated method graph blood insulin or blood sugar resulting from consumption of food/energy and insulin by the user.

In some embodiments, system 1300 and its associated method elicit and receive from the user information regarding groups of users that the user considers herself or himself to be members of, and for each group of users, information elicited and received from all the users is aggregated and then user to provide customized advice or other relevant information to users in that group that is based on the collective experiences of the entire group from their past use of the particular consumable (in some embodiments, a group-inclusion method is used such as described in U.S. Pat. No. 8,166,026 to Sadler, which is incorporated herein by reference).

In some embodiments, system 1300 and its associated method provide a rating of a consumable based on consumer information and reactions available (e.g., similar to Michelin Stars® or Kelly's Blue Book® ratings).

In some embodiments, system 1300 and its associated method alert the user to the level of capsaicin or linseeds that may be a problem for persons having irritable bowel syndrome, and tell the user whether the item meets or exceeds wanted amounts.

In some embodiments, system 1300 and its associated method identify artificial sweeteners of questionable healthfulness when used on an ongoing or continuous basis (such as saccharine, aspartame, *stevia* (a type of botanical plant) derivatives—e.g., types of natural sweetener, such as Truvia® or PureVia®, and the like) in consumables.

In some embodiments, system 1300 and its associated method identify the possible presence of gluten.

In some embodiments, system 1300 and its associated method identify specific substances or ingredients that are problematic for all humans, depending on dosage, and which are identified by sensor data combined with warnings, alerts and database information on toxicity levels (e.g., on an item-by-item basis as well as on an accumulated level resulting from consumption over the lifetime, so far, of the user), similar to those provided on a per-user basis as described above, but concentrating on effects that affect the population generally.

In some embodiments, system 1300 and its associated method determine the presence of heavy metals (e.g., Cd, As, Pb and/or Hg), and/or organic or other toxins and the like, that are bad for humans. In some embodiments, system 1300 and its associated method identify the amount of iron, copper, nickel, silver, aluminum and other substances or elements cited in peer-reviewed journal articles showing effects (positive or negative) on health, wellness and general well-being.

In some embodiments, system 1300 and its associated method identify the amount of sodium and compute the health effects (include weightings of the food item on food health index and FIT-and-FAT score).

In some embodiments, system 1300 and its associated method identify the amount of neonicotinoids and the like that are detrimental for other animals.

In some embodiments, system 1300 and its associated method detect and identify real and natural versus synthetic flavorings by sensor-detected ingredients.

In some embodiments, system 1300 and its associated method detect the presence and amounts of transfats or other types of undesirable fats or cholesterol in a consumable.

In some embodiments, system 1300 and its associated method use OCR (optical character recognition) for warnings.

In some embodiments, system 1300 and its associated method detect arsenic in imported rice, which can exacerbate early-onset diabetes.

In some embodiments, system 1300 and its associated method identify factors in the environment combined with the stored data of past intake of certain consumable items by the user that could make a difference to the user's health either positively or negatively.

In some embodiments, system 1300 and its associated method identify and alert users of presence of undesirable/dangerous chemicals (heavy metals, melamine, MSG, grapefruit juice interactions with drugs) and unwanted ingredient.

In some embodiments, system 1300 and its associated method determine whether there may be any interactions of a particular food item with nutraceuticals (foods or pills containing health-giving additives and having medicinal benefit) or medicines, such as antibiotics, taken for health. (For example, age-related kidney-stone problems, macular degeneration, and food that trigger formation of kidney stones.)

In some embodiments, system 1300 and its associated method determine, based on peer-reviewed or other scientific data, whether there may be any interactions that may cause changes to mental health or physical well-being (for example, ingredients with precursor compounds to drugs, or other precursor problem-causing ingredients such as those listed in the United Nations Convention against Illicit Traffic in Narcotic Drugs and Psychotropic Substances, 1988), and system 1300 uses this information to modify weightings assigned to the food item by the FIT-and-FAT score.

In some embodiments, system 1300 and its associated method identify current environmental pressures and to alert the user of air- or water-quality factors that affect that particular user e.g., the user's degree of pollen intolerance (or other hypersensitivity term that describes factors such as humidity or smog that cause allergic reactions), e.g., a tipping point.

In some embodiments, system 1300 and its associated method estimate the suggested or optimal period of time between meals, for example by graph presented on the user's PCD, for the user.

In some embodiments, system 1300 and its associated method determine the effect on the child of a parent consuming a food during breast feeding.

In some embodiments, system 1300 and its associated method show the effect on adipose tissue including quality (increase or decrease, and accumulation of components and chemicals).

In some embodiments, system 1300 and its associated method determine the effect on aging (acceleration, deceleration) of consumption of certain consumables and ingredients, and system 1300 uses this information to modify weightings assigned to the food item.

In some embodiments, the present invention includes a "breathalyzer"—type detector inside (or optionally connected to and removable from) the user's personal device that elicits and receives a breath sample from the user. In some embodiments, the sample is analyzed for alcohol and/or other components of the breath. In some embodiments, the device then outputs to the user advice as to the safety of consumption of food or drugs that should not be taken with alcohol (e.g., some erectile-dysfunction pharmaceuticals/drugs are contraindicated if the user has consumed "too much" alcohol, but the user has no objective standard for how much is too much; thus the device can provide a better indication of when not to take certain drugs). In some embodiments, the results of analysis are also used to interact wirelessly between the user's personal device and the user's car to prevent the car from operating if the user is over the legal limit for driving under the influence.

In some embodiments, system 1300 and its associated method elicit and receive information from the user, or the user's PCD 1310 measures the user's skin and eye color, tone, and quality to alert or suggest to the user of foods or items to use or to avoid to improve the user's skin and eye color, tone, and quality, or to avoid irritation or photosensitivity.

In some embodiments, system 1300 and its associated method provide the user information on the effects of a consumable on their mental health versus physical health, and system 1300 uses this information to modify weightings assigned to the food item.

In some embodiments, system 1300 and its associated method provides warnings regarding such things as ultraviolet sun exposure to the skin, dry weather, wet feet that cause fungus infections and like health problems, and the present system 1300 suggests certain foods that may provide benefit in dealing with such conditions. Certain vitamins and pharmaceuticals can be degraded by ultraviolet sun exposure, and in some embodiments, the present invention provides warnings about such consumables that are in the possession of the human user, and system 1300 uses this information to modify weightings assigned to the food item.

In some embodiments, system 1300 and its associated method identifies a geographical-location (point) of origin and time from origin, and system 1300 uses this information to modify weightings assigned to the food item.

In some embodiments, system 1300 and its associated method identify the freshness (e.g., time from packaging of meat, canning of tomatoes, picking of vegetables, processing of chickens and the like until the item is stocked or purchased in a store—for example, vegetables picked in South Carolina, packaged in Texas or Vietnam, and then put on store shelves in Wisconsin or Mexico), to identify whether item was frozen or dehydrated in processing through multiple technologies, for example by image, scent, and the like. In some embodiments, the user may desire to promote eating "local" (wherein each user can choose what that user considers to be local—e.g., within 25 miles or within a state border), or to promote food with minimal industrial preservatives, and reduce transport, greenhouse gasses or other planet-detrimental waste, as well as affecting the user's well-being, and system 1300 uses this information to modify weightings assigned to the food item.

In some embodiments, system 1300 and its associated method determine whether a food or consumable is locally, intra-nationally, or internationally grown), and system 1300 uses this information to modify weightings assigned to the food item.

In some embodiments, system 1300 and its associated method identify type of packaging being used for transport of a given item (e.g., paper or cardboard (with or without a wax coating), versus petroleum polymers versus organic polymers such as "corn plastic" (a corn-derived polymer)).

In some embodiments, system 1300 and its associated method detect, via the amount of TBA (thio barbituric acid) or other peer-reviewed and recognized methods, a specified item's age and/or level of rancidity, and system 1300 uses this information to modify weightings assigned to the food item.

In some embodiments, system 1300 and its associated method obtain best-by-date, expiration-date, or sell-by-date data and estimate continued useful shelf life, and system 1300 uses this information to modify weightings assigned to the food item.

In some embodiments, system 1300 and its associated method obtain unbiased date from a separate independent company or university or governmental agency used to test for consumables and report via a service to end users on real consumable quality of food from apparent quality as reported by assembler, distributor or manufacturer of consumable, and system 1300 uses this information to modify weightings assigned to the food item.

In some embodiments, system 1300 and its associated method identify situations (either positive or negative) that arise in the environment due to procurement or cultivation of the consumable, and system 1300 uses this information to modify weightings assigned to the food item.

In some embodiments, system 1300 and its associated method identify ecological impact of production of a particular item (e.g., deforestation, ocean health, fertilizer, carbon-water use), and system 1300 uses this information to modify weightings assigned to the food item.

In some embodiments, system 1300 and its associated method identify whether a product is of an endangered species (or protected) or it hurts the environment of the endangered species, and system 1300 uses this information to modify weightings assigned to the food item.

In some embodiments, system 1300 and its associated method identify the amount of water/carbon/phosphorus/contribution to ocean acidity of items required to produce a consumable item, and system 1300 uses this information to modify weightings assigned to the food item.

In some embodiments, system 1300 and its associated method identify actions by the companies and individuals that are involved in the production of an item for the user's education, and system 1300 uses this information to modify weightings assigned to the food item.

In some embodiments, system 1300 and its associated method identify firms responsible for production of certain items, including an analysis of CEO and treatment of employees, and system 1300 uses this information to modify weightings assigned to the food item.

In some embodiments, system 1300 and its associated method identify whether an item was produced, manufactured and processed in a geographical region such as war, famine and other major human disasters regions that are bad for human rights, and system 1300 uses this information to modify weightings assigned to the food item.

In some embodiments, system 1300 and its associated method identify whether an item was produced, manufactured and processed in a manner affected by ecological disasters (e.g., hurricane damage to nuclear plant or rice downstream from mine-tailings dump, Fukushima Japan beef cattle or milk, vegetables from agriculture above an oil field created or modified using hydraulic fracturing ("fracking") technology, or in a manner that causes, or results from, ocean acidification or ocean dumping), and system 1300 uses this information to modify weightings assigned to the food item.

In some embodiments, system 1300 and its associated method determine, via a peer-reviewed organization, whether bonded labor was used in producing the product (user-defined aversions to certain labor practices, child labor, prison labor, captive labor, too-low wages, unsafe working conditions (e.g., yeast, formaldehyde, ammonia, pesticides), unsupported labor, labor of aged populations (e.g., stores with low wages and no benefits) or the like), and system 1300 uses this information to modify weightings assigned to the food item.

In some embodiments, system 1300 and its associated method provide a historical database of company contamination both environmental and product (e.g., Companies that pump raw sewage out, chemical dumping), and system 1300 uses this information to modify weightings assigned to the food item.

In some embodiments, system 1300 and its associated method determine an index for companies' and CEO's interaction with local communities, and system 1300 uses this information to modify weightings assigned to the food item.

In some embodiments, system 1300 and its associated method determine possible breaches with international law and trade embargoes as well as the personal sensitivities ("spiritual allergies") of each individual user (to items such as, e.g., Blue Fin Tuna, turtles and dolphin meat), and system 1300 uses this information to modify weightings assigned to the food item.

In some embodiments, system 1300 and its associated method determine information on funding to hostile governments or organizations that violate human rights, embargoes, labor conditions), and system 1300 uses this information to modify weightings assigned to the food item.

In some embodiments, system 1300 and its associated method determine the effect of Company's actions on global ecology, e.g., deforestation for growing certain foods, and system 1300 uses this information to modify weightings assigned to the food item.

In some embodiments, system 1300 and its associated method determine the effect of a particular company's actions on global economy, and system 1300 uses this information to modify weightings assigned to the food item that comes from that company.

In some embodiments, system 1300 and its associated method have user's device to offer an index of human rights, company index and CEO index of the food purchased or consumed, and system 1300 uses this information to modify weightings assigned to the food item.

In some embodiments, system 1300 and its associated method provide information on sources of business practices etc. also allow users to provide data on sources business practices to the cloud, and system 1300 uses this information to modify weightings assigned to the food item.

In some embodiments, system 1300 and its associated method provide information animals raised in small farms, or in humanly thought environments, e.g., animal treatment and processing methods designed by Dr. Temple Grandon, and system 1300 uses this information to modify weightings assigned to the food item.

In some embodiments, system 1300 and its associated method provide information that allow the app to update itself or be updated remotely including starting application remotely (e.g., to notify user of urgent and exigent data about an item that was determined, after an earlier initial recommendation to the user about positive or negative aspects of a particular item; i.e., ALERTS!).

In some embodiments, system 1300 and its associated method repeated gather information checked against, FDA, FCC, USDA and CDC alerts, recalls, and database changes, and signal to those affected users of changes that would be made relative to past recommendations and warnings.

In some embodiments, system 1300 and its associated method track what a user has bought over time, and alert them if dangers are later found, (e.g., after buying product X, it is found to be contaminated with Y, so an alert is sent to the device/fridge/user that the particular identified food has an issue with consumption; for example, lead (Pb)-tainted curry that was perhaps used in a particular batch of red lentil butter). This could also be used to track the user's intake of certain items and nutrients, and could provide a nudge to eat things with certain attributes to enhance or augment the user's diet.

In some embodiments, system 1300 and its associated method track, as above, the user's purchases and diet, but sends notifications (which are not necessarily solicited by the user at the time) through text, calls, and/or email, and which, in some embodiments, turn-on or activate the user's smartphone 1310, wearable device or other appliances 1319 that are part of the IOT infrastructure, and wherein upon activation, the device, without additional user input, presents to the user one or more notifications or warnings.

In some embodiments, system 1300 and its associated method track calculate values for score and health by comparison to known values and algorithms, and system 1300 uses this information to modify weightings assigned to the food item.

In some embodiments, system 1300 and its associated method track determine a score based on different values added and subtracted from a base-health score, e.g., base-health score=[caloric density plus percent of food that is as advertised (what percent of each meat is there)—(food glycemic index) minus exercise calories), and system 1300 uses this information to modify weightings assigned to the food item for this particular user given their current MIL score.

In some embodiments, system 1300 and its associated method determine a grade (which, in some embodiments, is indicated by a numerical or alphabetic score, one of a set of colors of differing hues, brightnesses, and/or saturations, appealing or aversive photograph or the like) of a food based on similar variables as previously indicated herein, and system 1300 uses this information to modify weightings assigned to the food item.

In some embodiments, system 1300 and its associated method calculate a Gut health score, a skin score, and a heart and blood score, and system 1300 uses this information to modify weightings assigned to the food item.

In some embodiments, system 1300 and its associated method determine a food-satisfaction score created by a community of users (e.g., crowd-sourced data such as used in travel activities such as resort, hotel or restaurant scores), and system 1300 uses this information to modify weightings assigned to the food item.

In some embodiments, system 1300 and its associated method detect the presence of various substances to derive a measure of the quality or freshness of the consumable, and system 1300 uses this information to modify weightings assigned to the food item.

In some embodiments, system 1300 and its associated method use additional reagents (such as inexpensive and non-toxic antibodies that attach only to certain DNA sequences (such as, for example, dolphin or horse meat, or certain toxic microbes) and fluoresce in ultraviolet light supplied by the user's smartphone) or stains (such as a stain that changes color due to gram-negative bacteria, or such as other suitable dyes or solvents, that are applied to the consumable enhance the ability of digital photographs or visual inspection by the human user to detect certain substances or to derive a measure of the quality or freshness of the consumable. In some embodiments, the results of such tests and measurements are collected by the human user's smartphone and communicated back the present invention's central database for use in communicating to other users of the same or similar food items.

In some embodiments, system 1300 and its associated method determine deliciousness of an item, defined by [savoriness, mouth feel, crispness, sweetness, tartness, meets craving of humans, user-centric empirically determined, TBA (thiobarbituric acid) and/or tocopherols (Vitamin E) values or the like]

In some embodiments, system 1300 and its associated method identify level of processing of a food (level of processing (LP) scores, from, for example, LP1 (e.g., carrot directly from the earth and washed off and promptly delivered to the retail store and sold without adulteration by preservatives or freezing) to LP5 (e.g., TV dinner that includes beef that has been frozen, thawed, cooked, treated with preservatives, pumped with sauces, transported across thousands of kilometers, and the like) (in some embodiments, LP0 is considered as "fruits and vegetables eaten in the field as it is picked, brushed off and/or rinsed")).

In some embodiments, system 1300 and its associated method identify whether a product has issues (such as characteristics that affect health) or is properly cooked and otherwise well-prepared, as well as determining nutrients in item after cooking, (e.g., through thermal imaging).

In some embodiments, system 1300 and its associated method output scores and other information to the user. In some embodiments, this includes grades, scores, or color designations for different values and results. In some embodiments the present invention includes a device and method to use the user's preferences, or the preferences of groups the user ascribes to, to better inform the user.

In some embodiments, system 1300 and its associated method provide a wellness and health index of a food item (using labels such as LP 1 to LP 5)

In some embodiments, system 1300 and its associated method output information to the user regarding wasteful packaging used in delivering the consumable to the user.

In some embodiments, system 1300 and its associated method output the amount of different daily values (e.g. calories, protein, carbs, sodium, etc.) present in the consumable.

In some embodiments, system 1300 and its associated method output the possible presence of specific allergens, and in some embodiments the likelihood of an allergen.

In some embodiments, system 1300 and its associated method output a FIT-and-FAT score and/or MIL score calculated by one or more of the methods described above.

In some embodiments, system 1300 and its associated method alert the user before they consume something that could threaten their health. In some embodiments, this includes vibration, sound, visual notification, or alerts sent to connected devices. In some embodiments, the present invention includes a device and method to communicate with other devices, in an "internet of things" (JOT).

In some embodiments, system 1300 and its associated method have a number of different modes or apps to focus on individual aspects of the process In some embodiments, the database server 1320 includes the functionality to identify deficiencies and detrimental properties of ingredients in the item, and, based on the identified deficiencies and detrimental properties, the database server solicits and sells advertising for local establishments that could provide useful alternatives for immediate delivery, or companies that make alternative products or supplements and corrective (items that counteract or offset the deficiencies and detrimental properties) items related to the item contemplated for the user (antioxidants, vegetables, fiber and the like).

In some embodiments, the class of things considered to be "consumable items 80" is expanded to include physical and mental activities engaged by the user 60 (such as running, walking, playing video games, interacting on their PCD 1310 via social media with other persons, watching television, sleeping). In some embodiments, the PCD 1310 of the user 60 automatically detects, tracks, and records a history such activities based on the sensors and communication features of the user's PCD 1310, in order to provide input variables to the MIL score kept by the user's PCD 1310, and to present contemporaneous feedback to the user 60. In some embodiments, the histories 1358 of consumable items 80 consumed by (optionally including activities engaged in by the user 60, as just described) each of a specified group individuals having certain identified physiological characteristics (e.g., asthma, attention-deficit hyperactivity disorder (ADHD) or Asperger's syndrome) are periodically analyzed and correlated with self-reported feelings of better or worse wellbeing or control of symptoms. The results of the analyses are used to adjust the weightings of the plurality of stored parameters X1, X2, X3, ... Xn in each affected user's user profile 1338 (and/or user account 1348), and/or to adjust the weightings of the plurality of stored parameters W1, W2, W3, ... Wn in each affected consumable item in the database of consumable items 1343. In some embodiments, the output 1355 (which is sent to and presented from the PCD 1310 of the user 60 affected by the results) is adjusted to provide the user 60 improved guidance for self-control of their wellbeing.

In some embodiments, system 1300 and its associated method calculate a FIT-and-FAT score (Food-Information-Technology and Food-to-Aging Trajectory score) by starting at a neutral point in the range of values of the FIT and FAT score, and then:

incrementing (or multiplying by a factor greater than one) (by a weighted amount determined by the type and amount of benefit) the score for each positive aspect of the ingredients in the contemplated item (including positive interactions and accumulations with items already consumed by the user in the past) and decrementing (by a weighted amount determined by the type and amount of harm) the score for each negative aspect of the ingredients in the contemplated item (including negative interactions and accumulations with items consumed by the user in the past).

In some embodiments, system 1300 and its associated method elicit and receive, from the user, modifications to the weights assigned to each type or item of food as desired by each user.

In some embodiments, system 1300 and its associated method determine whether the consumable fits well with the user's preference for a particular lifestyle, level of exercise, or chosen occupation. For example, see *The Fire of Life: An Introduction to Animal Energetics, Revised Edition*, (1961, republished 1975) by Max Kleiber.

In some embodiments, system 1300 and its associated method identify whether a consumable wastes feed in its production or a food source (such as a restaurant) wastes food in its operation (e.g., beef cattle use more feed than fish; some restaurants toss much edible food while other restaurants donate excess food to charity or food shelves). This can also apply to the wasting of water.

In some embodiments, system 1300 and its associated method determine the presence of illegal and/or illicit substances in food (non-desirable foreign matter, cocaine, alcohol or the like) or food containers/packaging In some embodiments, system 1300 and its associated method include everything here, but with the invention customized for animals (companion pets, livestock and curated animals/zoos).

In some embodiments, the present invention provides household devices communicating with one another as "internet-of-things" (IOT), such as a refrigerator that includes a display screen that displays information as to the inventory of food within the refrigerator. The inventory includes such information as the type of food, the source (which store was it purchased at as well as what farm grew the food item), the date when it was placed in the refrigerator originally and the date when it was cooked and the leftovers placed in the refrigerator. This display is connected to the database server of the present invention as well as the user's personal electronic device (such as smartphone or tablet). The database server receives information from regulatory agencies (such as the Food and Drug Administration (FDA) recalls or warnings or the like), from manufacturers, and from retail food stores—this information includes ingredients, sources of the ingredients, dates that the ingredients were processed and the like. Accordingly, when the FDA issues a recall on a certain ingredient, the database server of the present invention associates that recalled ingredient with all the food products made from the recalled ingredient and all the end-users who bought those food products, and via the user's IOT refrigerator or the user's smartphone, alerts the user to the presence of the recalled ingredient and the associated food items. In some embodiments, the present invention "turns-on" or activates the user's IOT refrigerator or the user's smartphone to actively alert the user without the user needing to turn on the device or activate some program with an inquiry as to whether any contents of the IOT refrigerator includes a recalled or warned-about item.

Although the FDA issues recalls very frequently, but the recalls do not affect a large portion of the population and the general population will not bother to receive the hundreds of warnings that likely do not apply to them. The present invention provides a filtering mechanism that sends alerts only to those users that the system has tracked and that the system has identified as having purchased the particular affected food items.

The market-a proxy for the same example-this happens 5-10 times per year

There is a portion of the population that have "spiritual allergies" to certain food entities (such as, for example, non-Kosher items, beef, horsemeat, and the like) as well as actual allergies to certain food entities (such as, for example, peanuts, insect colorings, or egg or milk products) and the present invention provides a method and device that warns the user—before making the purchase—of the presence of ingredients that trigger the "spiritual allergies." In addition, in some embodiments, the present invention tracks all or most of the items that each user has already purchased, and repeated scans the database information from the government and from manufacturers and suppliers for new data, (data not previously available), that indicates the presence of the "spiritual allergens" (for example, if it is later discovered that a spiritual allergen or an actual allergen is in an ingredient), the user's IOT refrigerator and/or the user's smartphone will, by itself, turn on and actively flash a light or audio alarm or the like, alerting the user and notifying the user of the nature of the problem, the exact food item, as well as possible solutions or remedies to help assuage and/or reduce the health effects.

In some embodiments, the present invention provides an apparatus that includes: a personal computing device (PCD) of a first human user, wherein the PCD of the first human user is communicatively coupled to a database server system, wherein the database server system includes one or more computers connected to one another and the internet, wherein the PCD of the first human user elicits and receives, from the first human user, identifying information as to each of a plurality of consumables that user has purchased and when each of these consumables was purchased, wherein the database server system obtains and stores information, warnings and recalls from the United States FDA (Food and Drug Administration) and from manufacturers of the plurality of consumables, wherein the database server system correlates the information, warnings and recalls with the identifying information, identified and stored for the first human user, regarding products and ingredients in the consumables of the first human user; and wherein at least one of the first user's PCD and the database server system determines a FIT and FAT score as to the exact consumable affected and outputs the score to the first user.

In some embodiments, the present invention provides a method that includes: providing a user's personal computing device having a plurality of sensors; identifying a chosen consumable item and its components and current age and state/condition; screening for known detrimental factors and beneficial effects; identifying known beneficial factors and effects; identifying ingredients, allergens, health quality, age, origin, and/or amount/quantity of the food item; presenting, from the user's personal computing device, resulting data, recommendations and or alternatives to the user, in order to create the ability to judge a quality of a food, the effects of consumption on the user, and the effects of production of said item, to gain far more detailed knowledge of the items the user ingests to replace inferior choices of food items with items that are better for the individual, society in general, the environment, endangered species, and the like, and to limit the impact and damage caused by consumption of a given consumable (e.g., food item, cosmetic, and/or pharmaceutical and combinations thereof). Some embodiments of this method further include successively activating flashes from LEDs that emit different spectra; obtaining a plurality of images of the chosen consumable item, wherein each of the plurality of images obtains image data from a different one of the successive LED flashes; deriving data from each of the plurality of images and/or differences between the image data from pairs of the images; and pattern-matching the derived data to determine ingredients, allergens, health quality, age, origin, and/or amount or quantity of the food item.

Some embodiments of this method further include storing data on a nutrient-database computer server (obtained, e.g., from databases provided by food companies, universities, user groups, non-governmental organizations (NGOs) and governmental agencies) regarding a plurality of consumables and their ingredients and effects; communicating data from the user's personal computing device to the nutrient-database computer server, wherein the data includes information specific to the particular user and to the particular food item; processing the data on the nutrient-database computer server; communicating data back from the nutrient-database computer server to the user's personal computing device; and outputting from the user's personal computing device a presentation based on the data in the user's personal computing device and the data communicated from the nutrient-database computer server. Some embodiments of this method further include storing data on a nutrient-database computer server (obtained, e.g., from databases provided by food companies, universities, user groups, non-governmental organizations (NGOs) and governmental agencies) regarding a plurality of consumables and their association(s) with a producer (such as a gun manufacturer or a company run by a venture capitalist (stock gambler) invested in food companies); communicating data from the personal user computing device to the nutrient-database computer server, wherein the data includes information specific to the particular user and to the particular food item; processing the data on the nutrient-database computer server; and communicating data back from the nutrient-database computer server to the user's personal computing device; and outputting from the user's personal computing device a presentation based on the data in the user's personal computing device and the data communicated from the nutrient-database computer server. In some embodiments, the nutrient database includes information regarding non-nutrient biochemicals associated with each one of a plurality of identified ingredients and consumables.

It is to be understood that the above description is intended to be illustrative, and not restrictive. Although numerous characteristics and advantages of various embodiments as described herein have been set forth in the foregoing description, together with details of the structure and function of various embodiments, many other embodiments and changes to details will be apparent to those of skill in the art upon reviewing the above description. The scope of the invention should be, therefore, determined with reference to the appended claims, along with the full scope of equivalents to which such claims are entitled. In the appended claims, the terms "including" and "in which" are used as the plain-English equivalents of the respective terms "comprising" and "wherein," respectively. Moreover, the terms "first," "second," and "third," etc., are used merely as labels, and are not intended to impose numerical requirements on their objects.

What is claimed is:

1. A method comprising:
providing a personal computing device (PCD) for a first user, wherein the PCD includes a plurality of sensors including a camera;
receiving, into the PCD, image data from the camera;
identifying a boundary of a chosen consumable item in the image data;
generating histogram data based on at least saturations and hues of pixels within the boundary of the chosen consumable item in the image data;
using the histogram data, identifying a plurality of at least three selected from the group consisting of: the chosen consumable item, the chosen consumable item's components, the chosen consumable item's current age, and the chosen consumable item's condition;
communicating, to a database server, the identifications of the plurality of at least three selected from the group consisting of: the chosen consumable item, the chosen consumable item's components, the chosen consumable item's current age, and the chosen consumable item's condition;
identifying, in the database server, a plurality of the set consisting of ingredients, allergens, and toxins in the chosen consumable item based on the communicated identifications of the plurality of at least three selected from the group consisting of: the chosen consumable item, the chosen consumable item's components, the chosen consumable item's current age, and the chosen consumable item's condition;
looking up, in the database server, a plurality of known detrimental, beneficial and health-quality effects on the first user's health for each of the plurality of the set consisting of ingredients, allergens, and toxins in the chosen consumable item;
determining an effect on biological aging of the first user resulting from consumption of the chosen consumable item, wherein the effect is determined by starting with a score at a neutral point in a range of values, incrementing the score based on the looked-up beneficial effects of at least some of the chosen consumable item's ingredients, and decrementing the score based on the looked-up detrimental effects of at least some of the chosen consumable item's ingredients; and
presenting to the first user, from the first user's PCD, a comparison of a plurality of parameters of the chosen consumable item to at least one alternative consumable item based on the effect on the biological aging of the first user.

2. The method of claim 1 wherein the identifying of the chosen consumable item further includes:
successively activating flashes from LEDs that emit different spectra;
obtaining a plurality of images of the chosen consumable item, wherein each of the plurality of images includes image data from a different one of the successive LED flashes;
deriving data from each of the plurality of images and from differences between the image data from at least one pair of the plurality of images; and
pattern-matching the derived data to determine a plurality of at least three selected from the group consisting of: ingredients, allergens, health quality, age, origin, and amount of the chosen consumable item.

3. The method of claim 1, further comprising:
storing consumables-and-ingredients data regarding a plurality of consumables and their ingredients and effects on a nutrient-database computer (server, wherein the consumables-and-ingredients data are obtained from databases provided by food companies and one or more governmental agencies;
communicating specific-user-and-item data from the first user's PCD to the nutrient-database computer server, wherein the specific-user-and-item data includes information specific to the first user and to the chosen consumable item;
processing the specific-user-and-item data on the nutrient-database computer server;
communicating data back from the nutrient-database computer server to the first user's PCD; and
outputting from the first user's PCD a presentation based on the data in the first user's PCD and the data communicated from the nutrient-database computer server.

4. The method of claim 1, further comprising:
storing consumables-and-associations data regarding a plurality of consumables and their association(s) with a producer on a nutrient-database computer server, wherein the consumables-and-associations data are obtained from databases provided by food companies and governmental agencies;
communicating specific-user-and-item data from the PCD to the nutrient-database computer server, wherein the specific-user-and-item data includes information specific to the first user and to the chosen consumable item;
processing the specific-user-and-item data on the nutrient-database computer server;
communicating data back from the nutrient-database computer server to the first user's PCD; and
outputting from the first user's PCD a presentation based on the data in the first user's PCD and the data communicated from the nutrient-database computer server.

5. The method of claim 1, wherein the chosen consumable item is a food item.

6. The method of claim 1, wherein the chosen consumable item is a cosmetic item.

7. The method of claim 1, further comprising:
using a plurality of resulting data selected from recommendations and alternatives, a health impact and quality of the chosen consumable item, determining one or more effects of consumption of the chosen consumable item on the first user, and one or more effects of production of the chosen consumable item on an environment; and
if the chosen consumable item is determined to be an inferior choice, outputting, via the PCD, replacement choices of consumable items that are better for the first user, society in general, the environment, endangered species, and that limit impact and damage caused by consumption of the chosen consumable item.

8. The method of claim 1, further comprising:
storing motion information from the first user's PCD and based on the motion information, calculating a movement-in-life (MIL) score for the first user; and
adjusting the comparison of the plurality of parameters based on the MIL score.

9. The method of claim 1, further comprising:
receiving, in the first user's PCD, air-borne chemical information associated with the chosen consumable item, and, based on the air-borne chemical information, adjusting the comparison of the plurality of parameters.

10. The method of claim 1, further comprising:
receiving, in the first user's PCD, electrical conductivity information associated with the chosen consumable item, and, based on the electrical conductivity information, adjusting the comparison of the plurality of parameters.

11. The method of claim 1, further comprising:
receiving information, warnings and recalls from a United States Food and Drug Administration database and from manufacturers of a plurality of consumable items;
correlating the information, warnings and recalls with identifying information identified and stored for the first user, regarding products and ingredients in previously chosen consumable items of the first user;
filtering the information to just those consumables affected consumable items that the first user has purchased and that have been affected by a warning or recall that has been issued; and
automatically activating the first user's PCD and/or an internet of things (IOT) appliance of the first user such that the first user's PCD and/or the first user's IOT appliance alerts the first user as to the nature of the warning and as to the consumable affected.

12. An apparatus comprising:
a personal computing device (PCD) of a first user, wherein the PCD of the first user includes:
a plurality of sensors including a camera;
a processor and storage, wherein the processor is operatively coupled to:
receive image data from the camera,
identify a boundary of a chosen consumable item in the image data,
generate histogram data based on at least saturations and hues of pixels within the boundary of the chosen consumable item in the image data,
identify, based on the histogram data, a plurality of at least three selected from the group consisting of: the chosen consumable item, the chosen consumable item's components, the chosen consumable item's current age, and the chosen consumable item's condition, and
identify a plurality of ingredients in the chosen consumable item based on the plurality of at least three selected from the group consisting of: the chosen consumable item and the chosen consumable item's identified components, the chosen consumable item's current age, and the chosen consumable item's amount;
a communication subsystem operatively coupled to the processor, wherein the communication subsystem is communicatively coupled to a remote database server system, wherein the remote database server system includes one or more computers connected to one another and an internet,
an input-output subsystem operatively coupled to the processor, wherein the input-output subsystem elicits and receives, from the first user, identifying information as to each of a plurality of consumables that the first user has purchased including the chosen consumable item, and when each of these consumables was purchased;
a database in the storage and coupled to the processor and the remote database server system, wherein the database and the remote database server system obtain and store information, warnings and recalls from a United States Food and Drug Administration database and from manufacturers of the plurality of consumables;
a calculation unit in the processor that correlates the information, warnings and recalls with identifying information, identified and stored for the first user, regarding products and ingredients in the consumables of the first user, wherein the calculation unit filters the information to just those consumables affected that the first user has purchased such that when a warning or recall has been issued that affects one of the plurality of consumables of the first user, the remote database server system automatically activates the first user's PCD and/or an internet of things (IOT) appliance of the first user such that the first user's PCD and/or the first user's IOT appliance alerts the first user as to a nature of the warning and as to the consumable item affected, wherein the calculation unit further determines an effect of consumption on biological aging of the first user resulting from consumption of the chosen consumable item, wherein the effect is determined by starting with a score at a neutral point in a range of values, incrementing the score based on looked-up beneficial effects of at least some of the chosen consumable item's ingredients and decrementing the score based on looked-up detrimental effects of at least some of the chosen consumable item's ingredients; and
a display on the first user's PCD, wherein the display displays a comparison of a plurality of parameters of the chosen consumable item to at least one alternative consumable item based on the effect on the speed of biological aging of the first user.

13. The apparatus of claim 12, further comprising a personal home computer system of the first user that has a plurality of appliances each having wireless communications connected as an internet of things (IOT).

14. The apparatus of claim 12, wherein the first user's PCD alerts the first user via at least one of the set consisting of lights flashing, specific sounds, and haptic vibrations.

15. The apparatus of claim 12, further comprising:
a motion detector operatively coupled to the processor in the first user's PCD, wherein the motion detector generates motion information, wherein the processor, based on the motion information, calculates a movement-in-life (MIL) score, and adjusts the comparison of the plurality of parameters based on the MIL score.

16. The apparatus of claim 12, further comprising:
an air-borne chemical detector operatively coupled to the processor in the first user's PCD, wherein the motion detector generates air-borne chemical information associated with the chosen consumable item, and wherein the processor adjusts the comparison of the plurality of parameters based on the air-borne chemical information.

17. The apparatus of claim 12, further comprising:
an electrical conductivity detector operatively coupled to the processor in the first user's PCD, wherein the electrical conductivity detector generates electrical conductivity information associated with the chosen consumable item, and wherein the processor adjusts the comparison of the plurality of parameters based on the electrical conductivity information.

18. The apparatus of claim 12, further comprising:
a far-long infra-red (FLIR) imager operatively coupled to the processor in the first user's PCD, wherein the FUR imager generates FUR image information associated with the chosen consumable item, and wherein the processor, based on the FUR image information, adjusts the comparison of the plurality of parameters based on the FUR image information.

19. An apparatus comprising:
a personal computing device (PCD) of a first user, wherein the PCD includes a camera that generates image data;
means for identifying a boundary of a chosen consumable item in the image data;
means for generating histogram data based on at least saturations and hues of pixels within the boundary of the chosen consumable item in the image data;
means for using the histogram data to identify a plurality of at least three selected from the group consisting of: the chosen consumable item, the chosen consumable item's components, the chosen consumable item's current age, and the chosen consumable item's condition;
means for communicatively coupling the PCD of the first user to a database server system, wherein the database server system includes one or more computers connected to one another and an internet;
means for eliciting and receiving, into the PCD of the first user, from the first user, identifying information as to each of a plurality of consumables that the first user has purchased and when each of these consumables was purchased;
means for obtaining and storing into the database server system information, warnings and recalls from a United States Food and Drug Administration database and from manufacturers of the plurality of consumables; and
means for correlating, in the database server system, the information, warnings and recalls with the identifying information in the PCD regarding products and ingredients in the consumables of the first user;
means for filtering, in the database server system, the information to just those affected consumable items that the first user has purchased;
means for automatically activating the first user's PCD and/or an internet of things (IOT) appliance of the first user when a warning or recall has been issued that affects one of the plurality of consumables of the first user, such that the first user's PCD and/or the first user's IOT appliance alerts the first user as to a nature of the warning and as to an exact consumable affected;
means for determining an effect of consumption on biological aging of the first user resulting from consumption of the chosen consumable item, wherein the effect is determined by starting with a score at a neutral point in a range of values, incrementing the score based on looked-up beneficial effects of at least some of the chosen consumable item's ingredients and decrementing the score based on looked-up detrimental effects of at least some of the chosen consumable item's ingredients; and means for displaying a comparison of a plurality of parameters of the chosen consumable item to at least one alternative consumable item based on the effect on the biological aging of the first user.

20. The apparatus of claim 19, wherein the chosen consumable is a food item.

* * * * *